United States Patent
Saadat et al.

(10) Patent No.: US 10,064,540 B2
(45) Date of Patent: Sep. 4, 2018

(54) VISUALIZATION APPARATUS FOR TRANSSEPTAL ACCESS

(75) Inventors: Vahid Saadat, Saratoga, CA (US); Amir Abolfathi, Woodside, CA (US); Chris A. Rothe, San Mateo, CA (US); Kevin H. Van Bladel, Livermore, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1039 days.

(21) Appl. No.: 11/763,399

(22) Filed: Jun. 14, 2007

(65) Prior Publication Data
US 2007/0293724 A1     Dec. 20, 2007

Related U.S. Application Data

(63) Continuation-in-part of application No. 11/560,742, filed on Nov. 16, 2006, now Pat. No. 7,860,556, and
(Continued)

(51) Int. Cl.
*A61B 1/00* (2006.01)
*A61B 1/005* (2006.01)
(Continued)

(52) U.S. Cl.
CPC .......... *A61B 1/00089* (2013.01); *A61B 1/005* (2013.01); *A61B 1/0008* (2013.01);
(Continued)

(58) Field of Classification Search
CPC ...... A61B 1/000112–1/000128; A61B 1/0008; A61B 1/00082; A61B 1/00089;
(Continued)

(56) References Cited

U.S. PATENT DOCUMENTS 623,022 A     4/1899  Johnson
2,305,462 A  * 12/1942  Wolf .............................. 600/135
(Continued)

FOREIGN PATENT DOCUMENTS

DE     2853466 A1    6/1979
DE    10028155 A1   12/2000
(Continued)

OTHER PUBLICATIONS

Avitall, A Catheter System to Ablate Atrial Fibrillation in a Sterile Pericarditis Dog Model, PACE, vol. 17, p. 774, 1994.
(Continued)

*Primary Examiner* — Ryan Henderson

(57) ABSTRACT

Visualization apparatus and methods for transseptal access are described herein where intravascular access across a septal wall is facilitated via devices which provide for direct visual viewing of tissue area. Such a system may include a deployment catheter and an attached imaging hood deployable into an expanded configuration. In use, the imaging hood is placed against or adjacent to the tissue to be imaged in a body lumen that is normally filled with an opaque bodily fluid such as blood. A translucent or transparent fluid can be pumped into the imaging hood until the fluid displaces any blood leaving a clear region of tissue to be imaged via an imaging element in the deployment catheter. Any number of therapeutic tools or a guidewire can be passed through the catheter and into the imaging hood for crossing the septal wall and passing the guidewire or instruments therethrough.

41 Claims, 96 Drawing Sheets

Related U.S. Application Data a continuation-in-part of application No. 11/259,498, filed on Oct. 25, 2005, now Pat. No. 7,860,555, said application No. 11/560,742 is a continuation-in-part of application No. 11/259,498, filed on Oct. 25, 2005, now Pat. No. 7,860,555.

(60) Provisional application No. 60/888,242, filed on Feb. 5, 2007, provisional application No. 60/871,415, filed on Dec. 21, 2006, provisional application No. 60/871,424, filed on Dec. 21, 2006, provisional application No. 60/806,926, filed on Jul. 10, 2006, provisional application No. 60/806,924, filed on Jul. 10, 2006, provisional application No. 60/804,801, filed on Jun. 14, 2006, provisional application No. 60/737,521, filed on Nov. 16, 2005, provisional application No. 60/649,246, filed on Feb. 2, 2005.

(51) Int. Cl.
*A61B 1/313* (2006.01)
*A61B 8/12* (2006.01)
*A61B 1/015* (2006.01)
*A61B 1/018* (2006.01)
*A61B 1/04* (2006.01)
*A61B 5/02* (2006.01)
*A61B 8/00* (2006.01)

(52) U.S. Cl.
CPC ...... *A61B 1/00082* (2013.01); *A61B 1/00085* (2013.01); *A61B 1/015* (2013.01); *A61B 1/018* (2013.01); *A61B 1/04* (2013.01); *A61B 1/3137* (2013.01); *A61B 5/02007* (2013.01); *A61B 8/12* (2013.01); *A61B 8/4472* (2013.01)

(58) Field of Classification Search
CPC ............ A61B 1/00094; A61B 1/00101; A61B 1/00135; A61B 1/00137; A61B 1/00142; A61B 1/00154; A61B 18/24; A61B 18/1492; A61M 25/10
USPC ........ 600/104, 114, 146, 149, 121–125, 127, 600/129, 140
See application file for complete search history.

(56) References Cited

U.S. PATENT DOCUMENTS

| | | |
|---|---|---|
| 2,453,862 A | 11/1948 | Peter |
| 3,559,651 A | 2/1971 | Moss |
| 3,831,587 A | 8/1974 | Boyd |
| 3,874,388 A | 4/1975 | King et al. |
| 3,903,877 A | 9/1975 | Terada |
| 4,175,545 A | 11/1979 | Termanini |
| 4,326,529 A | 4/1982 | Doss et al. |
| 4,403,612 A | 9/1983 | Fogarty |
| 4,445,892 A | 5/1984 | Hussein et al. |
| 4,470,407 A | 9/1984 | Hussein et al. |
| 4,517,976 A | 5/1985 | Murakoshi et al. |
| 4,569,335 A | 2/1986 | Tsuno |
| 4,576,146 A | 3/1986 | Kawazoe et al. |
| 4,615,333 A | 10/1986 | Taguchi |
| 4,619,247 A | 10/1986 | Inoue et al. |
| 4,676,258 A | 6/1987 | Inokuchi et al. |
| 4,681,093 A | 7/1987 | Ono et al. |
| 4,709,698 A | 12/1987 | Johnston et al. |
| 4,710,192 A | 12/1987 | Liotta et al. |
| 4,727,418 A | 2/1988 | Kato et al. |
| 4,772,260 A | 9/1988 | Heyden |
| 4,784,133 A | 11/1988 | MacKin |
| 4,838,246 A | 6/1989 | Hahn et al. |
| 4,848,323 A | 7/1989 | Marijnissen et al. |
| 4,880,015 A | 11/1989 | Nierman |
| 4,911,148 A | 3/1990 | Sosnowski et al. |
| 4,914,521 A | 4/1990 | Adair |
| 4,943,290 A | 7/1990 | Rexroth et al. |
| 4,950,285 A | 8/1990 | Wilk |
| 4,957,484 A | 9/1990 | Murtfeldt |
| 4,960,411 A | 10/1990 | Buchbinder |
| 4,961,738 A | 10/1990 | Mackin |
| 4,976,710 A | 12/1990 | MacKin |
| 4,991,578 A | 2/1991 | Cohen |
| 4,994,069 A | 2/1991 | Ritchart et al. |
| 4,998,916 A | 3/1991 | Hammerslag et al. |
| 4,998,972 A | 3/1991 | Chin et al. |
| 5,025,778 A | 6/1991 | Silverstein et al. |
| 5,047,028 A | 9/1991 | Qian |
| 5,057,106 A | 10/1991 | Kasevich et al. |
| 5,090,959 A | 2/1992 | Samson et al. |
| 5,123,428 A | 6/1992 | Schwarz |
| RE34,002 E | 7/1992 | Adair |
| 5,156,141 A | 10/1992 | Krebs et al. |
| 5,171,259 A | 12/1992 | Inoue |
| 5,197,457 A | 3/1993 | Adair |
| 5,281,238 A | 1/1994 | Chin et al. |
| 5,282,827 A | 2/1994 | Kensey et al. |
| 5,306,234 A | 4/1994 | Johnson |
| 5,313,934 A | 5/1994 | Wiita et al. |
| 5,313,943 A | 5/1994 | Houser et al. |
| 5,330,496 A | 7/1994 | Alferness |
| 5,334,159 A * | 8/1994 | Turkel ............... 604/158 |
| 5,334,193 A | 8/1994 | Nardella |
| 5,336,252 A * | 8/1994 | Cohen ............... 607/119 |
| 5,339,800 A | 8/1994 | Wiita et al. |
| 5,345,927 A | 9/1994 | Bonutti |
| 5,348,554 A | 9/1994 | Imran et al. |
| 5,353,792 A | 10/1994 | Lubbers et al. |
| 5,370,647 A | 12/1994 | Graber et al. |
| 5,373,840 A | 12/1994 | Knighton |
| 5,375,612 A | 12/1994 | Cottenceau et al. |
| 5,385,146 A | 1/1995 | Goldreyer |
| 5,385,148 A | 1/1995 | Lesh et al. |
| 5,391,182 A | 2/1995 | Chin |
| 5,403,326 A | 4/1995 | Harrison et al. |
| 5,405,360 A | 4/1995 | Tovey |
| 5,405,376 A | 4/1995 | Mulier et al. |
| 5,409,483 A | 4/1995 | Campbell et al. |
| 5,411,016 A | 5/1995 | Kume et al. |
| 5,413,104 A | 5/1995 | Buijs et al. |
| 5,421,338 A | 6/1995 | Crowley et al. |
| 5,431,649 A | 7/1995 | Mulier et al. |
| 5,453,785 A | 9/1995 | Lenhardt et al. |
| 5,462,521 A | 10/1995 | Brucker et al. |
| 5,471,515 A | 11/1995 | Fossum et al. |
| 5,498,230 A | 3/1996 | Adair |
| 5,505,730 A | 4/1996 | Edwards |
| 5,515,853 A | 5/1996 | Smith et al. |
| 5,527,338 A | 6/1996 | Purdy |
| 5,549,603 A | 8/1996 | Feiring |
| 5,558,619 A * | 9/1996 | Kami et al. ............ 600/146 |
| 5,571,088 A | 11/1996 | Lennox et al. |
| 5,575,756 A | 11/1996 | Karasawa et al. |
| 5,575,810 A | 11/1996 | Swanson et al. |
| 5,584,872 A | 12/1996 | LaFontaine et al. |
| 5,591,119 A | 1/1997 | Adair |
| 5,593,405 A | 1/1997 | Osypka |
| 5,593,422 A | 1/1997 | Muijs Van De Moer et al. |
| 5,593,424 A | 1/1997 | Northrup, III |
| 5,643,282 A | 7/1997 | Kieturakis |
| 5,662,671 A | 9/1997 | Barbut et al. |
| 5,665,062 A | 9/1997 | Houser |
| 5,672,153 A | 9/1997 | Lax et al. |
| 5,676,693 A | 10/1997 | LaFontaine |
| 5,681,308 A | 10/1997 | Edwards et al. |
| 5,595,448 A | 12/1997 | Kimura et al. |
| 5,697,281 A | 12/1997 | Eggers et al. |
| 5,697,882 A | 12/1997 | Eggers et al. |
| 5,709,224 A | 1/1998 | Behl et al. |
| 5,713,907 A | 2/1998 | Hogendijk et al. |
| 5,713,946 A | 2/1998 | Ben-Haim |
| 5,716,321 A * | 2/1998 | Kerin et al. ............ 600/114 |
| 5,716,325 A | 2/1998 | Bonutti |

(56) References Cited

U.S. PATENT DOCUMENTS

| | | | |
|---|---|---|---|
| 5,722,403 | A | 3/1998 | McGee et al. |
| 5,725,523 | A | 3/1998 | Mueller |
| 5,743,851 | A | 4/1998 | Moll et al. |
| 5,746,747 | A | 5/1998 | McKeating |
| 5,749,846 | A | 5/1998 | Edwards et al. |
| 5,749,889 | A | 5/1998 | Bacich et al. |
| 5,749,890 | A | 5/1998 | Shaknovich |
| 5,754,313 | A | 5/1998 | Pelchy et al. |
| 5,766,137 | A | 6/1998 | Omata |
| 5,769,846 | A | 6/1998 | Edwards et al. |
| 5,792,045 | A | 8/1998 | Adair |
| 5,797,903 | A | 8/1998 | Swanson et al. |
| 5,823,947 | A | 10/1998 | Yoon et al. |
| 5,827,268 | A | 10/1998 | Laufer |
| 5,829,447 | A | 11/1998 | Stevens et al. |
| 5,842,973 | A | 12/1998 | Bullard |
| 5,843,118 | A | 12/1998 | Sepetka et al. |
| 5,846,221 | A | 12/1998 | Snoke et al. |
| 5,848,969 | A | 12/1998 | Panescu et al. |
| 5,860,974 | A | 1/1999 | Abele |
| 5,860,991 | A | 1/1999 | Klein et al. |
| 5,865,791 | A | 2/1999 | Whayne et al. |
| 5,873,815 | A | 2/1999 | Kerin et al. |
| 5,879,366 | A | 3/1999 | Shaw et al. |
| 5,895,417 | A | 4/1999 | Pomeranz et al. |
| 5,897,487 | A | 4/1999 | Ouchi |
| 5,897,553 | A | 4/1999 | Mulier et al. |
| 5,902,328 | A * | 5/1999 | LaFontaine et al. ......... 607/116 |
| 5,904,651 | A | 5/1999 | Swanson et al. |
| 5,908,445 | A | 6/1999 | Whayne et al. |
| 5,916,147 | A | 6/1999 | Boury |
| 5,925,038 | A | 7/1999 | Panescu et al. |
| 5,928,250 | A | 7/1999 | Koike et al. |
| 5,929,901 | A | 7/1999 | Adair et al. |
| 5,941,845 | A | 8/1999 | Tu et al. |
| 5,944,690 | A | 8/1999 | Falwell et al. |
| 5,964,755 | A | 10/1999 | Edwards |
| 5,968,053 | A | 10/1999 | Revelas |
| 5,971,983 | A | 10/1999 | Lesh |
| 5,980,484 | A | 11/1999 | Ressemann |
| 5,985,307 | A | 11/1999 | Hanson et al. |
| 5,986,693 | A | 11/1999 | Adair et al. |
| 5,997,571 | A | 12/1999 | Farr et al. |
| 6,004,269 | A | 12/1999 | Crowley et al. |
| 6,007,521 | A | 12/1999 | Bidwell et al. |
| 6,012,457 | A | 1/2000 | Lesh |
| 6,013,024 | A | 1/2000 | Mitsuda et al. |
| 6,024,740 | A | 2/2000 | Lesh et al. |
| 6,027,501 | A | 2/2000 | Goble et al. |
| 6,036,685 | A | 3/2000 | Mueller |
| 6,043,839 | A | 3/2000 | Adair et al. |
| 6,047,218 | A | 4/2000 | Whayne et al. |
| 6,063,077 | A | 5/2000 | Schaer |
| 6,063,081 | A | 5/2000 | Mulier et al. |
| 6,068,653 | A | 5/2000 | LaFontaine |
| 6,071,279 | A | 6/2000 | Whayne et al. |
| 6,071,302 | A | 6/2000 | Sinofsky et al. |
| 6,081,740 | A | 6/2000 | Gombrich et al. |
| 6,086,528 | A | 7/2000 | Adair |
| 6,086,534 | A | 7/2000 | Kesten |
| 6,099,498 | A | 8/2000 | Addis |
| 6,099,514 | A | 8/2000 | Sharkey et al. |
| 6,102,905 | A | 8/2000 | Baxter et al. |
| 6,112,123 | A | 8/2000 | Kelleher et al. |
| 6,115,626 | A | 9/2000 | Whayne et al. |
| 6,123,703 | A | 9/2000 | Tu et al. |
| 6,123,718 | A | 9/2000 | Tu et al. |
| 6,129,724 | A | 10/2000 | Fleischman et al. |
| 6,139,508 | A | 10/2000 | Simpson et al. |
| 6,142,993 | A | 11/2000 | Whayne et al. |
| 6,152,144 | A | 11/2000 | Lesh et al. |
| 6,156,350 | A | 12/2000 | Constantz |
| 6,159,203 | A | 12/2000 | Sinofsky |
| 6,161,543 | A | 12/2000 | Cox et al. |
| 6,164,283 | A | 12/2000 | Lesh |
| 6,167,297 | A | 12/2000 | Benaron |
| 6,168,591 | B1 | 1/2001 | Sinofsky |
| 6,168,594 | B1 | 1/2001 | LaFontaine et al. |
| 6,174,307 | B1 * | 1/2001 | Daniel et al. ................. 606/15 |
| 6,178,346 | B1 | 1/2001 | Amundson et al. |
| 6,190,381 | B1 | 2/2001 | Olsen et al. |
| 6,211,904 | B1 | 4/2001 | Adair et al. |
| 6,224,553 | B1 | 5/2001 | Neva |
| 6,231,561 | B1 | 5/2001 | Frazier et al. |
| 6,234,995 | B1 | 5/2001 | Peacock, III |
| 6,235,044 | B1 | 5/2001 | Root et al. |
| 6,237,605 | B1 | 5/2001 | Vaska et al. |
| 6,238,393 | B1 | 5/2001 | Mulier et al. |
| 6,240,312 | B1 | 5/2001 | Alfano et al. |
| 6,254,598 | B1 | 7/2001 | Edwards et al. |
| 6,258,083 | B1 | 7/2001 | Daniel et al. |
| 6,263,224 | B1 | 7/2001 | West |
| 6,266,551 | B1 | 7/2001 | Osadchy et al. |
| 6,270,492 | B1 | 8/2001 | Sinofsky |
| 6,275,255 | B1 | 8/2001 | Adair et al. |
| 6,280,450 | B1 | 8/2001 | McGuckin, Jr. |
| 6,290,689 | B1 | 9/2001 | Delaney et al. |
| 6,306,081 | B1 * | 10/2001 | Ishikawa et al. ............. 600/127 |
| 6,310,642 | B1 | 10/2001 | Adair et al. |
| 6,311,692 | B1 | 11/2001 | Vaska et al. |
| 6,314,962 | B1 | 11/2001 | Vaska et al. |
| 6,314,963 | B1 | 11/2001 | Vaska et al. |
| 6,315,777 | B1 | 11/2001 | Comben |
| 6,315,778 | B1 | 11/2001 | Gambale et al. |
| 6,322,536 | B1 | 11/2001 | Rosengart et al. |
| 6,325,797 | B1 | 12/2001 | Stewart et al. |
| 6,328,727 | B1 | 12/2001 | Frazier et al. |
| 6,358,247 | B1 | 3/2002 | Altman et al. |
| 6,358,248 | B1 | 3/2002 | Mulier et al. |
| 6,375,654 | B1 | 4/2002 | McIntyre |
| 6,379,345 | B1 | 4/2002 | Constantz |
| 6,383,195 | B1 | 5/2002 | Richard |
| 6,385,476 | B1 | 5/2002 | Osadchy et al. |
| 6,387,043 | B1 | 5/2002 | Yoon |
| 6,387,071 | B1 | 5/2002 | Constantz |
| 6,394,096 | B1 | 5/2002 | Constantz |
| 6,396,873 | B1 | 5/2002 | Goldstein et al. |
| 6,398,780 | B1 | 6/2002 | Farley et al. |
| 6,401,719 | B1 | 6/2002 | Farley et al. |
| 6,409,722 | B1 | 6/2002 | Hoey et al. |
| 6,416,511 | B1 | 7/2002 | Lesh et al. |
| 6,419,669 | B1 | 7/2002 | Frazier et al. |
| 6,423,051 | B1 | 7/2002 | Kaplan et al. |
| 6,423,055 | B1 | 7/2002 | Farr et al. |
| 6,423,058 | B1 | 7/2002 | Edwards et al. |
| 6,428,536 | B2 | 8/2002 | Panescu et al. |
| 6,436,118 | B1 | 8/2002 | Kayan |
| 6,440,061 | B1 | 8/2002 | Wenner et al. |
| 6,440,119 | B1 | 8/2002 | Nakada et al. |
| 6,458,151 | B1 | 10/2002 | Saltiel |
| 6,461,327 | B1 | 10/2002 | Addis et al. |
| 6,464,697 | B1 | 10/2002 | Edwards et al. |
| 6,474,340 | B1 | 11/2002 | Vaska et al. |
| 6,475,223 | B1 | 11/2002 | Werp et al. |
| 6,478,769 | B1 | 11/2002 | Parker |
| 6,482,162 | B1 | 11/2002 | Moore |
| 6,484,727 | B1 | 11/2002 | Vaska et al. |
| 6,485,489 | B2 | 11/2002 | Teirstein et al. |
| 6,488,671 | B1 | 12/2002 | Constantz et al. |
| 6,494,902 | B2 | 12/2002 | Hoey et al. |
| 6,497,651 | B1 | 12/2002 | Kan et al. |
| 6,497,705 | B2 | 12/2002 | Comben |
| 6,500,174 | B1 | 12/2002 | Maguire et al. |
| 6,502,576 | B1 | 1/2003 | Lesh |
| 6,572,609 | B1 | 1/2003 | Farr et al. |
| 6,514,249 | B1 | 2/2003 | Maguire et al. |
| 6,517,533 | B1 | 2/2003 | Swaminathan |
| 6,527,979 | B2 | 3/2003 | Constantz |
| 6,532,380 | B1 | 3/2003 | Close et al. |
| 6,533,767 | B2 | 3/2003 | Johansson et al. |
| 6,537,272 | B2 | 3/2003 | Christopherson et al. |
| 6,540,733 | B2 | 4/2003 | Constantz et al. |
| 6,540,744 | B2 | 4/2003 | Hassett et al. |
| 6,544,195 | B2 | 4/2003 | Wilson et al. |

(56) References Cited

U.S. PATENT DOCUMENTS

| | | | |
|---|---|---|---|
| 6,547,780 B1 | 4/2003 | Sinofsky | |
| 6,549,800 B1 | 4/2003 | Atalar et al. | |
| 6,558,375 B1 | 5/2003 | Sinofsky et al. | |
| 6,558,382 B2 | 5/2003 | Jahns et al. | |
| 6,562,020 B1 | 5/2003 | Constantz et al. | |
| 6,579,285 B2 | 6/2003 | Sinofsky | |
| 6,585,732 B2 | 7/2003 | Mulier et al. | |
| 6,587,709 B2 | 7/2003 | Solf et al. | |
| 6,593,884 B1 | 7/2003 | Gilboa et al. | |
| 6,605,055 B1 | 8/2003 | Sinofsky et al. | |
| 6,613,062 B1 | 9/2003 | Leckrone et al. | |
| 6,622,732 B2 | 9/2003 | Constantz | |
| 6,626,855 B1 | 9/2003 | Weng et al. | |
| 6,626,899 B2 | 9/2003 | Houser et al. | |
| 6,626,900 B1 | 9/2003 | Sinofsky et al. | |
| 6,635,070 B2 | 10/2003 | Leeflang et al. | |
| 6,645,202 B1 | 11/2003 | Pless et al. | |
| 6,650,923 B1 | 11/2003 | Lesh et al. | |
| 6,658,279 B2 | 12/2003 | Swanson et al. | |
| 6,659,940 B2 | 12/2003 | Adler | |
| 6,673,090 B2 | 1/2004 | Root et al. | |
| 6,676,656 B2 | 1/2004 | Sinofsky | |
| 6,679,836 B2 | 1/2004 | Couvillon, Jr. | |
| 6,682,526 B1 | 1/2004 | Jones et al. | |
| 6,689,051 B2 | 2/2004 | Nakada et al. | |
| 6,689,128 B2 | 2/2004 | Sliwa, Jr. et al. | |
| 6,692,430 B2 | 2/2004 | Adler | |
| 6,701,581 B2 | 3/2004 | Senovich et al. | |
| 6,701,931 B2 | 3/2004 | Sliwa, Jr. et al. | |
| 6,702,780 B1 | 3/2004 | Gilboa et al. | |
| 6,704,043 B2 | 3/2004 | Goldstein et al. | |
| 6,706,039 B2 | 3/2004 | Mulier et al. | |
| 6,712,798 B2 | 3/2004 | Constantz | |
| 6,719,747 B2 | 4/2004 | Constantz et al. | |
| 6,719,755 B2 | 4/2004 | Sliwa, Jr. et al. | |
| 6,730,063 B2 | 5/2004 | Delaney et al. | |
| 6,736,810 B2 | 5/2004 | Hoey et al. | |
| 6,749,617 B1 | 6/2004 | Palasis et al. | |
| 6,751,492 B2 | 6/2004 | Ben-Haim | |
| 6,755,790 B2 | 6/2004 | Stewart et al. | |
| 6,755,811 B1 | 6/2004 | Constantz | |
| 6,764,487 B2 | 7/2004 | Mulier et al. | |
| 6,770,070 B1 | 8/2004 | Balbierz | |
| 6,771,996 B2 | 8/2004 | Bowe et al. | |
| 6,773,402 B2 | 8/2004 | Govari et al. | |
| 6,780,151 B2 | 8/2004 | Grabover et al. | |
| 6,805,128 B1 | 10/2004 | Pless et al. | |
| 6,805,129 B1 | 10/2004 | Pless et al. | |
| 6,811,562 B1 | 11/2004 | Pless | |
| 6,833,814 B2 | 12/2004 | Gilboa et al. | |
| 6,840,923 B1 | 1/2005 | Lapcevic | |
| 6,840,936 B2 | 1/2005 | Sliwa, Jr. et al. | |
| 6,849,073 B2 | 2/2005 | Hoey et al. | |
| 6,858,005 B2 | 2/2005 | Ohline et al. | |
| 6,858,026 B2 | 2/2005 | Sliwa, Jr. et al. | |
| 6,858,905 B2 | 2/2005 | Hsu et al. | |
| 6,863,668 B2 | 3/2005 | Gillespie et al. | |
| 6,866,651 B2 | 3/2005 | Constantz | |
| 6,887,237 B2 | 5/2005 | McGaffigan | |
| 6,892,091 B1 | 5/2005 | Ben-Haim et al. | |
| 6,896,690 B1 | 5/2005 | Lambrecht et al. | |
| 6,899,672 B2 | 5/2005 | Chin et al. | |
| 6,915,154 B1 | 7/2005 | Docherty et al. | |
| 6,916,284 B2* | 7/2005 | Moriyama | 600/127 |
| 6,916,286 B2 | 7/2005 | Kazakevich | |
| 6,923,805 B1 | 8/2005 | LaFontaine et al. | |
| 6,929,010 B2 | 8/2005 | Vaska et al. | |
| 6,932,809 B2 | 8/2005 | Sinofsky | |
| 6,939,348 B2 | 9/2005 | Malecki et al. | |
| 6,942,657 B2 | 9/2005 | Sinofsky et al. | |
| 6,949,095 B2 | 9/2005 | Vaska et al. | |
| 6,953,457 B2 | 10/2005 | Farr et al. | |
| 6,955,173 B2 | 10/2005 | Lesh | |
| 6,958,069 B2 | 10/2005 | Shipp et al. | |
| 6,962,589 B2 | 11/2005 | Mulier et al. | |
| 6,971,394 B2 | 12/2005 | Sliwa, Jr. et al. | |
| 6,974,464 B2 | 12/2005 | Quijano et al. | |
| 6,979,290 B2* | 12/2005 | Mourlas et al. | 600/115 |
| 6,982,740 B2 | 1/2006 | Adair et al. | |
| 6,984,232 B2 | 1/2006 | Vanney et al. | |
| 6,994,094 B2 | 2/2006 | Schwartz | |
| 7,019,610 B2 | 3/2006 | Creighton, IV et al. | |
| 7,025,746 B2* | 4/2006 | Tal | 604/164.1 |
| 7,030,904 B2 | 4/2006 | Adair et al. | |
| 7,041,098 B2 | 5/2006 | Farley et al. | |
| 7,042,487 B2 | 5/2006 | Nakashima | |
| 7,044,135 B2 | 5/2006 | Lesh | |
| 7,052,493 B2 | 5/2006 | Vaska et al. | |
| 7,090,683 B2 | 8/2006 | Brock et al. | |
| 7,118,566 B2 | 10/2006 | Jahns | |
| 7,156,845 B2 | 1/2007 | Mulier et al. | |
| 7,163,534 B2 | 1/2007 | Brucker et al. | |
| 7,166,537 B2 | 1/2007 | Jacobsen et al. | |
| 7,169,144 B2 | 1/2007 | Hoey et al. | |
| 7,179,224 B2 | 2/2007 | Willis | |
| 7,186,214 B2 | 3/2007 | Ness | |
| 7,207,984 B2 | 4/2007 | Farr et al. | |
| 7,217,268 B2 | 5/2007 | Eggers et al. | |
| 7,242,832 B2 | 7/2007 | Carlin et al. | |
| 7,247,155 B2 | 7/2007 | Hoey et al. | |
| 7,261,711 B2 | 8/2007 | Mulier et al. | |
| 7,263,397 B2 | 8/2007 | Hauck et al. | |
| 7,276,061 B2 | 10/2007 | Schaer et al. | |
| 7,309,328 B2 | 12/2007 | Kaplan et al. | |
| 7,322,934 B2 | 1/2008 | Miyake et al. | |
| 7,323,001 B2 | 1/2008 | Clubb et al. | |
| 7,416,552 B2 | 8/2008 | Paul et al. | |
| 7,435,248 B2 | 10/2008 | Taimisto et al. | |
| 7,527,625 B2 | 5/2009 | Knight et al. | |
| 7,534,204 B2 | 5/2009 | Starksen et al. | |
| 7,534,294 B1 | 5/2009 | Gaynor et al. | |
| 7,569,052 B2* | 8/2009 | Phan et al. | 606/35 |
| 7,569,952 B1 | 8/2009 | Bono et al. | |
| 7,736,347 B2 | 6/2010 | Kaplan et al. | |
| 7,758,499 B2 | 7/2010 | Adler | |
| 7,860,555 B2 | 12/2010 | Saadat | |
| 7,860,556 B2 | 12/2010 | Saadat | |
| 7,918,787 B2 | 4/2011 | Saadat | |
| 7,919,610 B2 | 4/2011 | Serebriiskii et al. | |
| 7,930,016 B1 | 4/2011 | Saadat | |
| 8,050,746 B2 | 11/2011 | Saadat et al. | |
| 8,078,266 B2 | 12/2011 | Saadat et al. | |
| 8,131,350 B2 | 3/2012 | Saadat et al. | |
| 8,137,333 B2 | 3/2012 | Saadat et al. | |
| 8,221,310 B2 | 7/2012 | Saadat et al. | |
| 8,235,985 B2 | 8/2012 | Saadat et al. | |
| 8,333,012 B2 | 12/2012 | Rothe et al. | |
| 8,417,321 B2 | 4/2013 | Saadat et al. | |
| 8,419,613 B2 | 4/2013 | Saadat et al. | |
| 8,657,805 B2 | 2/2014 | Peh et al. | |
| 8,758,229 B2 | 6/2014 | Saadat et al. | |
| 8,814,845 B2 | 8/2014 | Saadat et al. | |
| 8,934,962 B2 | 1/2015 | Saadat et al. | |
| 9,055,906 B2 | 6/2015 | Saadat et al. | |
| 9,192,287 B2 | 11/2015 | Saadat et al. | |
| 9,226,648 B2 | 1/2016 | Saadat et al. | |
| 9,332,893 B2 | 5/2016 | Saadat et al. | |
| 9,510,732 B2 | 12/2016 | Miller et al. | |
| 9,526,401 B2 | 12/2016 | Saadat et al. | |
| 2001/0005789 A1 | 6/2001 | Root et al. | |
| 2001/0020126 A1 | 9/2001 | Swanson et al. | |
| 2001/0031912 A1 | 10/2001 | Adler | |
| 2001/0039416 A1 | 11/2001 | Moorman et al. | |
| 2001/0047136 A1 | 11/2001 | Domanik et al. | |
| 2001/0047184 A1 | 11/2001 | Connors | |
| 2001/0052930 A1 | 12/2001 | Adair et al. | |
| 2002/0004644 A1 | 1/2002 | Koblish | |
| 2002/0026145 A1 | 2/2002 | Bagaoisan et al. | |
| 2002/0035311 A1 | 3/2002 | Ouchi | |
| 2002/0054852 A1 | 5/2002 | Cate | |
| 2002/0065455 A1 | 5/2002 | Ben-Haim et al. | |
| 2002/0068853 A1 | 6/2002 | Adler et al. | |
| 2002/0077642 A1 | 6/2002 | Patel et al. | |
| 2002/0080248 A1 | 6/2002 | Adair et al. | |

(56) References Cited

U.S. PATENT DOCUMENTS

| | | |
|---|---|---|
| 2002/0087166 A1 | 7/2002 | Brock et al. |
| 2002/0087169 A1 | 7/2002 | Brock et al. |
| 2002/0091304 A1 | 7/2002 | Takeshi et al. |
| 2002/0138088 A1 | 9/2002 | Nash et al. |
| 2002/0161377 A1 | 10/2002 | Rabkin et al. |
| 2002/0165598 A1 | 11/2002 | Wahr et al. |
| 2002/0169377 A1 | 11/2002 | Khairkhahan et al. |
| 2003/0009085 A1* | 1/2003 | Arai et al. .................. 600/127 |
| 2003/0014010 A1 | 1/2003 | Carpenter et al. |
| 2003/0018358 A1 | 1/2003 | Saadat |
| 2003/0035156 A1 | 2/2003 | Cooper |
| 2003/0036698 A1 | 2/2003 | Kohler et al. |
| 2003/0065267 A1 | 4/2003 | Smith |
| 2003/0069593 A1 | 4/2003 | Tremulis et al. |
| 2003/0120142 A1 | 6/2003 | Dubuc et al. |
| 2003/0130572 A1 | 7/2003 | Phan et al. |
| 2003/0144657 A1 | 7/2003 | Bowe et al. |
| 2003/0171741 A1 | 9/2003 | Ziebol et al. |
| 2003/0181939 A1 | 9/2003 | Bonutti |
| 2003/0208222 A1 | 11/2003 | Zadno-Azizi |
| 2003/0212394 A1 | 11/2003 | Pearson et al. |
| 2003/0216720 A1 | 11/2003 | Sinofsky et al. |
| 2003/0220574 A1 | 11/2003 | Markus et al. |
| 2003/0222325 A1 | 12/2003 | Jacobsen et al. |
| 2003/0236493 A1 | 12/2003 | Mauch |
| 2004/0006333 A1 | 1/2004 | Arnold et al. |
| 2004/0044350 A1 | 3/2004 | Martin et al. |
| 2004/0049211 A1 | 3/2004 | Tremulis et al. |
| 2004/0054335 A1 | 3/2004 | Lesh et al. |
| 2004/0054389 A1 | 3/2004 | Osypka |
| 2004/0082833 A1 | 4/2004 | Adler |
| 2004/0097788 A1 | 5/2004 | Mourlas et al. |
| 2004/0097792 A1 | 5/2004 | Moll et al. |
| 2004/0098031 A1 | 5/2004 | Van Der Burg et al. |
| 2004/0117032 A1 | 6/2004 | Roth |
| 2004/0133113 A1 | 7/2004 | Krishnan |
| 2004/0138707 A1 | 7/2004 | Greenhalgh |
| 2004/0147806 A1 | 7/2004 | Adler |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0158143 A1 | 8/2004 | Flaherty et al. |
| 2004/0158289 A1 | 8/2004 | Girouard et al. |
| 2004/0165766 A1 | 8/2004 | Goto |
| 2004/0167503 A1 | 8/2004 | Sinofsky |
| 2004/0181237 A1 | 9/2004 | Forde et al. |
| 2004/0199052 A1 | 10/2004 | Banik et al. |
| 2004/0210111 A1 | 10/2004 | Okada |
| 2004/0210239 A1 | 10/2004 | Nash et al. |
| 2004/0215180 A1 | 10/2004 | Starkebaum et al. |
| 2004/0215183 A1 | 10/2004 | Hoey et al. |
| 2004/0220471 A1 | 11/2004 | Schwartz |
| 2004/0230131 A1 | 11/2004 | Kassab et al. |
| 2004/0248837 A1 | 12/2004 | Raz et al. |
| 2004/0249367 A1 | 12/2004 | Saadat et al. |
| 2004/0254523 A1 | 12/2004 | Fitzgerald et al. |
| 2004/0260182 A1 | 12/2004 | Zuluaga et al. |
| 2005/0014995 A1 | 1/2005 | Amundson et al. |
| 2005/0015048 A1 | 1/2005 | Chiu et al. |
| 2005/0020914 A1 | 1/2005 | Amundson et al. |
| 2005/0027163 A1 | 2/2005 | Chin et al. |
| 2005/0038419 A9 | 2/2005 | Arnold et al. |
| 2005/0059862 A1 | 3/2005 | Phan |
| 2005/0059954 A1 | 3/2005 | Constantz |
| 2005/0059965 A1 | 3/2005 | Eberl et al. |
| 2005/0059984 A1 | 3/2005 | Chanduszko et al. |
| 2005/0065504 A1 | 3/2005 | Melsky et al. |
| 2005/0090818 A1 | 4/2005 | Pike, Jr. et al. |
| 2005/0096502 A1 | 5/2005 | Khalili |
| 2005/0096643 A1 | 5/2005 | Brucker et al. |
| 2005/0101984 A1 | 5/2005 | Chanduszko et al. |
| 2005/0107736 A1 | 5/2005 | Landman et al. |
| 2005/0119523 A1 | 6/2005 | Starksen et al. |
| 2005/0124969 A1 | 6/2005 | Fitzgerald et al. |
| 2005/0131401 A1 | 6/2005 | Malecki et al. |
| 2005/0154252 A1 | 7/2005 | Sharkey et al. |
| 2005/0158899 A1 | 7/2005 | Jacobsen et al. |
| 2005/0159702 A1 | 7/2005 | Sekiguchi et al. |
| 2005/0165279 A1 | 7/2005 | Adler et al. |
| 2005/0165391 A1 | 7/2005 | Maguire et al. |
| 2005/0165466 A1 | 7/2005 | Morris et al. |
| 2005/0182465 A1 | 8/2005 | Ness |
| 2005/0197530 A1 | 9/2005 | Wallace et al. |
| 2005/0197623 A1 | 9/2005 | Leeflang et al. |
| 2005/0215895 A1 | 9/2005 | Popp et al. |
| 2005/0222554 A1 | 10/2005 | Wallace et al. |
| 2005/0222557 A1 | 10/2005 | Baxter et al. |
| 2005/0222558 A1 | 10/2005 | Baxter et al. |
| 2005/0228452 A1 | 10/2005 | Mourlas et al. |
| 2005/0234436 A1 | 10/2005 | Baxter et al. |
| 2005/0234437 A1 | 10/2005 | Baxter et al. |
| 2005/0267328 A1 | 12/2005 | Blumzvig et al. |
| 2005/0267452 A1 | 12/2005 | Farr et al. |
| 2006/0009715 A1 | 1/2006 | Khairkhahan et al. |
| 2006/0009737 A1 | 1/2006 | Whiting et al. |
| 2006/0015096 A1 | 1/2006 | Hauck et al. |
| 2006/0022234 A1 | 2/2006 | Adair et al. |
| 2006/0025651 A1 | 2/2006 | Adler et al. |
| 2006/0025787 A1 | 2/2006 | Morales et al. |
| 2006/0030844 A1 | 2/2006 | Knight et al. |
| 2006/0069303 A1 | 3/2006 | Couvillon et al. |
| 2006/0074398 A1 | 4/2006 | Whiting et al. |
| 2006/0084839 A1 | 4/2006 | Mourlas et al. |
| 2006/0084945 A1 | 4/2006 | Moll et al. |
| 2006/0089637 A1 | 4/2006 | Werneth et al. |
| 2006/0111614 A1 | 5/2006 | Saadat et al. |
| 2006/0122587 A1 | 6/2006 | Sharareh |
| 2006/0146172 A1 | 7/2006 | Jacobsen et al. |
| 2006/0149129 A1 | 7/2006 | Watts et al. |
| 2006/0149331 A1 | 7/2006 | Mann et al. |
| 2006/0155242 A1 | 7/2006 | Constantz |
| 2006/0161133 A1 | 7/2006 | Laird et al. |
| 2006/0167439 A1 | 7/2006 | Kaiser et al. |
| 2006/0183992 A1 | 8/2006 | Kawashima |
| 2006/0184048 A1 | 8/2006 | Saadat |
| 2006/0217755 A1 | 9/2006 | Eversull et al. |
| 2006/0224167 A1 | 10/2006 | Weisenburgh et al. |
| 2006/0253113 A1 | 11/2006 | Arnold et al. |
| 2006/0258909 A1 | 11/2006 | Saadat et al. |
| 2006/0271032 A1 | 11/2006 | Chin et al. |
| 2007/0005019 A1 | 1/2007 | Okishige |
| 2007/0015964 A1 | 1/2007 | Eversull et al. |
| 2007/0016130 A1 | 1/2007 | Leeflang et al. |
| 2007/0043338 A1 | 2/2007 | Moll et al. |
| 2007/0043413 A1 | 2/2007 | Eversull et al. |
| 2007/0049923 A1 | 3/2007 | Jahns |
| 2007/0055142 A1 | 3/2007 | Webler |
| 2007/0078451 A1 | 4/2007 | Arnold et al. |
| 2007/0083187 A1 | 4/2007 | Eversull et al. |
| 2007/0083217 A1 | 4/2007 | Eversull et al. |
| 2007/0093808 A1 | 4/2007 | Mulier et al. |
| 2007/0100241 A1 | 5/2007 | Adler |
| 2007/0100324 A1 | 5/2007 | Tempel et al. |
| 2007/0106146 A1 | 5/2007 | Claudio et al. |
| 2007/0106214 A1 | 5/2007 | Gray et al. |
| 2007/0106287 A1 | 5/2007 | O'Sullivan |
| 2007/0135826 A1 | 6/2007 | Zaver et al. |
| 2007/0167801 A1 | 7/2007 | Webler et al. |
| 2007/0167828 A1 | 7/2007 | Saadat |
| 2007/0239010 A1 | 10/2007 | Johnson |
| 2007/0265609 A1 | 11/2007 | Thapliyal et al. |
| 2007/0265610 A1 | 11/2007 | Thapliyal et al. |
| 2007/0270639 A1 | 11/2007 | Long |
| 2007/0270686 A1 | 11/2007 | Ritter et al. |
| 2007/0282371 A1 | 12/2007 | Lee et al. |
| 2007/0287886 A1 | 12/2007 | Saadat |
| 2007/0293724 A1 | 12/2007 | Saadat et al. |
| 2008/0009747 A1 | 1/2008 | Saadat et al. |
| 2008/0009859 A1 | 1/2008 | Auth et al. |
| 2008/0015445 A1 | 1/2008 | Saadat et al. |
| 2008/0015563 A1 | 1/2008 | Hoey et al. |
| 2008/0015569 A1 | 1/2008 | Saadat et al. |
| 2008/0027464 A1 | 1/2008 | Moll et al. |
| 2008/0033241 A1 | 2/2008 | Peh et al. |

(56) References Cited

U.S. PATENT DOCUMENTS

| | | |
|---|---|---|
| 2008/0033290 A1 | 2/2008 | Saadat et al. |
| 2008/0057106 A1 | 3/2008 | Erickson et al. |
| 2008/0058590 A1 | 3/2008 | Saadat et al. |
| 2008/0058650 A1 | 3/2008 | Saadat et al. |
| 2008/0058836 A1 | 3/2008 | Moll et al. |
| 2008/0097476 A1 | 4/2008 | Peh et al. |
| 2008/0183081 A1 | 7/2008 | Lys et al. |
| 2008/0188759 A1 | 8/2008 | Saadat et al. |
| 2008/0214889 A1 | 9/2008 | Saadat et al. |
| 2008/0228032 A1 | 9/2008 | Starksen et al. |
| 2008/0275300 A1 | 11/2008 | Rothe et al. |
| 2008/0281293 A1 | 11/2008 | Peh et al. |
| 2008/0287790 A1 | 11/2008 | Li |
| 2008/0287805 A1 | 11/2008 | Li |
| 2009/0030276 A1 | 1/2009 | Saadat et al. |
| 2009/0030412 A1 | 1/2009 | Willis et al. |
| 2009/0048480 A1 | 2/2009 | Klenk et al. |
| 2009/0054803 A1 | 2/2009 | Saadat et al. |
| 2009/0062790 A1 | 3/2009 | Malchano et al. |
| 2009/0076489 A1 | 3/2009 | Welches et al. |
| 2009/0076498 A1 | 3/2009 | Saadat et al. |
| 2009/0082623 A1 | 3/2009 | Rothe et al. |
| 2009/0125022 A1 | 5/2009 | Saadat et al. |
| 2009/0143640 A1 | 6/2009 | Saadat et al. |
| 2009/0187074 A1 | 7/2009 | Saadat et al. |
| 2009/0203962 A1 | 8/2009 | Miller et al. |
| 2009/0221871 A1 | 9/2009 | Peh et al. |
| 2009/0227999 A1 | 9/2009 | Willis et al. |
| 2009/0264727 A1 | 10/2009 | Markowitz et al. |
| 2009/0267773 A1 | 10/2009 | Markowitz et al. |
| 2009/0275799 A1 | 11/2009 | Saadat et al. |
| 2009/0275842 A1 | 11/2009 | Saadat et al. |
| 2009/0299363 A1 | 12/2009 | Saadat et al. |
| 2009/0326572 A1 | 12/2009 | Peh et al. |
| 2010/0004506 A1 | 1/2010 | Saadat |
| 2010/0004633 A1 | 1/2010 | Rothe et al. |
| 2010/0004661 A1 | 1/2010 | Verin et al. |
| 2010/0010311 A1 | 1/2010 | Miller et al. |
| 2010/0094081 A1 | 4/2010 | Rothe et al. |
| 2010/0130836 A1 | 5/2010 | Malchano et al. |
| 2010/0292558 A1 | 11/2010 | Saadat et al. |
| 2011/0060227 A1 | 3/2011 | Saadat |
| 2011/0060298 A1 | 3/2011 | Saadat |
| 2011/0144576 A1 | 6/2011 | Rothe et al. |
| 2012/0016221 A1 | 1/2012 | Saadat et al. |
| 2012/0059366 A1 | 3/2012 | Drews et al. |
| 2012/0150046 A1 | 6/2012 | Watson et al. |
| 2013/0023731 A1 | 1/2013 | Saadat et al. |
| 2013/0131448 A1 | 5/2013 | Saadat et al. |
| 2014/0012074 A1 | 1/2014 | Vazales et al. |
| 2014/0114129 A1 | 4/2014 | Peh et al. |
| 2014/0350412 A1 | 11/2014 | Saadat et al. |
| 2015/0094577 A1 | 4/2015 | Saadat et al. |
| 2015/0190036 A1 | 7/2015 | Saadat |
| 2015/0250382 A1 | 9/2015 | Saadat et al. |
| 2016/0038005 A1 | 2/2016 | Saadat et al. |
| 2016/0096601 A1 | 4/2016 | Hollis |
| 2016/0227989 A1 | 8/2016 | Saadat et al. |
| 2017/0071460 A1 | 3/2017 | Miller et al. |

FOREIGN PATENT DOCUMENTS

| | | |
|---|---|---|
| EP | 0283661 | 9/1988 |
| EP | 0842673 A1 | 5/1998 |
| EP | 0301288 A1 | 2/1999 |
| JP | 59093413 A | 5/1984 |
| JP | 59-181315 | 10/1984 |
| JP | 01-221133 | 9/1989 |
| JP | 03-284265 | 12/1991 |
| JP | 05-103746 | 4/1993 |
| JP | H06507809 A | 9/1994 |
| JP | 09-051897 | 2/1997 |
| JP | 11-299725 | 11/1999 |
| JP | 2001504363 A | 4/2001 |
| JP | 2001-258822 | 9/2001 |
| WO | WO 1992/21292 | 12/1992 |
| WO | WO 1994/07413 | 4/1994 |
| WO | WO 1995/03843 | 2/1995 |
| WO | WO-9740880 A1 | 11/1997 |
| WO | WO 1998/18388 | 5/1998 |
| WO | WO-0024310 A1 | 5/2000 |
| WO | WO-0149356 A1 | 7/2001 |
| WO | WO-0172368 A2 | 10/2001 |
| WO | WO-0230310 A1 | 4/2002 |
| WO | WO 2003/039350 | 5/2003 |
| WO | WO-03037416 A1 | 5/2003 |
| WO | WO 2003/053491 | 7/2003 |
| WO | WO-03073942 A2 | 9/2003 |
| WO | WO 2003/101287 | 12/2003 |
| WO | WO 2004/043272 | 5/2004 |
| WO | WO 2004/080508 | 9/2004 |
| WO | WO 2005/070330 | 8/2005 |
| WO | WO 2005/077435 | 8/2005 |
| WO | WO 2005/081202 | 9/2005 |
| WO | WO 2006/017517 | 2/2006 |
| WO | WO 2006/024015 | 3/2006 |
| WO | WO 2006/083794 | 8/2006 |
| WO | WO 2006/091597 | 8/2006 |
| WO | WO 2006/126979 | 11/2006 |
| WO | WO 2007/067323 | 6/2007 |
| WO | WO 2007/079268 | 7/2007 |
| WO | WO 2007/133845 | 11/2007 |
| WO | WO 2007/134258 | 11/2007 |
| WO | WO 2008/015625 | 2/2008 |
| WO | WO 2008/021994 | 2/2008 |
| WO | WO 2008/021997 | 2/2008 |
| WO | WO 2008/021998 | 2/2008 |
| WO | WO 2008/024261 | 2/2008 |
| WO | WO 2008/079828 | 7/2008 |
| WO | WO 2009/112262 | 9/2009 |

OTHER PUBLICATIONS

Avitall, Right-Sided Driven Atrial Fibrillation in a Sterile Pericarditis Dog Model, PACE, vol. 17, p. 774, 1994.

Avitall, Vagally Mediated Atrial Fibrillation in a Dog Model can be Ablated by Placing Linear Radiofrequency Lesions at the Junction of the Right Atrial Appendage and the Superior Vena Cava, PACE, vol. 18, p. 857, 1995.

Baker, Nonpharmacologic Approaches to the Treatment of Atrial Fibrillation and Atrial Flutter, J. Cardiovasc. Electrophysiol., vol. 6, pp. 972-978, 1995.

Bhakta, Principles of Electroanatomic Mapping, Indian Pacing & Electrophysiol J., vol. 8, No. 1, pp. 32-50, 2008.

Bidoggia, Transseptal Left Heart Catheterization: Usefulness of the Intracavitary Electrocardiogram in the Localization of the Fossa Ovalis, Cathet Cardiovasc Diagn., vol. 24, No. 3, pp. 221-225, 1991.

Bredikis, Surgery of Tachyarrhythmia: Intracardiac Closed Heart Cryoablation, PACE, vol. 13, pp. 1980-1984, 1990.

Cox, Cardiac Surgery for Arrhythmias, J. Cardiovasc. Electrophysiol., vol. 15, pp. 250-262, 2004.

Cox, Five-Year Experience With the Maze Procedure for Atrial Fibrillation, Ann. Thorac. Surg., vol. 56, pp. 814-824, 1993.

Cox, Modification of the Maze Procedure for Atrial Flutter and Atrial Fibrillation, J. Thorac. Cardiovasc. Surg., vol. 110, pp. 473-484, 1995.

Cox, The Status of Surgery for Cardiac Arrhythmias, Circulation, vol. 71, pp. 413-417, 1985.

Cox, The Surgical Treatment of Atrial Fibrillation, J. Thorac Cardiovasc. Surg., vol. 101, pp. 584-592, 1991.

Elvan, Replication of the "Maze" Procedure by Radiofrequency Catheter Ablation Reduces the Ability to Induce Atrial Fibrillation, PACE, vol. 17, p. 774, 1994.

Elvan, Radiofrequency Catheter Ablation (RFCA) of the Atria Effectively Abolishes Pacing Induced Chronic Atrial Fibrillation, PACE, vol. 18, p. 856, 1995.

Elvan, Radiofrequency Catheter Ablation of the Atria Reduces Inducibility and Duration of Atrial Fibrillation in Dogs, Circulation, vol. 91, pp. 2235-2244, 1995.

(56) References Cited

OTHER PUBLICATIONS

European Patent Application No. 06734083.6 filed Jan. 30, 2006 in the name of Saadat et al., extended European Search Report dated Jul. 1, 2009.
European Patent Application No. 06734083.6 filed Jan. 30, 2006 in the name of Saadat et al., office action dated Oct. 23, 2009.
Fieguth, Inhibition of Atrial Fibrillation by Pulmonary Vein Isolation and Auricular Resection—Experimental Study in a Sheep Model, European J. Cardiothorac. Surg., vol. 11, pp. 714-721, 1997.
Hoey, Intramural Ablation Using Radiofrequency Energy Via Screw-Tip Catheter and Saline Electrode, PACE, vol. 18, p. 487, 1995.
Huang, Increase in the Lesion Size and Decrease in the Impedance Rise with a Saline Infusion Electrode Catheter for Radiofrequency, Circulation, vol. 80, No. 4, pp. II-324, 1989.
Moser, Angioscopic Visualization of Pulmonary Emboli, Chest, vol. 77, No. 2, pp. 198-201, 1980.
Nakamura, Percutaneous Intracardiac Surgery With Cardioscopic Guidance, SPIE, vol. 1652, pp. 214-216, 1992.
Pappone, Circumferential Radiofrequency Ablation of Pulmonary Vein Ostia, Circulation, vol. 102, pp. 2619-2628, 2000.
Sethi, Transseptal Catheterization for the Electrophysiologist: Modification with a "View", J. Interv. Card. Electrophysiol., vol. 5, pp. 97-99, 2001, Kluwer Academic Publishers, Netherlands.
Thiagalingam, Cooled Needle Catheter Ablation Creates Deeper and Wider Lesions than Irrigated Tip Catheter Ablation, J. Cardiovasc. Electrophysiol., vol. 16, pp. 1-8, 2005.
U.S. Appl. No. 11/828,267, filed Jul. 25, 2007 in the name of Saadat et al., Non-final Office Action dated Jan. 14, 2010.
U.S. Appl. No. 12/117,655, filed May 8, 2008 in the name of Saadat et al., Non-final Office Action dated Jun. 8, 2009.
Willkampf, Radiofrequency Ablation with a Cooled Porous Electrode Catheter, JACC, vol. 11, No. 2, p. 17A, 1988.
U.S. Appl. No. 11/775,771, filed Jul. 10, 2007 in the name of Saadat et al., Non-final Office Action dated Aug. 27, 2010.
U.S. Appl. No. 11/828,267, filed Jul. 25, 2007 in the name of Saadat et al., final Office Action dated Sep. 16, 2010.
U.S. Appl. No. 11/259,498, filed Oct. 25, 2005 in the name of Saadat, Notice of Allowance dated Nov. 15, 2010.
U.S. Appl. No. 11/560,742, filed Nov. 16, 2006 in the name of Saadat, Notice of Allowance dated Nov. 15, 2010.
U.S. Appl. No. 12/464,800, filed May 12, 2009 in the name of Peh et al., non-final Office Action dated Nov. 24, 2010.
U.S. Appl. No. 11/848,429, filed Aug. 31, 2007 in the name of Peh et al., non-final Office Action dated Nov. 24, 2010.
European Patent Application No. 07812146.4 filed Jun. 14, 2007 in the name of Voyage Medical, Inc., European Search Report dated Nov. 18, 2010.
European Patent Application No. 07799466.3 filed Jul. 10, 2007 in the name of Voyage Medical, Inc., European Search Report dated Nov. 18, 2010.
U.S. Appl. No. 12/117,655, filed May 8, 2008 in the name of Peh et al., non-final Office Action dated Dec. 16, 2010.
U.S. Appl. No. 11/560,732, filed Nov. 16, 2006 in the name of Saadat, Notice of Allowance dated Feb. 3, 2011.
U.S. Appl. No. 12/026,455, filed Feb. 5, 2008 in the name of Saadat et al., non-final Office Action dated Dec. 27, 2010.
European Patent Application No. 06734083.6 filed Jan. 30, 2006 in the name of Voyage Medical, Inc., Office Action dated Nov. 12, 2010.
U.S. Appl. No. 12/947,198, filed Nov. 16, 2010 in the name of Saadat, non-final Office Action dated Feb. 18, 2011.
U.S. Appl. No. 12/947,246, filed Nov. 16, 2006 in the name of Saadat, non-final Office Action dated Feb. 18, 2011.
U.S. Appl. No. 11/687,597, filed Mar. 16, 2007 in the name of Saadat, Notice of Allowance dated Feb. 24, 2011.
U.S. Appl. No. 11/560,732, filed Mar. 16, 2007 in the name of Saadat, Notice of Allowance dated Feb. 24, 2011.
U.S. Appl. No. 11/848,207, filed Aug. 30, 2007 in the name of Saadat et al., non-final Office Action dated Feb. 25, 2011.
Japanese Patent Application No. 2007-554156 filed Jan. 30, 2006 in the name of Voyage Medical, Inc., Office Action dated Feb. 15, 2011.
European Patent Application No. 07758716.0 filed Mar. 16, 2007 in the name of Voyage Medical, Inc., Supplemental European Search Report dated Feb. 28, 2011.
U.S. Appl. No. 11/848,202, filed Aug. 30, 2007 in the name of Saadat et al., non-final Office Action dated Mar. 11, 2011.
U.S. Appl. No. 12/499,011, filed Jul. 7, 2009 in the name of Rothe et al., non-final Office Action dated Apr. 12, 2011.
U.S. Appl. No. 12/367,019, filed Feb. 6, 2009 in the name of Miller et al., non-final Office Action dated Apr. 22, 2011.
U.S. Appl. No. 11/959,158, filed Dec. 18, 2007 in the name of Saadat et al., non-final Office Action dated Apr. 25, 2011.
U.S. Appl. No. 11/848,532, filed Aug. 31, 2007 in the name of Saadat et al., non-final Office Action dated Apr. 26, 2011.
U.S. Appl. No. 11/828,281, filed Jul. 25, 2007 in the name of Peh et al., non-final Office Action dated Apr. 27, 2011.
U.S. Appl. No. 11/961,950, filed Dec. 20, 2007 in the name of Saadat et al., non-final Office Action dated May 9, 2011.
U.S. Appl. No. 11/961,995, filed Dec. 20, 2007 in the name of Saadat et al., non-final Office Action dated May 9, 2011.
U.S. Appl. No. 11/962,029, filed Dec. 20, 2007 in the name of Saadat et al., non-final Office Action dated May 9, 2011.
U.S. Appl. No. 11/828,267, filed Jul. 25, 2007 in the name of Saadat et al., non-final Office Action dated May 11, 2011.
Japanese Patent Application No. 2009-500630 filed Mar. 16, 2007 in the name of Voyage Medical, Inc., Office Action dated Apr. 27, 2011.
U.S. Appl. No. 11/775,771, filed Jul. 10, 2007 in the name of Saadat et al., final Office Action dated May 12, 2011.
U.S. Appl. No. 11/877,386, filed Oct. 23, 2007 in the name of Saadat et al., non-final Office Action dated May 20, 2011.
U.S. Appl. No. 11/775,819, filed Jul. 10, 2007 in the name of Saadat et al., non-final Office Action dated May 20, 2011.
U.S. Appl. No. 11/775,837, filed Jul. 10, 2007 in the name of Saadat et al., non-final Office Action dated May 23, 2011.
U.S. Appl. No. 12/117,655, filed May 8, 2008 in the name of Peh et al., final Office Action dated Jun. 2, 2011.
U.S. Appl. No. 12/323,281, filed Nov. 25, 2008 in the name of Saadat et al., non-final Office Action dated Jun. 7, 2011.
Japanese Patent Application No. 2007-554156 filed Jan. 30, 2006 in the name of Voyage Medical, Inc., Notice of Allowance dated Jun. 13, 2011.
Extended European search report for Application No. EP20070758716 dated Feb. 28, 2011, 8 Pages.
Extended European search report for Application No. EP20070799466 dated Nov. 18, 2010, 9 pages.
Final Office Action dated Oct. 5, 2010 for U.S. Appl. No. 11/810,850, filed Jun. 7, 2007.
International Search Report and Written Opinion for Application No. PCT/US2007/073184, dated Aug. 12, 2012, 7 pages.
International Search Report for Application No. PCT/US2006/003288, dated Aug. 9, 2007, 1 page.
International Search Report for Application No. PCT/US2007/064195, dated Dec. 7, 2007, 1 page.
International Search Report for Application No. PCT/US2007/071226, dated Sep. 4, 2008, 1 page.
International Search Report for Application No. PCT/US2007/077429, dated Apr. 7, 2008, 1 page.
Non-Final Office Action dated Aug. 8, 2011 for U.S. Appl. No. 12/464,800, filed May 12, 2009.
Non-Final Office Action dated Jun. 8, 2009 for U.S. Appl. No. 12/117,655, filed May 8, 2008.
Non-Final Office Action dated Apr. 11, 2011 for U.S. Appl. No. 11/763,399, filed Jun. 14, 2007.
Non-Final Office Action dated Mar. 16, 2010 for U.S. Appl. No. 11/810,850, filed Jun. 7, 2007.
Written Opinion for Application No. PCT/US2006/003288, dated Aug. 9, 2007, 6 pages.
Written Opinion for Application No. PCT/US2007/064195, dated Dec. 7, 2007, 5 pages.

(56) References Cited

OTHER PUBLICATIONS

Written Opinion for Application No. PCT/US2007/071226, dated Sep. 4, 2008, 4 pages.
Written Opinion for Application No. PCT/US2007/077429, dated Apr. 7, 2008, 5 pages.
Tse HF., et al., "Angiogenesis in Ischaemic Myocardium by Intramyocardial Autologous Bone Marrow Mononuclear Cell Implantation," LANCET, 2003, vol. 361, pp. 47-49.
European Patent Application No. 06734083.6 filed Jan. 30, 2006 in the name of Saadat et al., Examination Communication dated May 18, 2010.
European Patent Application No. 07841754.0 filed Aug. 31, 2007 in the name of Saadat et al., Supplemental European Search Report dated Jun. 30, 2010.
European Patent Application No. 08746822.9 filed Apr. 24, 2008 in the name of Rothe et al., European Search Report dated Mar. 29, 2010.
European Patent Application No. 08746822.9 filed Apr. 24, 2008 in the name of Rothe et al., Office Action dated Jul. 13, 2010.
U.S. Appl. No. 11/259,498, filed Oct. 25, 2005 in the name of Saadat et al., Non-final Office Action dated Feb. 25, 2010.
U.S. Appl. No. 11/560,742, filed Nov. 16, 2006 in the name of Saadat, Non-final Office Action dated Jun. 10, 2010.
U.S. Appl. No. 11/687,597, filed Mar. 16, 2007 in the name of Saadat et al., Non-final Office Action dated Jul. 21, 2010.
U.S. Appl. No. 12/117,655, filed May 8, 2008 in the name of Peh et al., Final Office Action dated Mar. 1, 2010.
U.S. Appl. No. 61/286,283, filed Dec. 14, 2009 in the name of Rothe et al.
U.S. Appl. No. 61/297,462, filed Jan. 22, 2010 in the name of Rothe et al.
Uchida, Developmental History of Cardioscopes, Coronary Angioscopy, pp. 187-197, 2001, Futura Publishing Co., Armonk, NY.

\* cited by examiner

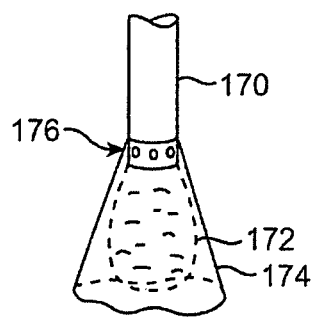
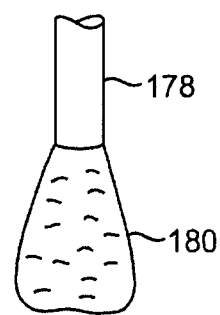
FIG. 11A              FIG. 11B
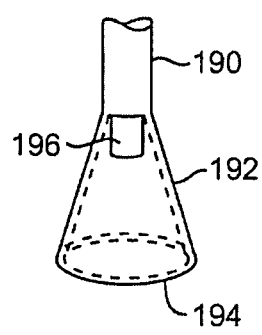
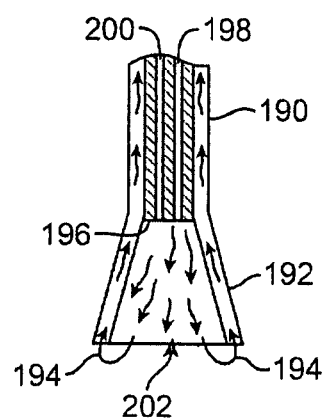
FIG. 13A              FIG. 13B

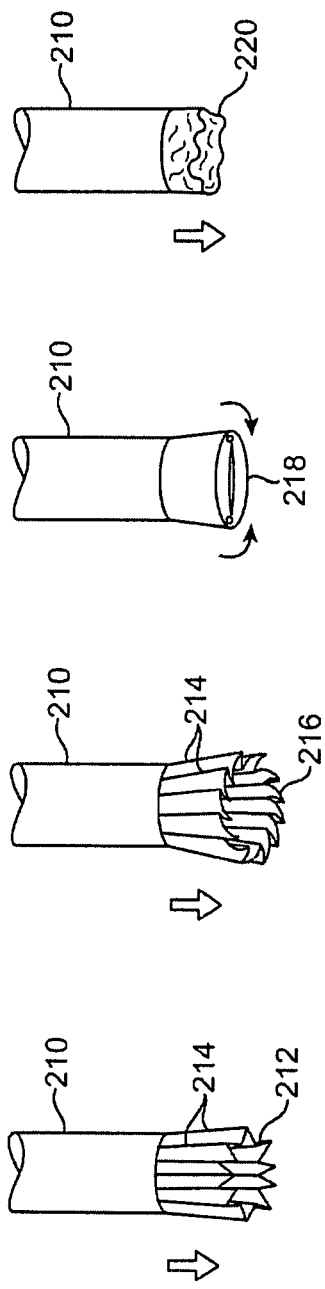

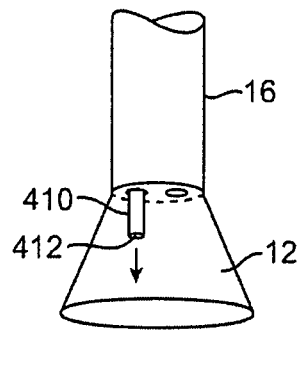
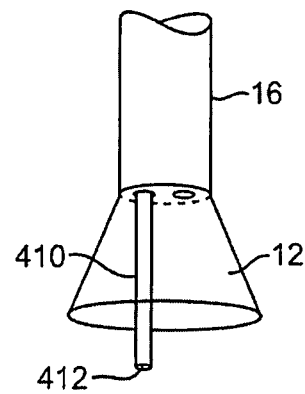
FIG. 35A    FIG. 35B
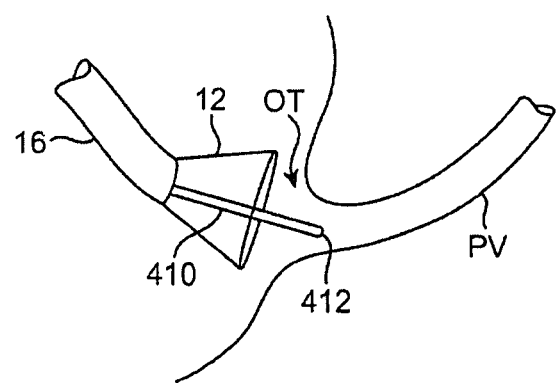
FIG. 35C

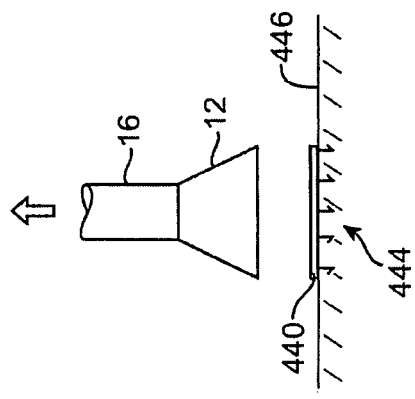
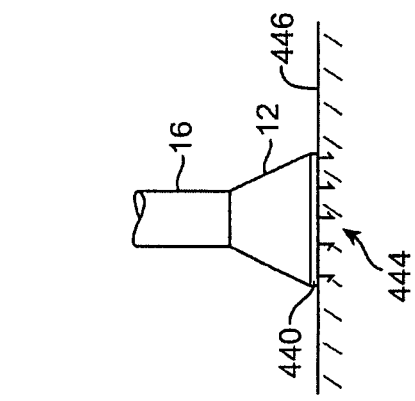
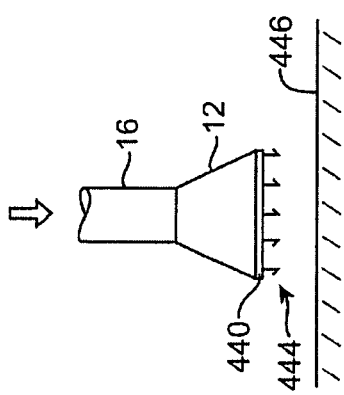

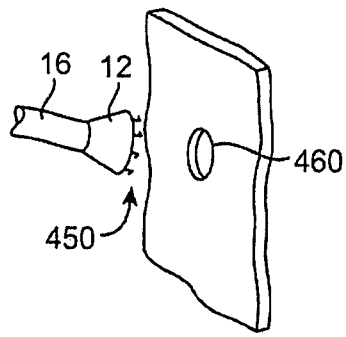
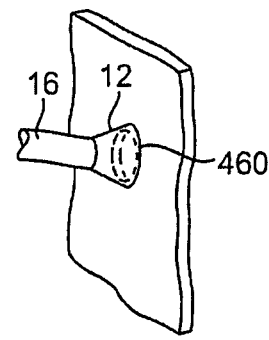
FIG. 41A              FIG. 41B
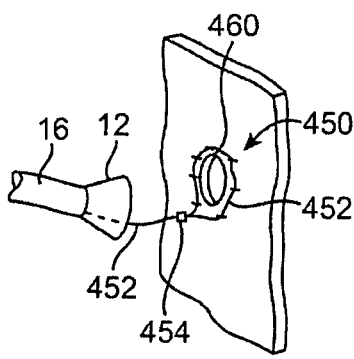
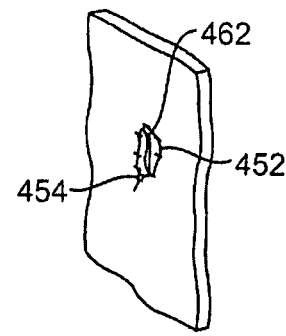
FIG. 41C              FIG. 41D

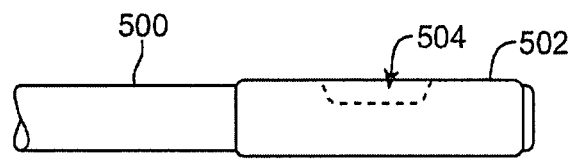
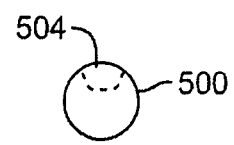
FIG. 44A  FIG. 44B
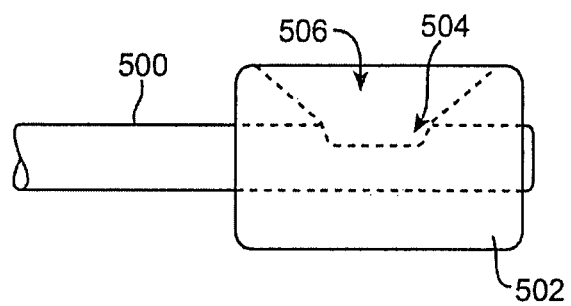
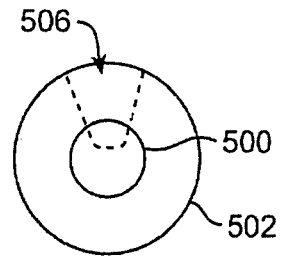
FIG. 45A  FIG. 45C
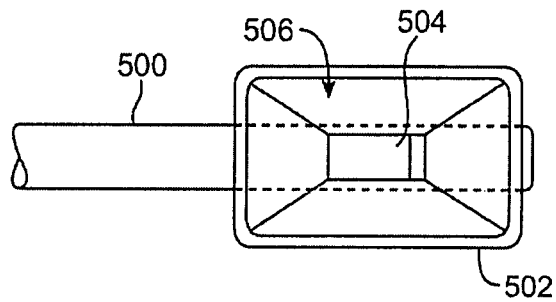
FIG. 45B

VISUALIZATION APPARATUS FOR TRANSSEPTAL ACCESS

CROSS-REFERENCE TO RELATED APPLICATIONS

This application claims the benefit of priority to the following U.S. Prov. Pat. App. Ser. Nos. 60/804,801 filed Jun. 14, 2006; 60/806,924 filed Jul. 10, 2006; 60/806,926 filed Jul. 10, 2006; 60/871,415 filed Dec. 21, 2006; 60/871,424 filed Dec. 21, 2006; 60/888,242 filed Feb. 5, 2007; this is also a continuation-in-part of U.S. patent application Ser. No. 11/259,498 filed Oct. 25, 2005, which claims priority to U.S. Prov. Pat. App. Ser. No. 60/649,246 filed Feb. 2, 2005; and this is also a continuation-in-part of U.S. patent application Ser. No. 11/560,742 filed Nov. 16, 2006, which claims priority to 60/737,521 filed Nov. 16, 2005 and is a continuation-in-part of U.S. patent application Ser. No. 11/259,498 filed Oct. 25, 2005. Each application is incorporated herein by reference in its entirety.

FIELD OF THE INVENTION

The present invention relates generally to medical devices used for visualizing and/or manipulating regions of tissue within a body. More particularly, the present invention relates to apparatus and methods for visualizing and/or manipulating tissue regions within a body lumen, e.g., tissue surrounding or adjacent to valves within a heart, which are generally difficult to image because of surrounding opaque bodily fluids such as blood or the tissue of the inter-atrial septum for transseptal procedures.

BACKGROUND OF THE INVENTION

Conventional devices for visualizing interior regions of a body lumen are known. For example, ultrasound devices have been used to produce images from within a body in vivo. Ultrasound has been used both with and without contrast agents, which typically enhance ultrasound-derived images.

Other conventional methods have utilized catheters or probes having position sensors deployed within the body lumen, such as the interior of a cardiac chamber. These types of positional sensors are typically used to determine the movement of a cardiac tissue surface or the electrical activity within the cardiac tissue. When a sufficient number of points have been sampled by the sensors, a "map" of the cardiac tissue may be generated.

Another conventional device utilizes an inflatable balloon which is typically introduced intravascularly in a deflated state and then inflated against the tissue region to be examined. Imaging is typically accomplished by an optical fiber or other apparatus such as electronic chips for viewing the tissue through the membrane(s) of the inflated balloon. Moreover, the balloon must generally be inflated for imaging. Other conventional balloons utilize a cavity or depression formed at a distal end of the inflated balloon. This cavity or depression is pressed against the tissue to be examined and is flushed with a clear fluid to provide a clear pathway through the blood.

However, such imaging balloons have many inherent disadvantages. For instance, such balloons generally require that the balloon be inflated to a relatively large size which may undesirably displace surrounding tissue and interfere with fine positioning of the imaging system against the tissue. Moreover, the working area created by such inflatable balloons are generally cramped and limited in size. Furthermore, inflated balloons may be susceptible to pressure changes in the surrounding fluid. For example, if the environment surrounding the inflated balloon undergoes pressure changes, e.g., during systolic and diastolic pressure cycles in a beating heart, the constant pressure change may affect the inflated balloon volume and its positioning to produce unsteady or undesirable conditions for optimal tissue imaging.

Accordingly, these types of imaging modalities are generally unable to provide desirable images useful for sufficient diagnosis and therapy of the endoluminal structure, due in part to factors such as dynamic forces generated by the natural movement of the heart. Moreover, anatomic structures within the body can occlude or obstruct the image acquisition process. Also, the presence and movement of opaque bodily fluids such as blood generally make in vivo imaging of tissue regions within the heart difficult.

Other external imaging modalities are also conventionally utilized. For example, computed tomography (CT) and magnetic resonance imaging (MRI) are typical modalities which are widely used to obtain images of body lumens such as the interior chambers of the heart. However, such imaging modalities fail to provide real-time imaging for intra-operative therapeutic procedures. Fluoroscopic imaging, for instance, is widely used to identify anatomic landmarks within the heart and other regions of the body. However, fluoroscopy fails to provide an accurate image of the tissue quality or surface and also fails to provide for instrumentation for performing tissue manipulation or other therapeutic procedures upon the visualized tissue regions. In addition, fluoroscopy provides a shadow of the intervening tissue onto a plate or sensor when it may be desirable to view the intraluminal surface of the tissue to diagnose pathologies or to perform some form of therapy on it.

Thus, a tissue imaging system which is able to provide real-time in vivo images of tissue regions within body lumens such as the heart through opaque media such as blood and which also provide instruments for therapeutic procedures upon the visualized tissue are desirable.

BRIEF SUMMARY OF THE INVENTION

A tissue imaging and manipulation apparatus that may be utilized for procedures within a body lumen, such as the heart, in which visualization of the surrounding tissue is made difficult, if not impossible, by medium contained within the lumen such as blood, is described below. Generally, such a tissue imaging and manipulation apparatus comprises an optional delivery catheter or sheath through which a deployment catheter and imaging hood may be advanced for placement against or adjacent to the tissue to be imaged.

The deployment catheter may define a fluid delivery lumen therethrough as well as an imaging lumen within which an optical imaging fiber or assembly may be disposed for imaging tissue. When deployed, the imaging hood may be expanded into any number of shapes, e.g., cylindrical, conical as shown, semi-spherical, etc., provided that an open area or field is defined by the imaging hood. The open area is the area within which the tissue region of interest may be imaged. The imaging hood may also define an atraumatic contact lip or edge for placement or abutment against the tissue region of interest. Moreover, the distal end of the deployment catheter or separate manipulatable catheters may be articulated through various controlling mechanisms such as push-pull wires manually or via computer control The deployment catheter may also be stabilized relative to the tissue surface through various methods. For instance, inflatable stabilizing balloons positioned along a length of the catheter may be utilized, or tissue engagement anchors may be passed through or along the deployment catheter for temporary engagement of the underlying tissue.

In operation, after the imaging hood has been deployed, fluid may be pumped at a positive pressure through the fluid delivery lumen until the fluid fills the open area completely and displaces any blood from within the open area. The fluid may comprise any biocompatible fluid, e.g., saline, water, plasma, Fluorinert™, etc., which is sufficiently transparent to allow for relatively undistorted visualization through the fluid. The fluid may be pumped continuously or intermittently to allow for image capture by an optional processor which may be in communication with the assembly.

In an exemplary variation for imaging tissue surfaces within a heart chamber containing blood, the tissue imaging and treatment system may generally comprise a catheter body having a lumen defined therethrough, a visualization element disposed adjacent the catheter body, the visualization element having a field of view, a transparent fluid source in fluid communication with the lumen, and a barrier or membrane extendable from the catheter body to localize, between the visualization element and the field of view, displacement of blood by transparent fluid that flows from the lumen, and a piercing instrument translatable through the displaced blood for piercing into the tissue surface within the field of view.

The imaging hood may be formed into any number of configurations and the imaging assembly may also be utilized with any number of therapeutic tools which may be deployed through the deployment catheter.

More particularly in certain variations, the tissue visualization system may comprise components including the imaging hood, where the hood may further include a membrane having a main aperture and additional optional openings disposed over the distal end of the hood. An introducer sheath or the deployment catheter upon which the imaging hood is disposed may further comprise a steerable segment made of multiple adjacent links which are pivotably connected to one another and which may be articulated within a single plane or multiple planes. The deployment catheter itself may be comprised of a multiple lumen extrusion, such as a four-lumen catheter extrusion, which is reinforced with braided stainless steel fibers to provide structural support. The proximal end of the catheter may be coupled to a handle for manipulation and articulation of the system.

To facilitate the transseptal puncture, a piercing needle having a needle sheath, e.g., made with PEEK, or a needle sheath having a tapered or sharpened bevel at its distal end may be advanced through the catheter and advanced into and through the imaging hood. To provide visualization, an imaging element such as a fiberscope or electronic imager such as a solid state camera, e.g., CCD or CMOS, may be mounted, e.g., on a shape memory wire, and positioned within or along the hood interior. A fluid reservoir and/or pump (e.g., syringe, pressurized intravenous bag, etc.) may be fluidly coupled to the proximal end of the catheter to hold the translucent fluid such as saline or contrast medium as well as for providing the pressure to inject the fluid into the imaging hood.

One particular procedure for which the imaging hood and deployment catheter may be utilized includes crossing through a septal wall, e.g., the atrial septum, for transseptally accessing an atrial chamber such as the left atrium while under direct visualization. In particular, the devices and assemblies may be configured to facilitate passage across the atrial septum from the right atrium to the left atrium.

A method for accessing the left atrium of the heart via the septum of the heart, may generally comprise introducing a fluid into the right atrium of the heart, confining the fluid, during beating of the heart, so that blood is displaced sufficiently to allow visualization through the fluid of the surface region of the septum, and under guidance of the visualization of the surface region through the fluid, piercing through a safe transseptal access site within the surface region of the septum. Confinement or containment of the fluid occurs locally within the imaging hood which itself is immersed and surrounded by blood within the heart chamber such that when the translucent fluid is introduced into the imaging hood, the fluid is confined between the hood and tissue surface to be visualized while the surrounding blood remains within the heart chamber.

More particularly, an exemplary method for achieving transseptal puncture and access utilizing the tissue visualization system may comprise intravascularly introducing a sheath into the right atrium of the patient's heart. The imaging hood may be deployed from the introducer sheath within the atrial chamber and contacted against the septal wall, where the surrounding blood may be cleared from within the hood and the underlying tissue may be visualized. Alternatively, the hood may be moved along the tissue wall without clearing the blood from within the hood. As the imaging hood is moved to locate an anatomical landmark such as the fossa ovalis, tactile feedback may be utilized by the physician as a first indicator that the hood has contacted the fossa ovalis and/or the limbus of the fossa ovalis.

Once the fossa ovalis and/or the limbus of the fossa ovalis has been detected, the translucent fluid may be injected into the hood interior to displace the surrounding blood and to provide a clear visual indication of the fossa ovalis surface as a second confirmation that the imaging hood is suitably positioned along the fossa ovalis. The hood may be optionally further moved along the atrial tissue surface inferiorly while under direct visualization until the coronary sinus is visualized as a third indicator and backup confirmation that the fossa ovalis has been located. With the hood positioned over the fossa ovalis and directly visualizing the pale white tissue surface of the fossa, a piercing needle within a needle sheath or a separate beveled sheath may be advanced through the catheter and into the imaging hood where the needle may be pierced into and through the fossa ovalis while under direct visualization. Once the needle has pierced through the tissue and extended into the adjacent atrial chamber, i.e., the left atrial chamber, the piercing needle (if the needle is used) may be retracted to leave the needle sheath passing through the fossa ovalis and extending into the left atrium. A guidewire may be advanced through the sheath to access the left atrium whereupon the sheath may be retracted to leave the guidewire passing through the fossa ovalis and crossing between the left and right atrial chambers. The imaging hood and catheter may then be withdrawn leaving the guidewire passing through the fossa ovalis such that other instrument may be passed along or over the guidewire to access the left atrium.

One variation of the assembly may utilize an off-axis imaging element such as a CCD or CMOS imager, mounted along the hood interior as well as a piercing needle, which may further define one or more tissue engaging features, e.g., helical screw or threads, proximal to the piercing tip for facilitating tissue engagement. When deployed, the imaging hood may be advanced via the deployment catheter distally of the sheath whereupon the hood may be expanded into its deployed configuration. Once a targeted region of tissue, such as the atrial septum, has been engaged the needle may be advanced to pierce through the tissue wall and the guidewire may be advanced through a lumen defined within the needle into the atrial chamber.

The tissue-imaging catheter may be articulated via a steerable portion to direct the distal end towards the atrial septum. The deployment catheter and imaging hood may then be deployed from the sheath and advanced towards the wall of the atrial septum where it may be positioned, e.g., to locate the fossa ovalis along the septal wall. The catheter could be repositioned if necessary to determine the best location to cross the fossa ovalis using a transseptal puncture. Once positioned, the tissue engager may be utilized to temporarily engage or grab onto the underlying tissue to provide for a relatively secure positioning between the hood and the tissue.

Another variation of a method for obtaining transseptal access may utilize a tissue grasper to engage the tissue allowing the penetrating needle to cross the atrial septum by pulling proximally on the tissue with the tissue graspers and distally pushing the needle across the tissue layer. The guidewire may be concentrically positioned within the needle and subsequently advanced into the left atrium. By pulling proximally on the tissue towards the interior of hood, tenting of the tissue into the left atrium may be avoided when pushing distally with the needle upon the tissue wall. Moreover, by pulling proximally on the tissue, accidental puncturing of surrounding anatomical structures may be potentially avoided when passing the needle through the tissue by preventing or inhibiting tissue tenting.

Yet another variation for the tissue visualization assembly includes a translucent imaging balloon which may be optionally included in combination with the imaging hood for inflation and placement against the tissue surface to provide the physician an initial determination of a position of the catheter distal end prior to expansion of the visualization imaging hood and/or prior to deployment of the imaging hood against the tissue wall. The imaging hood may be expanded and the balloon may be inflated and positioned within the hood or distal thereof to allow the underlying tissue surface to be visualized by pressing the balloon against the tissue surface prior to hood expansion and/or deployment to provide an initial image and visual assessment of the catheter location relative to the atrial septum.

If the initial visual assessment indicates that the catheter should be moved to another location for transseptal puncture, the catheter position may be adjusted and moved while visualizing against the tissue wall or the catheter may be removed from the tissue wall and repositioned for another visual assessment. Alternatively, the balloon may be deflated and the catheter repositioned to another location along the tissue wall, where the balloon may again be re-inflated for visualization. Once the catheter position has been visually confirmed as being positioned at a desirable location for puncture, the balloon may be deflated and optionally withdrawn from the imaging hood and the purging fluid may be pumped into the hood to provide the open space for visualization and treatment by additional tools.

In yet other variations for accomplishing intravascular transseptal access, the imaging assembly may be utilized with various introduction sheaths to facilitate the articulation and positioning of the imaging hood with respect to the septal wall. Such an introduction sheath may be curved or pre-bent such that its distal portion is angled towards or away from the septal wall when positioned within the patient's heart. Alternatively, the sheath may simply extend in a straightened configuration.

In utilizing the imaging hood in any one of the procedures described herein, the hood may have an open field which is uncovered and clear to provide direct tissue contact between the hood interior and the underlying tissue to effect any number of treatments upon the tissue, as described above. Yet in additional variations, the imaging hood may utilize other configurations where the imaging hood includes at least one layer of a transparent elastomeric membrane over the distal opening of the hood. An aperture having a diameter which is less than a diameter of the outer lip of imaging hood may be defined over the center of membrane where a longitudinal axis of the hood intersects the membrane such that the interior of the hood remains open and in fluid communication with the environment external to the hood. Furthermore, the aperture may be sized, e.g., between 1 to 2 mm or more in diameter and the membrane can be made from any number of transparent elastomers such as silicone, polyurethane, latex, etc. such that contacted tissue may also be visualized through the membrane as well as through the aperture. The membrane itself may define a plurality of openings which may optionally be adjusted in size depending upon the desired fluid flow characteristics.

Yet another feature which may be utilized with any of the embodiments described above, particularly for transseptal puncture, may include the use of a needle body positioned through the catheter and having multi-colored gradations or markings along its shaft extending from the needle tip used in conjunction with the tissue visualization catheter. The needle can be of varying sizes and diameters with segments along the body marked with different colors. The needle may also have markings or gradations engraved or otherwise marked along the body of the needle to visually indicate a length of the needle in millimeters or inches.

The operator may gauge the depth of needle penetration into the tissue by correlating the exposed colored gradations or markings. When the needle penetrates the tissue, the exposed markings just above the tissue surface can be read under direct visualization provided by the tissue visualization catheter. Direct visualization is achieved by the CCD/CMOS camera built-in the catheter and by flushing opaque bodily fluid such as blood, out of the interior of the hood using clear saline.

Generally, the tissue visualization system described herein may provide for several advantages in intravascular transseptal access. For instance, direct visualization of the underlying tissue such as the fossa ovalis may be obtained as well as visualization of other anatomical landmarks such as the coronary sinus. Visual confirmation of the coronary sinus location, for instance, may be utilized as an orientation indicator to locate and/or confirm a location of the fossa ovalis given the proximity of the fossa ovalis and the coronary sinus to one another. This may be particularly useful in providing a method for identifying an anatomical feature, such as the coronary sinus, that is relatively easy to identify visually to help locate another anatomical feature which is relatively more difficult to identify visually, such as the fossa ovalis. Additionally, in initially accessing the septal wall, the sheath may be curved or pre-bent to point away from the septal wall to allow for the deployment catheter carrying the imaging hood to be curved and steered towards the septal wall particularly when there is limited space in the right atrium for maneuvering the imaging hood.

Moreover, while undergoing transseptal puncture with a piercing instrument through the septal wall, the tissue imaging system provides a mechanism for directly visualizing the entire procedure of inserting and passing a needle, for instance, through the fossa ovalis and passing the guidewire into the left atrium. Additionally, because the puncturing of the tissue is directly visualized, excessive tenting or distortion of the septal wall by the piercing instrument may be visually monitored where blood entering the visual field within the hood is an indication that the underlying tissue is distorting and thus causing poor contact between the imaging hood and the underlying tissue.

BRIEF DESCRIPTION OF THE DRAWINGS

FIG. 11A shows a side view of another variation of a tissue imager having an imaging balloon within an expandable hood.

FIG. 11B shows another variation of a tissue imager utilizing a translucent or transparent imaging balloon.

FIGS. 13A and 13B show exemplary side and cross-sectional views, respectively, of another variation in which the injected fluid may be drawn back into the device for minimizing fluid input into a body being treated.

FIGS. 14A to 14D show various configurations and methods for configuring an imaging hood into a low-profile for delivery and/or deployment.

FIGS. 35A to 35C show an example of an extendible cannula generally comprising an elongate tubular member which may be positioned within the deployment catheter during delivery and then projected distally through the imaging hood and optionally beyond.

FIGS. 39A to 39C show one method for implanting the removable disk of FIGS. 38A and 38B.

FIGS. 41A to 41D show one method for deploying the anchor assembly of FIGS. 40A and 40B for closing an opening or wound.

FIGS. 44A and 44B show side and end views, respectively, of a deployment catheter having a side-imaging balloon in an un-inflated low-profile configuration.

FIGS. 45A to 45C show side, top, and end views, respectively, of the inflated balloon of FIGS. 44A and 44B defining a visualization field in the inflated balloon.

DETAILED DESCRIPTION OF THE INVENTION

A tissue-imaging and manipulation apparatus described below is able to provide real-time images in vivo of tissue regions within a body lumen such as a heart, which is filled with blood flowing dynamically therethrough and is also able to provide intravascular tools and instruments for performing various procedures upon the imaged tissue regions. Such an apparatus may be utilized for many procedures, e.g., facilitating transseptal access to the left atrium, cannulating the coronary sinus, diagnosis of valve regurgitation/stenosis, valvuloplasty, atrial appendage closure, arrhythmogenic focus ablation, among other procedures.

Figure 1A:
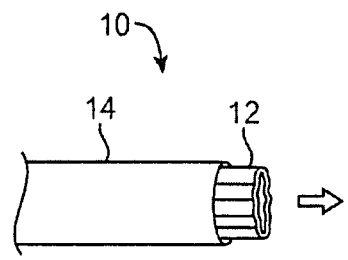
FIG. 1A shows a side view of one variation of a tissue imaging apparatus during deployment from a sheath or delivery catheter.
Figure 1B:
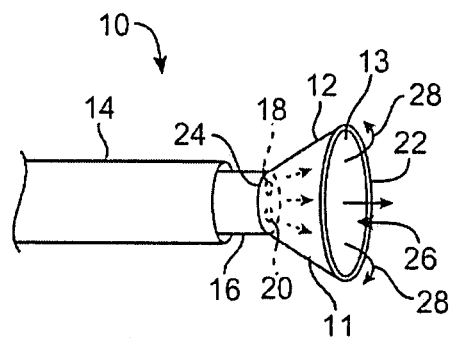
FIG. 1B shows the deployed tissue imaging apparatus of FIG. 1A having an optionally expandable hood or sheath attached to an imaging and/or diagnostic catheter.
Figure 1C:
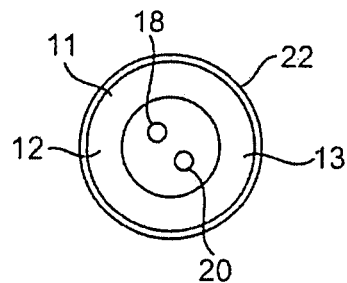
FIG. 1C shows an end view of a deployed imaging apparatus.

One variation of a tissue access and imaging apparatus is shown in the detail perspective views of FIGS. 1A to 1C. As shown in FIG. 1A, tissue imaging and manipulation assembly 10 may be delivered intravascularly through the patient's body in a low-profile configuration via a delivery catheter or sheath 14. In the case of treating tissue, such as the mitral valve located at the outflow tract of the left atrium of the heart, it is generally desirable to enter or access the left atrium while minimizing trauma to the patient. To non-operatively effect such access, one conventional approach involves puncturing the intra-atrial septum from the right atrial chamber to the left atrial chamber in a procedure commonly called a transseptal procedure or septostomy. For procedures such as percutaneous valve repair and replacement, transseptal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 1B. Imaging hood 12 may be fabricated from a variety of pliable or conformable biocompatible material including but not limited to, e.g., polymeric, plastic, or woven materials. One example of a woven material is Kevlar® (E. I. du Pont de Nemours, Wilmington, Del.), which is an aramid and which can be made into thin, e.g., less than 0.001 in., materials which maintain enough integrity for such applications described herein. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or a spring steel, or plastic, etc., may be fabricated and covered with the polymeric, plastic, or woven material. Hence, imaging hood 12 may comprise any of a wide variety of barriers or membrane structures, as may generally be used to localize displacement of blood or the like from a selected volume of a body lumen or heart chamber. In exemplary embodiments, a volume within an inner surface 13 of imaging hood 12 will be significantly less than a volume of the hood 12 between inner surface 13 and outer surface 11.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging tissue. When deployed, imaging hood 12 may expand into any number of shapes, e.g., cylindrical, conical as shown, semi-spherical, etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 1C shows an end view of the imaging hood 12 in its deployed configuration. Also shown are the contact lip or edge 22 and fluid delivery lumen 18 and imaging lumen 20.

Figure 1D:
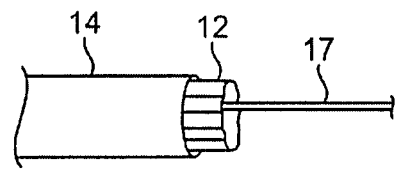
FIGS. 1D to 1F show the apparatus of FIGS. 1A to 1C with an additional lumen, e.g., for passage of a guidewire therethrough.
Figure 1E:
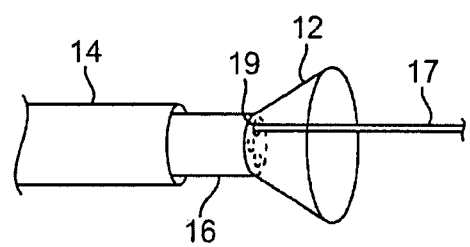
Figure 1F:
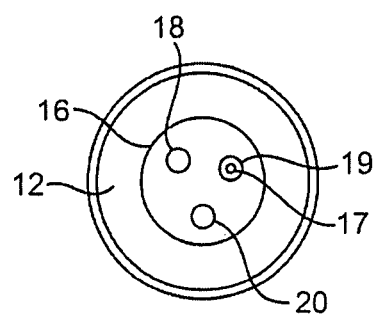

The imaging and manipulation assembly 10 may additionally define a guidewire lumen therethrough, e.g., a concentric or eccentric lumen, as shown in the side and end views, respectively, of FIGS. 1D to 1F. The deployment catheter 16 may define guidewire lumen 19 for facilitating the passage of the system over or along a guidewire 17, which may be advanced intravascularly within a body lumen. The deployment catheter 16 may then be advanced over the guidewire 17, as generally known in the art.

In operation, after imaging hood 12 has been deployed, as in FIG. 1B, and desirably positioned against the tissue region to be imaged along contact edge 22, the displacing fluid may be pumped at positive pressure through fluid delivery lumen 18 until the fluid fills open area 26 completely and displaces any fluid 28 from within open area 26. The displacing fluid flow may be laminarized to improve its clearing effect and to help prevent blood from re-entering the imaging hood 12. Alternatively, fluid flow may be started before the deployment takes place. The displacing fluid, also described herein as imaging fluid, may comprise any biocompatible fluid, e.g., saline, water, plasma, etc., which is sufficiently transparent to allow for relatively undistorted visualization through the fluid. Alternatively or additionally, any number of therapeutic drugs may be suspended within the fluid or may comprise the fluid itself which is pumped into open area 26 and which is subsequently passed into and through the heart and the patient body.

Figure 2A:
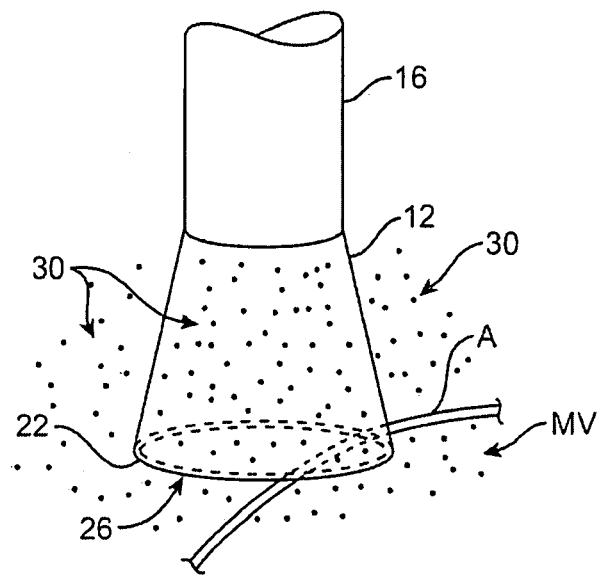
FIGS. 2A and 2B show one example of a deployed tissue imager positioned against or adjacent to the tissue to be imaged and a flow of fluid, such as saline, displacing blood from within the expandable hood.
Figure 2B:
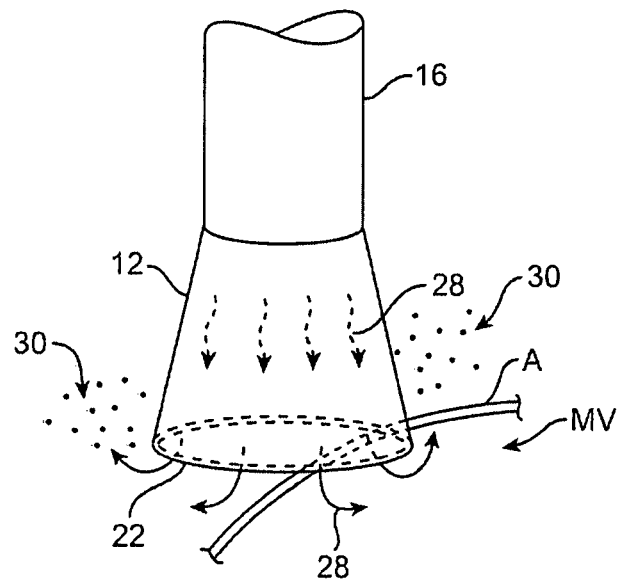

As seen in the example of FIGS. 2A and 2B, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 2A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 2B.

Although contact edge 22 need not directly contact the underlying tissue, it is at least preferably brought into close proximity to the tissue such that the flow of clear fluid 28 from open area 26 may be maintained to inhibit significant backflow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid 30. This image may then be recorded or available for real-time viewing for performing a therapeutic procedure. The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

Figure 3A:
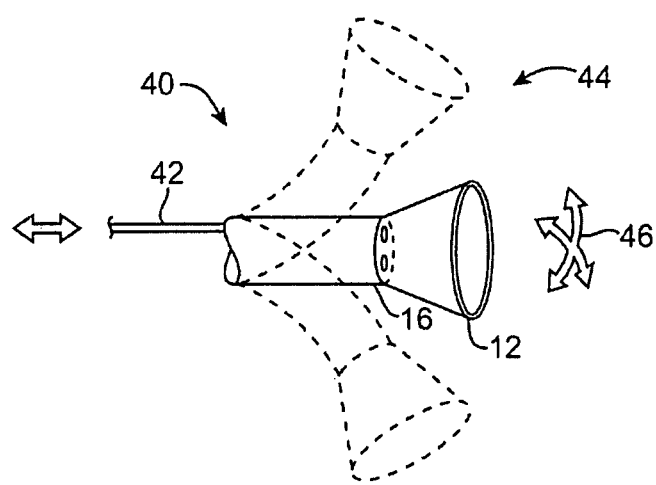
FIG. 3A shows an articulatable imaging assembly which may be manipulated via push-pull wires or by computer control.

In desirably positioning the assembly at various regions within the patient body, a number of articulation and manipulation controls may be utilized. For example, as shown in the articulatable imaging assembly 40 in FIG. 3A, one or more push-pull wires 42 may be routed through deployment catheter 16 for steering the distal end portion of the device in various directions 46 to desirably position the imaging hood 12 adjacent to a region of tissue to be visualized. Depending upon the positioning and the number of push-pull wires 42 utilized, deployment catheter 16 and imaging hood 12 may be articulated into any number of configurations 44. The push-pull wire or wires 42 may be articulated via their proximal ends from outside the patient body manually utilizing one or more controls. Alternatively, deployment catheter 16 may be articulated by computer control, as further described below.

Figure 3B:
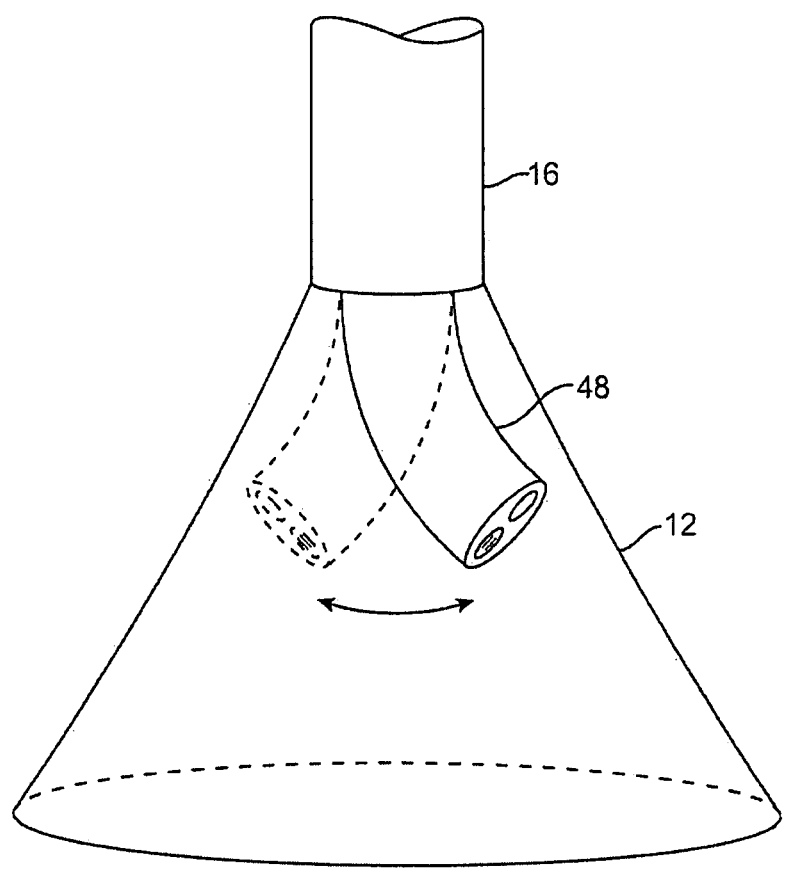
FIGS. 3B and 3C show steerable instruments, respectively, where an articulatable delivery catheter may be steered within the imaging hood or a distal portion of the deployment catheter itself may be steered.

Additionally or alternatively, an articulatable delivery catheter 48, which may be articulated via one or more push-pull wires and having an imaging lumen and one or more working lumens, may be delivered through the deployment catheter 16 and into imaging hood 12. With a distal portion of articulatable delivery catheter 48 within imaging hood 12, the clear displacing fluid may be pumped through delivery catheter 48 or deployment catheter 16 to clear the field within imaging hood 12. As shown in FIG. 3B, the articulatable delivery catheter 48 may be articulated within the imaging hood to obtain a better image of tissue adjacent to the imaging hood 12. Moreover, articulatable delivery catheter 48 may be articulated to direct an instrument or tool passed through the catheter 48, as described in detail below, to specific areas of tissue imaged through imaging hood 12 without having to reposition deployment catheter 16 and re-clear the imaging field within hood 12.

Figure 3C:
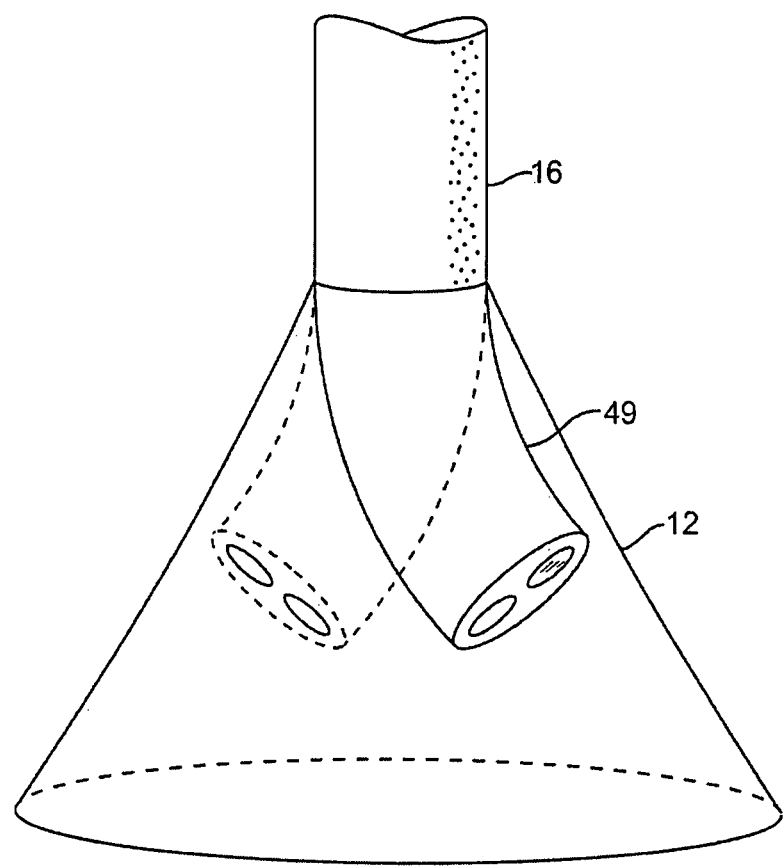

Alternatively, rather than passing an articulatable delivery catheter 48 through the deployment catheter 16, a distal portion of the deployment catheter 16 itself may comprise a distal end 49 which is articulatable within imaging hood 12, as shown in FIG. 3C. Directed imaging, instrument delivery, etc., may be accomplished directly through one or more lumens within deployment catheter 16 to specific regions of the underlying tissue imaged within imaging hood 12.

Figure 4A:
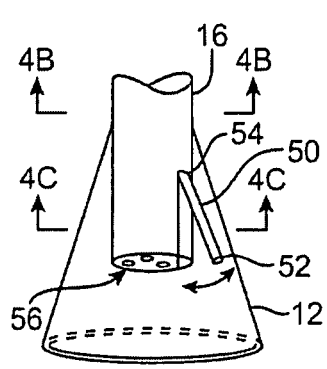
FIGS. 4A to 4C show side and cross-sectional end views, respectively, of another variation having an off-axis imaging capability.

Visualization within the imaging hood 12 may be accomplished through an imaging lumen 20 defined through deployment catheter 16, as described above. In such a configuration, visualization is available in a straight-line manner, i.e., images are generated from the field distally along a longitudinal axis defined by the deployment catheter 16. Alternatively or additionally, an articulatable imaging assembly having a pivotable support member 50 may be connected to, mounted to, or otherwise passed through deployment catheter 16 to provide for visualization off-axis relative to the longitudinal axis defined by deployment catheter 16, as shown in FIG. 4A. Support member 50 may have an imaging element 52, e.g., a CCD or CMOS imager or optical fiber, attached at its distal end with its proximal end connected to deployment catheter 16 via a pivoting connection 54.

Figure 4B:
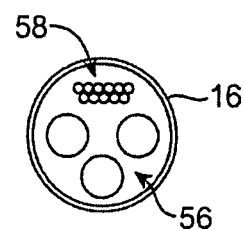
Figure 4C:
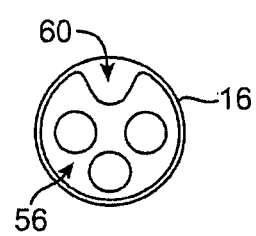

If one or more optical fibers are utilized for imaging, the optical fibers 58 may be passed through deployment catheter 16, as shown in the cross-section of FIG. 4B, and routed through the support member 50. The use of optical fibers 58 may provide for increased diameter sizes of the one or several lumens 56 through deployment catheter 16 for the passage of diagnostic and/or therapeutic tools therethrough. Alternatively, electronic chips, such as a charge coupled device (CCD) or a CMOS imager, which are typically known, may be utilized in place of the optical fibers 58, in which case the electronic imager may be positioned in the distal portion of the deployment catheter 16 with electric wires being routed proximally through the deployment catheter 16. Alternatively, the electronic imagers may be wirelessly coupled to a receiver for the wireless transmission of images. Additional optical fibers or light emitting diodes (LEDs) can be used to provide lighting for the image or operative theater, as described below in further detail. Support member 50 may be pivoted via connection 54 such that the member 50 can be positioned in a low-profile configuration within channel or groove 60 defined in a distal portion of catheter 16, as shown in the cross-section of FIG. 4C. During intravascular delivery of deployment catheter 16 through the patient body, support member 50 can be positioned within channel or groove 60 with imaging hood 12 also in its low-profile configuration. During visualization, imaging hood 12 may be expanded into its deployed configuration and support member 50 may be deployed into its off-axis configuration for imaging the tissue adjacent to hood 12, as in FIG. 4A. Other configurations for support member 50 for off-axis visualization may be utilized, as desired.

Figure 5:
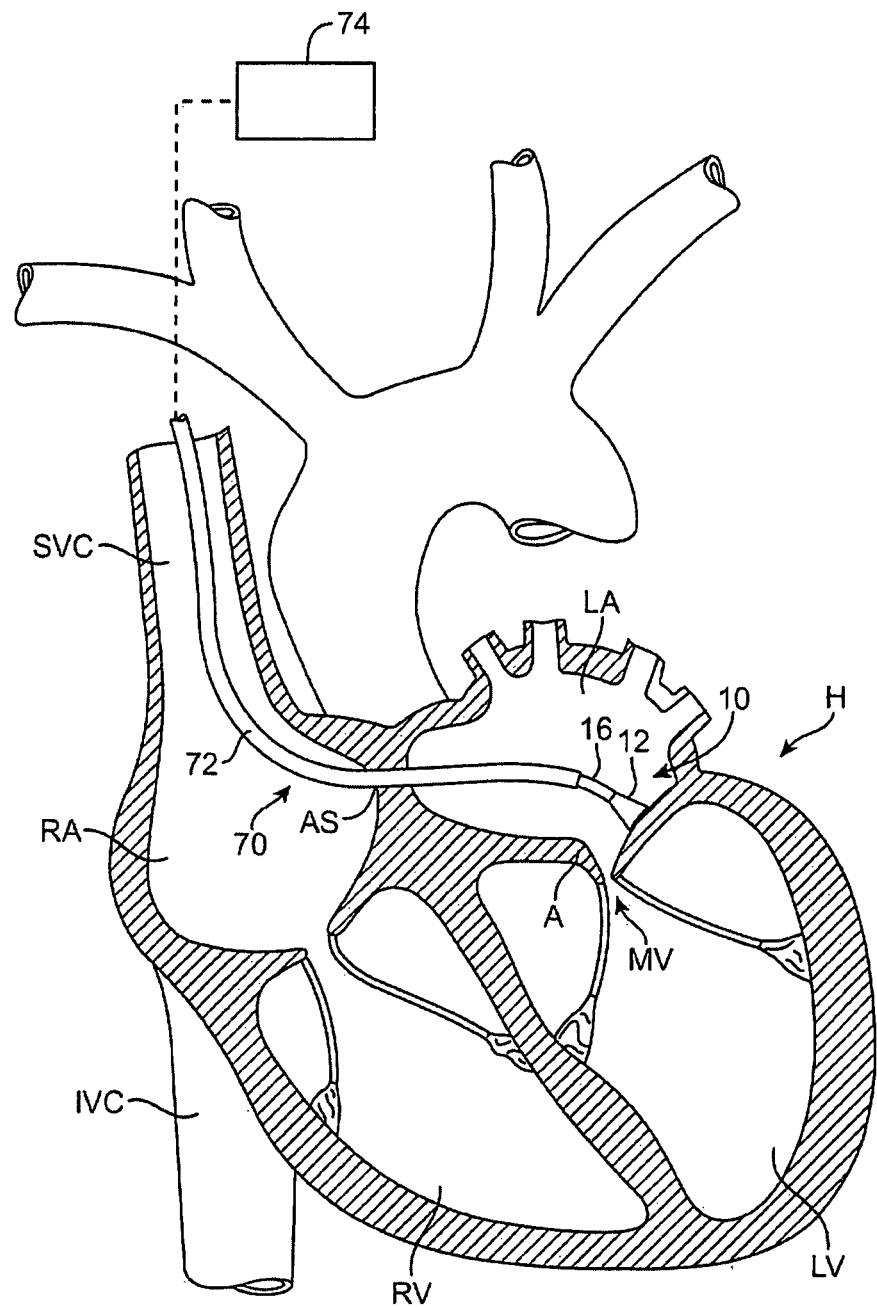
FIG. 5 shows an illustrative view of an example of a tissue imager advanced intravascularly within a heart for imaging tissue regions within an atrial chamber.

FIG. 5 shows an illustrative cross-sectional view of a heart H having tissue regions of interest being viewed via an imaging assembly 10. In this example, delivery catheter assembly 70 may be introduced percutaneously into the patient's vasculature and advanced through the superior vena cava SVC and into the right atrium RA. The delivery catheter or sheath 72 may be articulated through the atrial septum AS and into the left atrium LA for viewing or treating the tissue, e.g., the annulus A, surrounding the mitral valve MV. As shown, deployment catheter 16 and imaging hood 12 may be advanced out of delivery catheter 72 and brought into contact or in proximity to the tissue region of interest. In other examples, delivery catheter assembly 70 may be advanced through the inferior vena cava IVC, if so desired. Moreover, other regions of the heart H, e.g., the right ventricle RV or left ventricle LV, may also be accessed and imaged or treated by imaging assembly 10.

In accessing regions of the heart H or other parts of the body, the delivery catheter or sheath 14 may comprise a conventional intra-vascular catheter or an endoluminal delivery device. Alternatively, robotically-controlled delivery catheters may also be optionally utilized with the imaging assembly described herein, in which case a computer-controller 74 may be used to control the articulation and positioning of the delivery catheter 14. An example of a robotically-controlled delivery catheter which may be utilized is described in further detail in US Pat. Pub. 2002/0087169 A1 to Brock et al. entitled "Flexible Instrument", which is incorporated herein by reference in its entirety. Other robotically-controlled delivery catheters manufactured by Hansen Medical, Inc. (Mountain View, Calif.) may also be utilized with the delivery catheter 14.

Figure 6A:
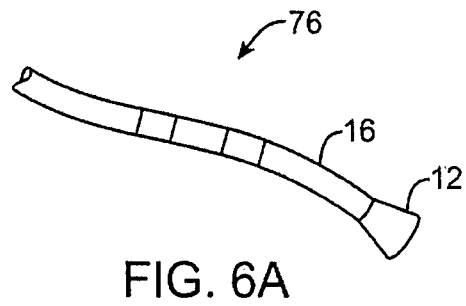
FIGS. 6A to 6C illustrate deployment catheters having one or more optional inflatable balloons or anchors for stabilizing the device during a procedure.
Figure 6B:
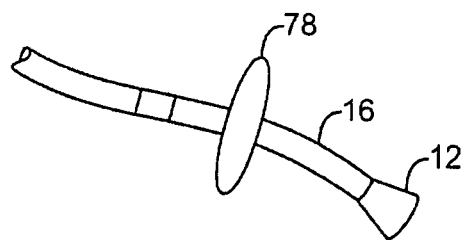
Figure 6C:
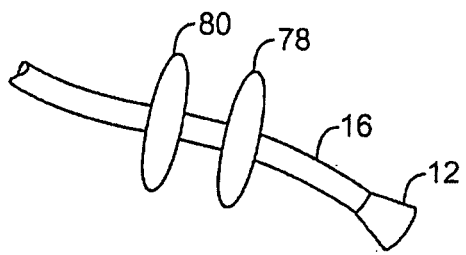

To facilitate stabilization of the deployment catheter 16 during a procedure, one or more inflatable balloons or anchors 76 may be positioned along the length of catheter 16, as shown in FIG. 6A. For example, when utilizing a transseptal approach across the atrial septum AS into the left atrium LA, the inflatable balloons 76 may be inflated from a low-profile into their expanded configuration to temporarily anchor or stabilize the catheter 16 position relative to the heart H. FIG. 6B shows a first balloon 78 inflated while FIG. 6C also shows a second balloon 80 inflated proximal to the first balloon 78. In such a configuration, the septal wall AS may be wedged or sandwiched between the balloons 78, 80 to temporarily stabilize the catheter 16 and imaging hood 12. A single balloon 78 or both balloons 78, 80 may be used. Other alternatives may utilize expandable mesh members, malecots, or any other temporary expandable structure. After a procedure has been accomplished, the balloon assembly 76 may be deflated or re-configured into a low-profile for removal of the deployment catheter 16.

Figure 7A:
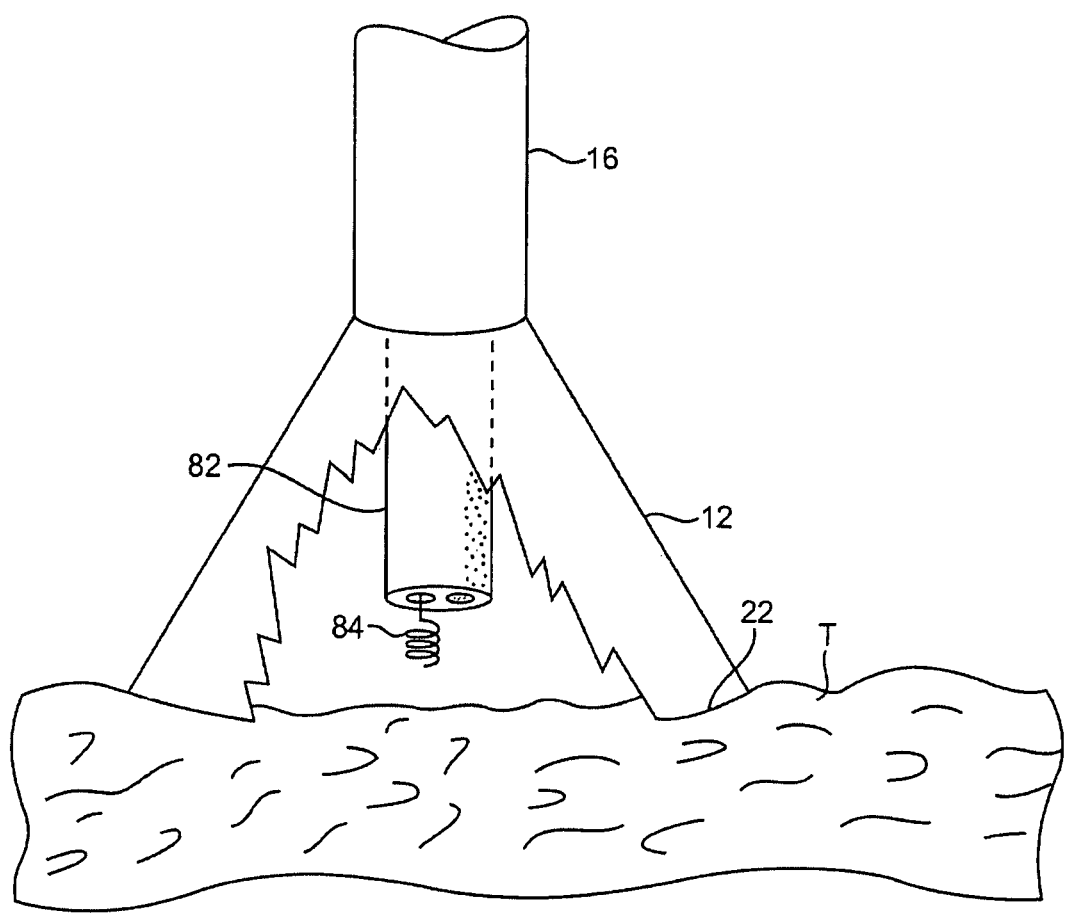
FIGS. 7A and 7B illustrate a variation of an anchoring mechanism such as a helical tissue piercing device for temporarily stabilizing the imaging hood relative to a tissue surface.

To further stabilize a position of the imaging hood 12 relative to a tissue surface to be imaged, various anchoring mechanisms may be optionally employed for temporarily holding the imaging hood 12 against the tissue. Such anchoring mechanisms may be particularly useful for imaging tissue which is subject to movement, e.g., when imaging tissue within the chambers of a beating heart. A tool delivery catheter 82 having at least one instrument lumen and an optional visualization lumen may be delivered through deployment catheter 16 and into an expanded imaging hood 12. As the imaging hood 12 is brought into contact against a tissue surface T to be examined, anchoring mechanisms such as a helical tissue piercing device 84 may be passed through the tool delivery catheter 82, as shown in FIG. 7A, and into imaging hood 12.

Figure 7B:
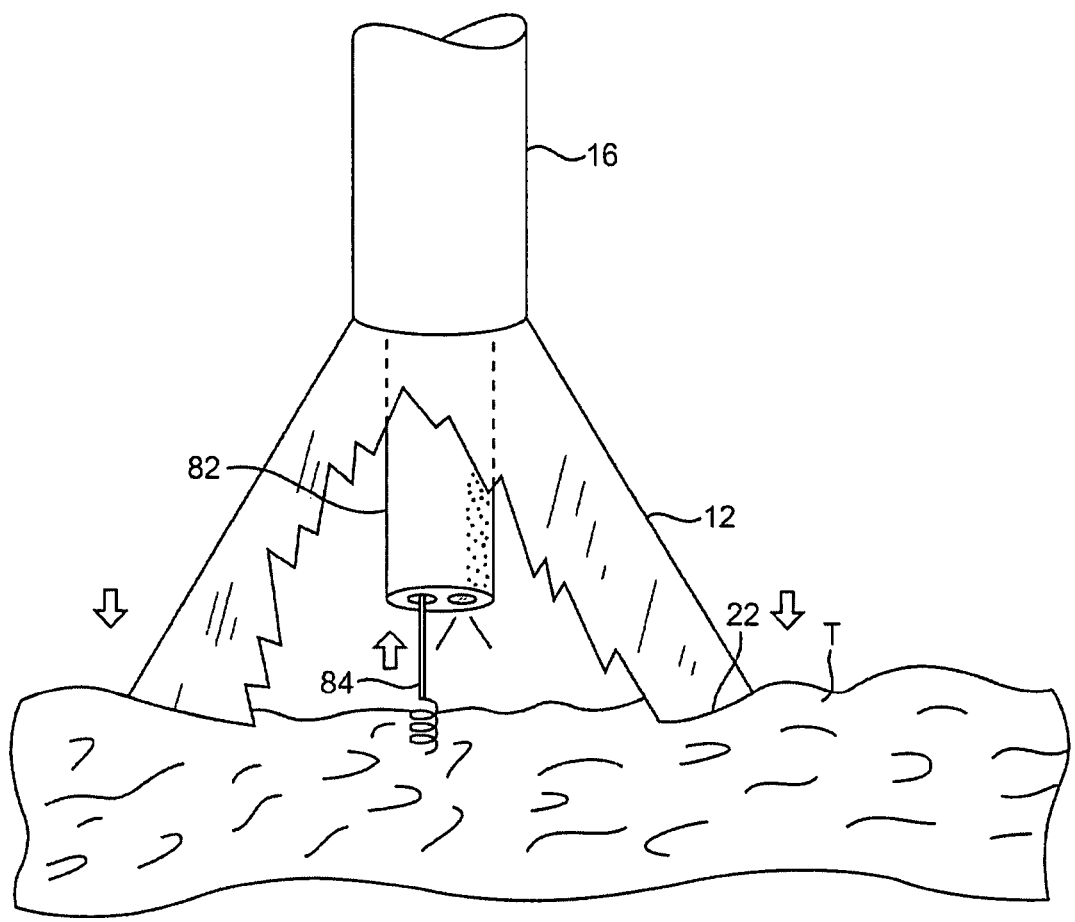

The helical tissue engaging device 84 may be torqued from its proximal end outside the patient body to temporarily anchor itself into the underlying tissue surface T. Once embedded within the tissue T, the helical tissue engaging device 84 may be pulled proximally relative to deployment catheter 16 while the deployment catheter 16 and imaging hood 12 are pushed distally, as indicated by the arrows in FIG. 7B, to gently force the contact edge or lip 22 of imaging hood against the tissue T. The positioning of the tissue engaging device 84 may be locked temporarily relative to the deployment catheter 16 to ensure secure positioning of the imaging hood 12 during a diagnostic or therapeutic procedure within the imaging hood 12. After a procedure, tissue engaging device 84 may be disengaged from the tissue by torquing its proximal end in the opposite direction to remove the anchor form the tissue T and the deployment catheter 16 may be repositioned to another region of tissue where the anchoring process may be repeated or removed from the patient body. The tissue engaging device 84 may also be constructed from other known tissue engaging devices such as vacuum-assisted engagement or grasper-assisted engagement tools, among others.

Although a helical anchor 84 is shown, this is intended to be illustrative and other types of temporary anchors may be utilized, e.g., hooked or barbed anchors, graspers, etc. Moreover, the tool delivery catheter 82 may be omitted entirely and the anchoring device may be delivered directly through a lumen defined through the deployment catheter 16.

Figure 7C:
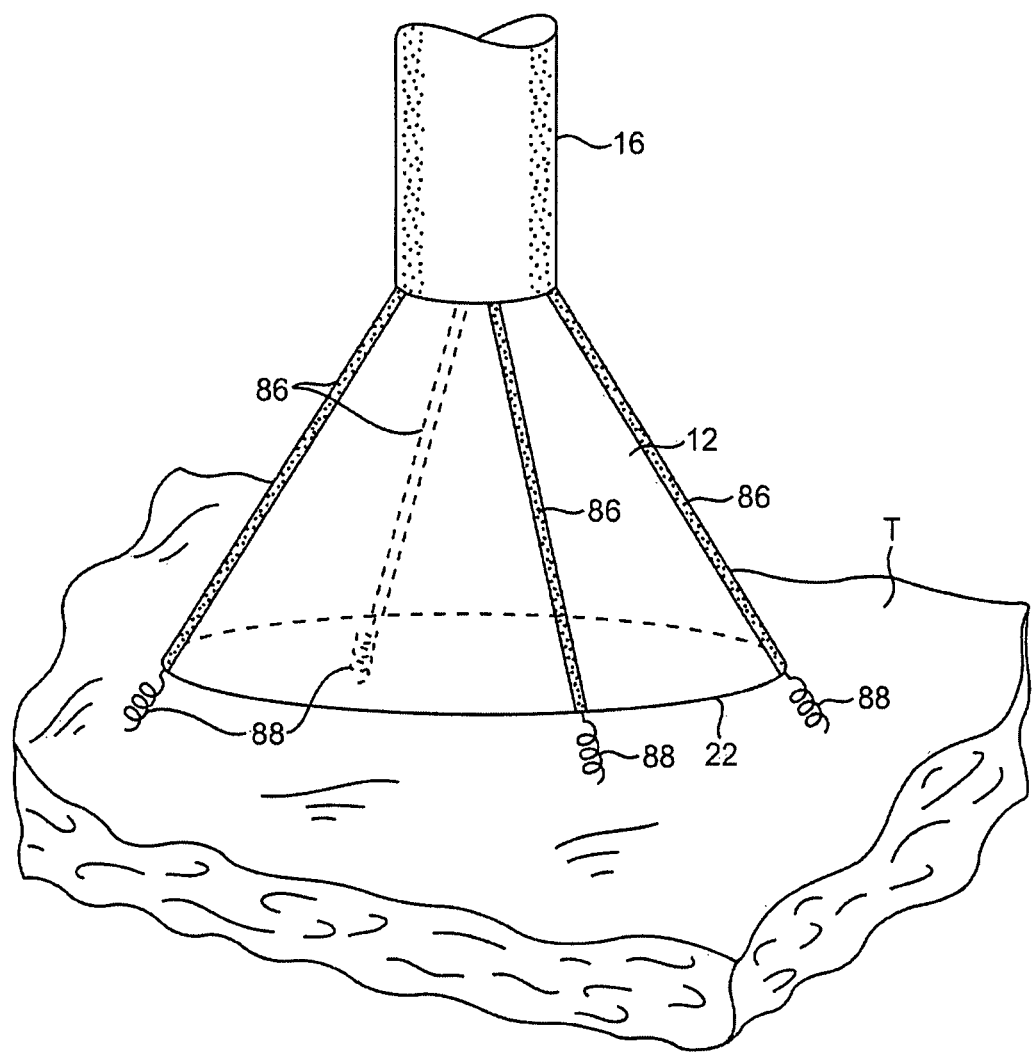
FIG. 7C shows another variation for anchoring the imaging hood having one or more tubular support members integrated with the imaging hood; each support members may define a lumen therethrough for advancing a helical tissue anchor within.

In another variation where the tool delivery catheter 82 may be omitted entirely to temporarily anchor imaging hood 12, FIG. 7C shows an imaging hood 12 having one or more tubular support members 86, e.g., four support members 86 as shown, integrated with the imaging hood 12. The tubular support members 86 may define lumens therethrough each having helical tissue engaging devices 88 positioned within. When an expanded imaging hood 12 is to be temporarily anchored to the tissue, the helical tissue engaging devices 88 may be urged distally to extend from imaging hood 12 and each may be torqued from its proximal end to engage the underlying tissue T. Each of the helical tissue engaging devices 88 may be advanced through the length of deployment catheter 16 or they may be positioned within tubular support members 86 during the delivery and deployment of imaging hood 12. Once the procedure within imaging hood 12 is finished, each of the tissue engaging devices 88 may be disengaged from the tissue and the imaging hood 12 may be repositioned to another region of tissue or removed from the patient body.

Figure 8A:
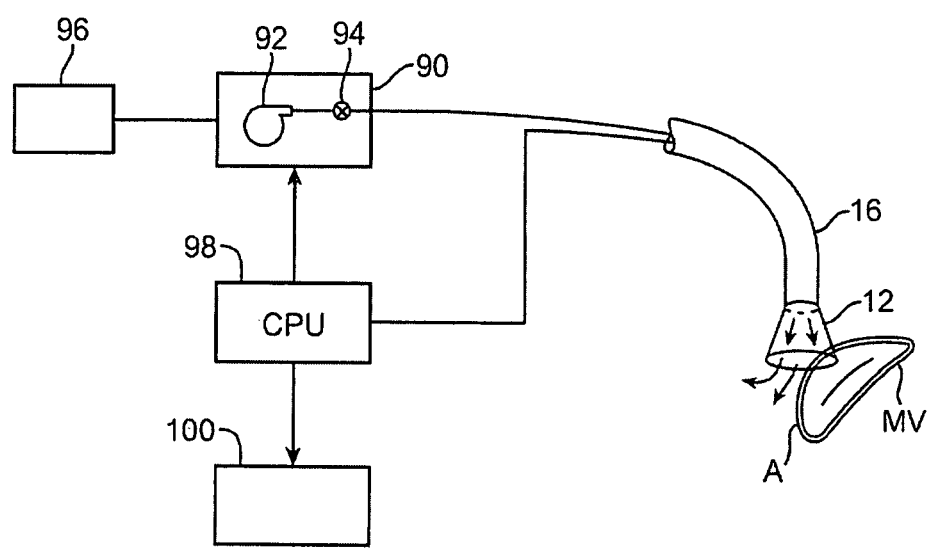
FIG. 8A shows an illustrative example of one variation of how a tissue imager may be utilized with an imaging device.

An illustrative example is shown in FIG. 8A of a tissue imaging assembly connected to a fluid delivery system 90 and to an optional processor 98 and image recorder and/or viewer 100. The fluid delivery system 90 may generally comprise a pump 92 and an optional valve 94 for controlling the flow rate of the fluid into the system. A fluid reservoir 96, fluidly connected to pump 92, may hold the fluid to be pumped through imaging hood 12. An optional central processing unit or processor 98 may be in electrical communication with fluid delivery system 90 for controlling flow parameters such as the flow rate and/or velocity of the pumped fluid. The processor 98 may also be in electrical communication with an image recorder and/or viewer 100 for directly viewing the images of tissue received from within imaging hood 12. Imager recorder and/or viewer 100 may also be used not only to record the image but also the location of the viewed tissue region, if so desired.

Optionally, processor 98 may also be utilized to coordinate the fluid flow and the image capture. For instance, processor 98 may be programmed to provide for fluid flow from reservoir 96 until the tissue area has been displaced of blood to obtain a clear image. Once the image has been determined to be sufficiently clear, either visually by a practitioner or by computer, an image of the tissue may be captured automatically by recorder 100 and pump 92 may be automatically stopped or slowed by processor 98 to cease the fluid flow into the patient. Other variations for fluid delivery and image capture are, of course, possible and the aforementioned configuration is intended only to be illustrative and not limiting.

Figure 8B:
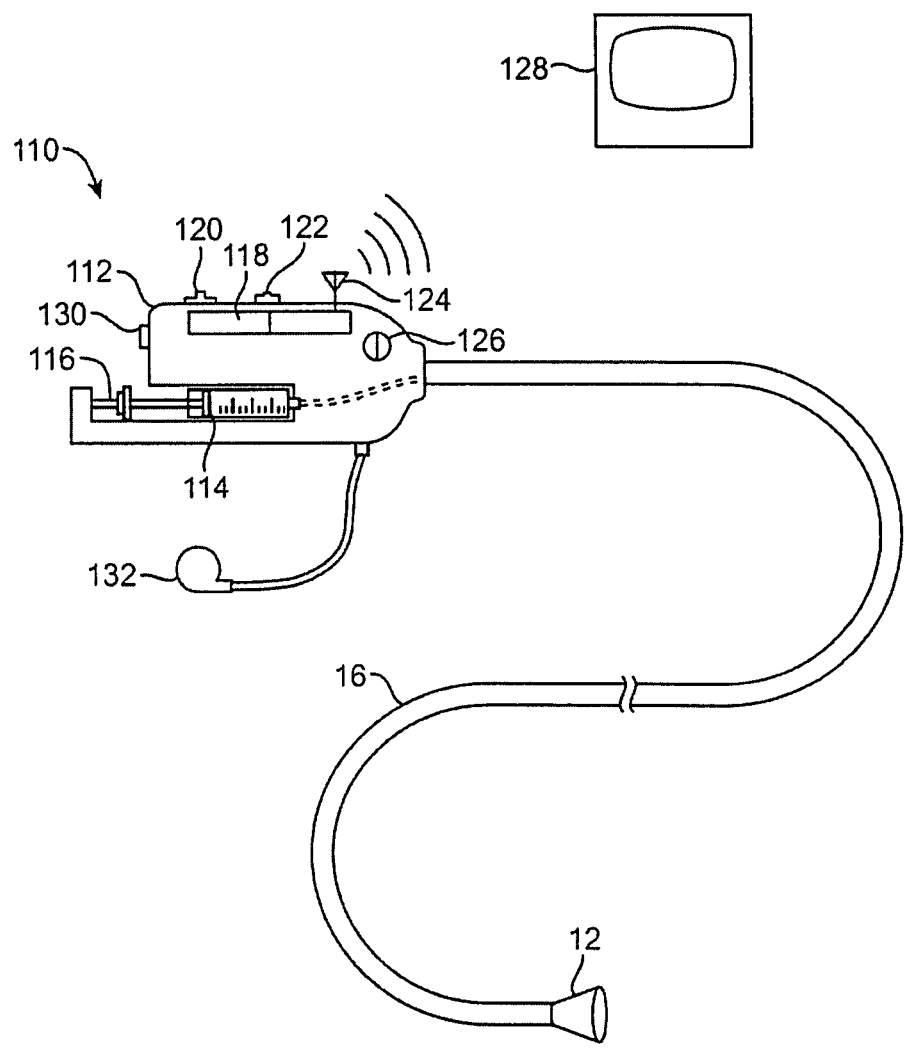
FIG. 8B shows a further illustration of a hand-held variation of the fluid delivery and tissue manipulation system.

FIG. 8B shows a further illustration of a hand-held variation of the fluid delivery and tissue manipulation system 110. In this variation, system 110 may have a housing or handle assembly 112 which can be held or manipulated by the physician from outside the patient body. The fluid reservoir 114, shown in this variation as a syringe, can be fluidly coupled to the handle assembly 112 and actuated via a pumping mechanism 116, e.g., lead screw. Fluid reservoir 114 may be a simple reservoir separated from the handle assembly 112 and fluidly coupled to handle assembly 112 via one or more tubes. The fluid flow rate and other mechanisms may be metered by the electronic controller 118.

Deployment of imaging hood 12 may be actuated by a hood deployment switch 120 located on the handle assembly 112 while dispensation of the fluid from reservoir 114 may be actuated by a fluid deployment switch 122, which can be electrically coupled to the controller 118. Controller 118 may also be electrically coupled to a wired or wireless antenna 124 optionally integrated with the handle assembly 112, as shown in the figure. The wireless antenna 124 can be used to wirelessly transmit images captured from the imaging hood 12 to a receiver, e.g., via Bluetooth® wireless technology (Bluetooth SIG, Inc., Bellevue, Wash.), RF, etc., for viewing on a monitor 128 or for recording for later viewing.

Articulation control of the deployment catheter 16, or a delivery catheter or sheath 14 through which the deployment catheter 16 may be delivered, may be accomplished by computer control, as described above, in which case an additional controller may be utilized with handle assembly 112. In the case of manual articulation, handle assembly 112 may incorporate one or more articulation controls 126 for manual manipulation of the position of deployment catheter 16. Handle assembly 112 may also define one or more instrument ports 130 through which a number of intravascular tools may be passed for tissue manipulation and treatment within imaging hood 12, as described further below. Furthermore, in certain procedures, fluid or debris may be sucked into imaging hood 12 for evacuation from the patient body by optionally fluidly coupling a suction pump 132 to handle assembly 112 or directly to deployment catheter 16.

Figure 9A:
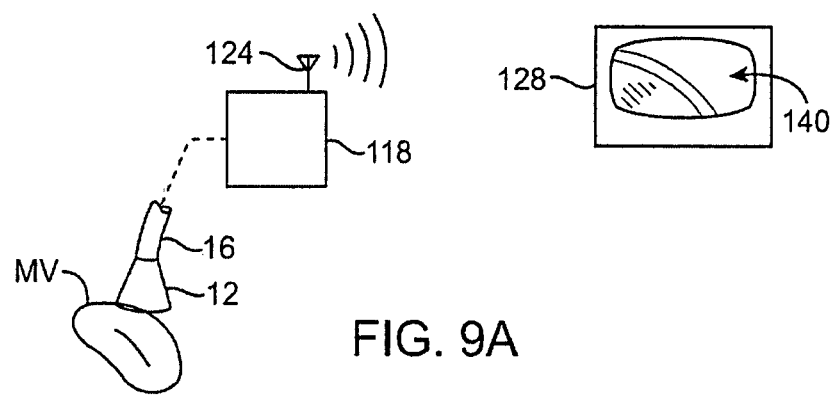
FIGS. 9A to 9C illustrate an example of capturing several images of the tissue at multiple regions.
Figure 9B:
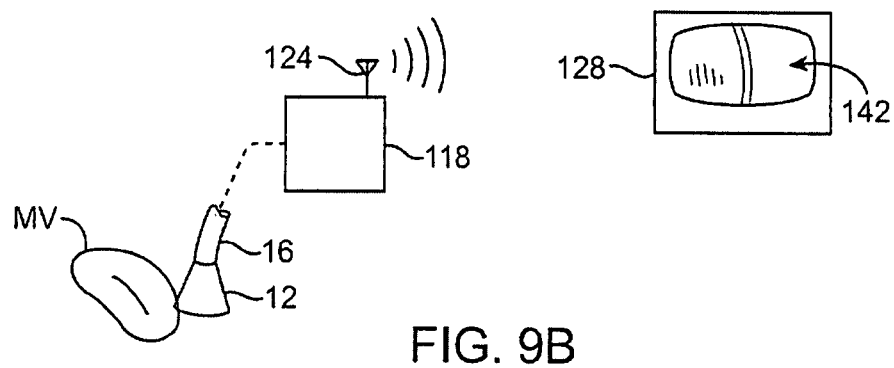
Figure 9C:
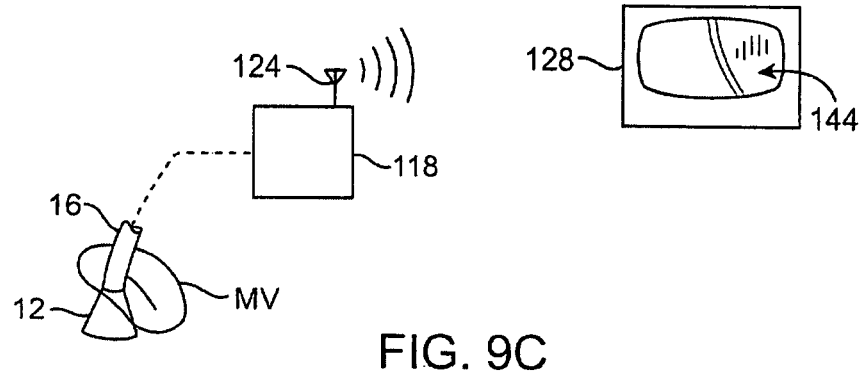

As described above, fluid may be pumped continuously into imaging hood 12 to provide for clear viewing of the underlying tissue. Alternatively, fluid may be pumped temporarily or sporadically only until a clear view of the tissue is available to be imaged and recorded, at which point the fluid flow may cease and the blood may be allowed to seep or flow back into imaging hood 12. FIGS. 9A to 9C illustrate an example of capturing several images of the tissue at multiple regions. Deployment catheter 16 may be desirably positioned and imaging hood 12 deployed and brought into position against a region of tissue to be imaged, in this example the tissue surrounding a mitral valve MV within the left atrium of a patient's heart. The imaging hood 12 may be optionally anchored to the tissue, as described above, and then cleared by pumping the imaging fluid into the hood 12. Once sufficiently clear, the tissue may be visualized and the image captured by control electronics 118. The first captured image 140 may be stored and/or transmitted wirelessly 124 to a monitor 128 for viewing by the physician, as shown in FIG. 9A.

The deployment catheter 16 may be then repositioned to an adjacent portion of mitral valve MV, as shown in FIG. 9B, where the process may be repeated to capture a second image 142 for viewing and/or recording. The deployment catheter 16 may again be repositioned to another region of tissue, as shown in FIG. 9C, where a third image 144 may be captured for viewing and/or recording. This procedure may be repeated as many times as necessary for capturing a comprehensive image of the tissue surrounding mitral valve MV, or any other tissue region. When the deployment catheter 16 and imaging hood 12 is repositioned from tissue region to tissue region, the pump may be stopped during positioning and blood or surrounding fluid may be allowed to enter within imaging hood 12 until the tissue is to be imaged, where the imaging hood 12 may be cleared, as above.

As mentioned above, when the imaging hood 12 is cleared by pumping the imaging fluid within for clearing the blood or other bodily fluid, the fluid may be pumped continuously to maintain the imaging fluid within the hood 12 at a positive pressure or it may be pumped under computer control for slowing or stopping the fluid flow into the hood 12 upon detection of various parameters or until a clear image of the underlying tissue is obtained. The control electronics 118 may also be programmed to coordinate the fluid flow into the imaging hood 12 with various physical parameters to maintain a clear image within imaging hood 12.

Figure 10A:
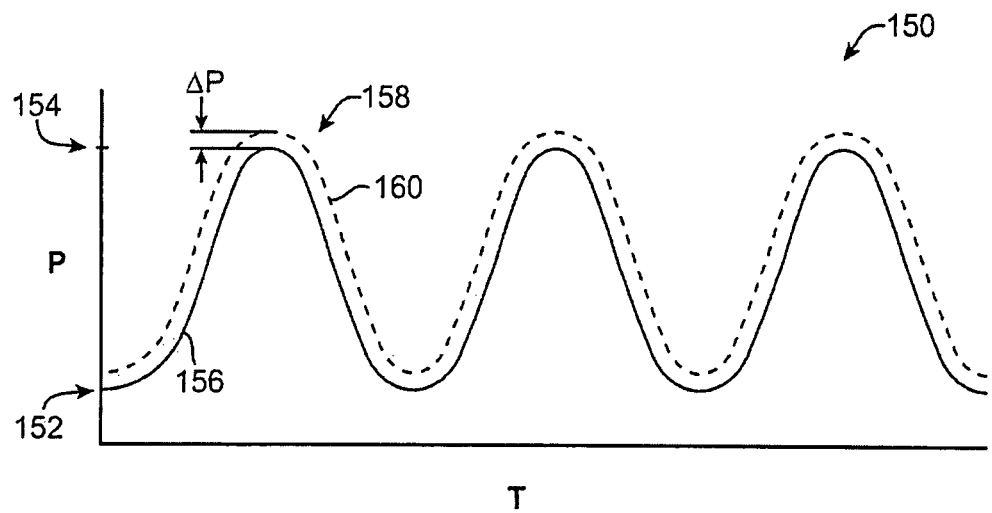
FIGS. 10A and 10B show charts illustrating how fluid pressure within the imaging hood may be coordinated with the surrounding blood pressure; the fluid pressure in the imaging hood may be coordinated with the blood pressure or it may be regulated based upon pressure feedback from the blood.

One example is shown in FIG. 10A which shows a chart 150 illustrating how fluid pressure within the imaging hood 12 may be coordinated with the surrounding blood pressure. Chart 150 shows the cyclical blood pressure 156 alternating between diastolic pressure 152 and systolic pressure 154 over time T due to the beating motion of the patient heart. The fluid pressure of the imaging fluid, indicated by plot 160, within imaging hood 12 may be automatically timed to correspond to the blood pressure changes 160 such that an increased pressure is maintained within imaging hood 12 which is consistently above the blood pressure 156 by a slight increase ΔP, as illustrated by the pressure difference at the peak systolic pressure 158. This pressure difference, ΔP, may be maintained within imaging hood 12 over the pressure variance of the surrounding blood pressure to maintain a positive imaging fluid pressure within imaging hood 12 to maintain a clear view of the underlying tissue. One benefit of maintaining a constant ΔP is a constant flow and maintenance of a clear field.

Figure 10B:
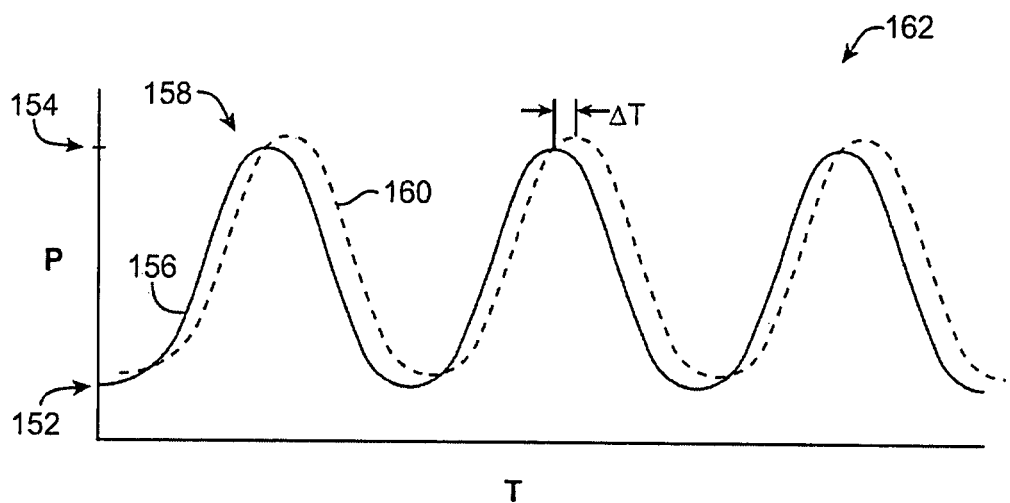

FIG. 10B shows a chart 162 illustrating another variation for maintaining a clear view of the underlying tissue where one or more sensors within the imaging hood 12, as described in further detail below, may be configured to sense pressure changes within the imaging hood 12 and to correspondingly increase the imaging fluid pressure within imaging hood 12. This may result in a time delay, ΔT, as illustrated by the shifted fluid pressure 160 relative to the cycling blood pressure 156, although the time delays ΔT may be negligible in maintaining the clear image of the underlying tissue. Predictive software algorithms can also be used to substantially eliminate this time delay by predicting when the next pressure wave peak will arrive and by increasing the pressure ahead of the pressure wave's arrival by an amount of time equal to the aforementioned time delay to essentially cancel the time delay out.

The variations in fluid pressure within imaging hood 12 may be accomplished in part due to the nature of imaging hood 12. An inflatable balloon, which is conventionally utilized for imaging tissue, may be affected by the surrounding blood pressure changes. On the other hand, an imaging hood 12 retains a constant volume therewithin and is structurally unaffected by the surrounding blood pressure changes, thus allowing for pressure increases therewithin. The material that hood 12 is made from may also contribute to the manner in which the pressure is modulated within this hood 12. A stiffer hood material, such as high durometer polyurethane or Nylon, may facilitate the maintaining of an open hood when deployed. On the other hand, a relatively lower durometer or softer material, such as a low durometer PVC or polyurethane, may collapse from the surrounding fluid pressure and may not adequately maintain a deployed or expanded hood.

Turning now to the imaging hood, other variations of the tissue imaging assembly may be utilized, as shown in FIG. 11A, which shows another variation comprising an additional imaging balloon 172 within an imaging hood 174. In this variation, an expandable balloon 172 having a translucent skin may be positioned within imaging hood 174. Balloon 172 may be made from any distensible biocompatible material having sufficient translucent properties which allow for visualization therethrough. Once the imaging hood 174 has been deployed against the tissue region of interest, balloon 172 may be filled with a fluid, such as saline, or less preferably a gas, until balloon 172 has been expanded until the blood has been sufficiently displaced. The balloon 172 may thus be expanded proximal to or into contact against the tissue region to be viewed. The balloon 172 can also be filled with contrast media to allow it to be viewed on fluoroscopy to aid in its positioning. The imager, e.g., fiber optic, positioned within deployment catheter 170 may then be utilized to view the tissue region through the balloon 172 and any additional fluid which may be pumped into imaging hood 174 via one or more optional fluid ports 176, which may be positioned proximally of balloon 172 along a portion of deployment catheter 170. Alternatively, balloon 172 may define one or more holes over its surface which allow for seepage or passage of the fluid contained therein to escape and displace the blood from within imaging hood 174.

FIG. 11B shows another alternative in which balloon 180 may be utilized alone. Balloon 180, attached to deployment catheter 178, may be filled with fluid, such as saline or contrast media, and is preferably allowed to come into direct contact with the tissue region to be imaged.

Figure 12A:
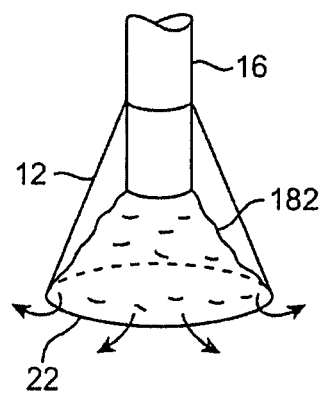
FIG. 12A shows another variation in which a flexible expandable or distensible membrane may be incorporated within the imaging hood to alter the volume of fluid dispensed.

FIG. 12A shows another alternative in which deployment catheter 16 incorporates imaging hood 12, as above, and includes an additional flexible membrane 182 within imaging hood 12. Flexible membrane 182 may be attached at a distal end of catheter 16 and optionally at contact edge 22. Imaging hood 12 may be utilized, as above, and membrane 182 may be deployed from catheter 16 in vivo or prior to placing catheter 16 within a patient to reduce the volume within imaging hood 12. The volume may be reduced or minimized to reduce the amount of fluid dispensed for visualization or simply reduced depending upon the area of tissue to be visualized.

Figure 12B:
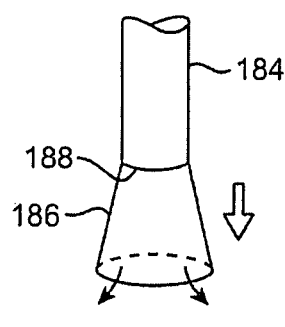
FIGS. 12B and 12C show another variation in which the imaging hood may be partially or selectively deployed from the catheter to alter the area of the tissue being visualized as well as the volume of the dispensed fluid.
Figure 12C:
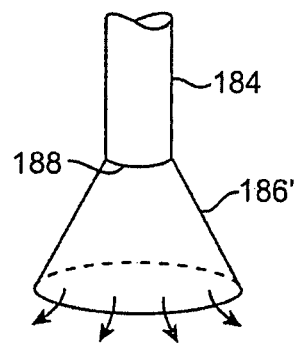

FIGS. 12B and 12C show yet another alternative in which imaging hood 186 may be withdrawn proximally within deployment catheter 184 or deployed distally from catheter 186, as shown, to vary the volume of imaging hood 186 and thus the volume of dispensed fluid. Imaging hood 186 may be seen in FIG. 12B as being partially deployed from, e.g., a circumferentially defined lumen within catheter 184, such as annular lumen 188. The underlying tissue may be visualized with imaging hood 186 only partially deployed. Alternatively, imaging hood 186' may be fully deployed, as shown in FIG. 12C, by urging hood 186' distally out from annular lumen 188. In this expanded configuration, the area of tissue to be visualized may be increased as hood 186' is expanded circumferentially.

FIGS. 13A and 13B show perspective and cross-sectional side views, respectively, of yet another variation of imaging assembly which may utilize a fluid suction system for minimizing the amount of fluid injected into the patient's heart or other body lumen during tissue visualization. Deployment catheter 190 in this variation may define an inner tubular member 196 which may be integrated with deployment catheter 190 or independently translatable. Fluid delivery lumen 198 defined through member 196 may be fluidly connected to imaging hood 192, which may also define one or more open channels 194 over its contact lip region. Fluid pumped through fluid delivery lumen 198 may thus fill open area 202 to displace any blood or other fluids or objects therewithin. As the clear fluid is forced out of open area 202, it may be sucked or drawn immediately through one or more channels 194 and back into deployment catheter 190. Tubular member 196 may also define one or more additional working channels 200 for the passage of any tools or visualization devices.

In deploying the imaging hood in the examples described herein, the imaging hood may take on any number of configurations when positioned or configured for a low-profile delivery within the delivery catheter, as shown in the examples of FIGS. 14A to 14D. These examples are intended to be illustrative and are not intended to be limiting in scope. FIG. 14A shows one example in which imaging hood 212 may be compressed within catheter 210 by folding hood 212 along a plurality of pleats. Hood 212 may also comprise scaffolding or frame 214 made of a super-elastic or shape memory material or alloy, e.g., Nitinol, Elgiloy, shape memory polymers, electroactive polymers, or a spring stainless steel. The shape memory material may act to expand or deploy imaging hood 212 into its expanded configuration when urged in the direction of the arrow from the constraints of catheter 210.

FIG. 14B shows another example in which imaging hood 216 may be expanded or deployed from catheter 210 from a folded and overlapping configuration. Frame or scaffolding 214 may also be utilized in this example. FIG. 14C shows yet another example in which imaging hood 218 may be rolled, inverted, or everted upon itself for deployment. In yet another example, FIG. 14D shows a configuration in which imaging hood 220 may be fabricated from an extremely compliant material which allows for hood 220 to be simply compressed into a low-profile shape. From this low-profile compressed shape, simply releasing hood 220 may allow for it to expand into its deployed configuration, especially if a scaffold or frame of a shape memory or superelastic material, e.g., Nitinol, is utilized in its construction.

Figure 15A:
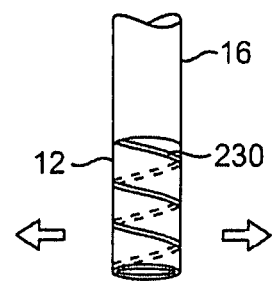
FIGS. 15A and 15B show an imaging hood having an helically expanding frame or support.
Figure 15B:
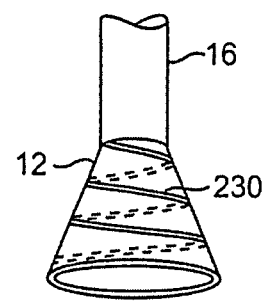

Another variation for expanding the imaging hood is shown in FIGS. 15A and 15B which illustrates an helically expanding frame or support 230. In its constrained low-profile configuration, shown in FIG. 15A, helical frame 230 may be integrated with the imaging hood 12 membrane. When free to expand, as shown in FIG. 15B, helical frame 230 may expand into a conical or tapered shape. Helical frame 230 may alternatively be made out of heat-activated Nitinol to allow it to expand upon application of a current.

Figure 16A:
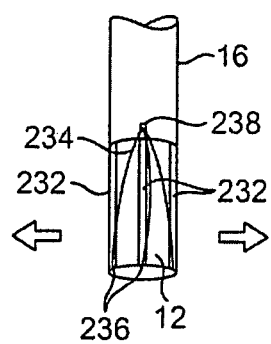
FIGS. 16A and 16B show another imaging hood having one or more hood support members, which are pivotably attached at their proximal ends to deployment catheter, integrated with a hood membrane.
Figure 16B:
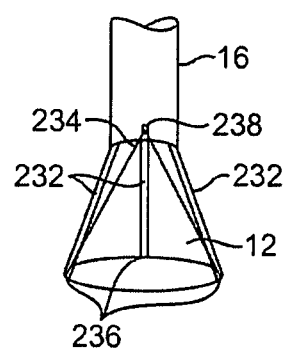

FIGS. 16A and 16B show yet another variation in which imaging hood 12 may comprise one or more hood support members 232 integrated with the hood membrane. These longitudinally attached support members 232 may be pivotably attached at their proximal ends to deployment catheter 16. One or more pullwires 234 may be routed through the length of deployment catheter 16 and extend through one or more openings 238 defined in deployment catheter 16 proximally to imaging hood 12 into attachment with a corresponding support member 232 at a pullwire attachment point 236. The support members 232 may be fabricated from a plastic or metal, such as stainless steel. Alternatively, the support members 232 may be made from a superelastic or shape memory alloy, such as Nitinol, which may self-expand into its deployed configuration without the use or need of pullwires. A heat-activated Nitinol may also be used which expands upon the application of thermal energy or electrical energy. In another alternative, support members 232 may also be constructed as inflatable lumens utilizing, e.g., PET balloons. From its low-profile delivery configuration shown in FIG. 16A, the one or more pullwires 234 may be tensioned from their proximal ends outside the patient body to pull a corresponding support member 232 into a deployed configuration, as shown in FIG. 16B, to expand imaging hood 12. To reconfigure imaging hood 12 back into its low profile, deployment catheter 16 may be pulled proximally into a constraining catheter or the pullwires 234 may be simply pushed distally to collapse imaging hood 12.

Figure 17A:
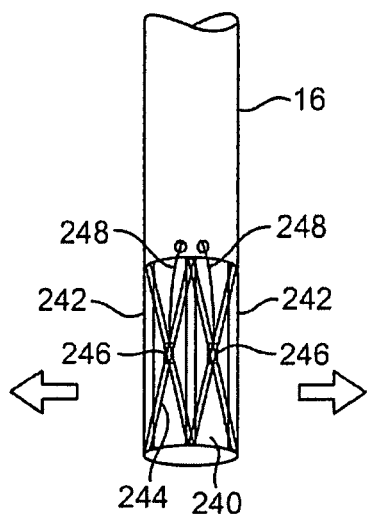
FIGS. 17A and 17B show yet another variation of the imaging hood having at least two or more longitudinally positioned support members supporting the imaging hood membrane where the support members are movable relative to one another via a torquing or pulling or pushing force.
Figure 17B:
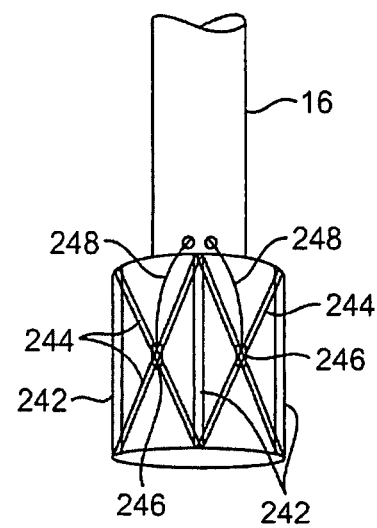

FIGS. 17A and 17B show yet another variation of imaging hood 240 having at least two or more longitudinally positioned support members 242 supporting the imaging hood membrane. The support members 242 each have cross-support members 244 which extend diagonally between and are pivotably attached to the support members 242. Each of the cross-support members 244 may be pivotably attached to one another where they intersect between the support members 242. A jack or screw member 246 may be coupled to each cross-support member 244 at this intersection point and a torquing member, such as a torqueable wire 248, may be coupled to each jack or screw member 246 and extend proximally through deployment catheter 16 to outside the patient body. From outside the patient body, the torqueable wires 248 may be torqued to turn the jack or screw member 246 which in turn urges the cross-support members 244 to angle relative to one another and thereby urge the support members 242 away from one another. Thus, the imaging hood 240 may be transitioned from its low-profile, shown in FIG. 17A, to its expanded profile, shown in FIG. 17B, and back into its low-profile by torquing wires 248.

Figure 18A:
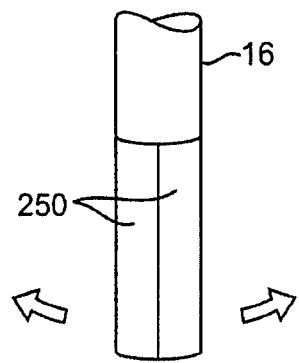
FIGS. 18A and 18B show another variation where a distal portion of the deployment catheter may have several pivoting members which form a tubular shape in its low profile configuration.
Figure 18B:
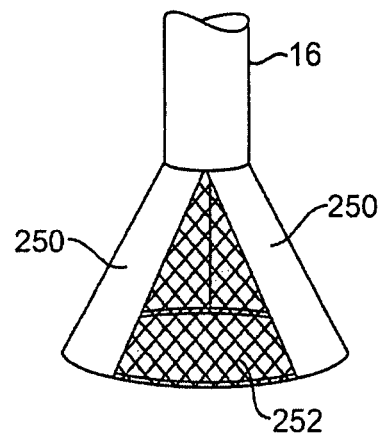

FIGS. 18A and 18B show yet another variation on the imaging hood and its deployment. As shown, a distal portion of deployment catheter 16 may have several pivoting members 250, e.g., two to four sections, which form a tubular shape in its low profile configuration, as shown in FIG. 18A. When pivoted radially about deployment catheter 16, pivoting members 250 may open into a deployed configuration having distensible or expanding membranes 252 extending over the gaps in-between the pivoting members 250, as shown in FIG. 18B. The distensible membrane 252 may be attached to the pivoting members 250 through various methods, e.g., adhesives, such that when the pivoting members 250 are fully extended into a conical shape, the pivoting members 250 and membrane 252 form a conical shape for use as an imaging hood. The distensible membrane 252 may be made out of a porous material such as a mesh or PTFE or out of a translucent or transparent polymer such as polyurethane, PVC, Nylon, etc.

Figure 19A:
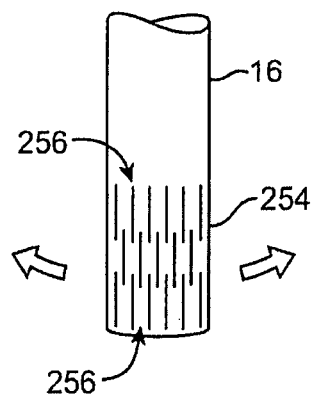
FIGS. 19A and 19B show another variation where the distal portion of deployment catheter may be fabricated from a flexible metallic or polymeric material to form a radially expanding hood.
Figure 19B:
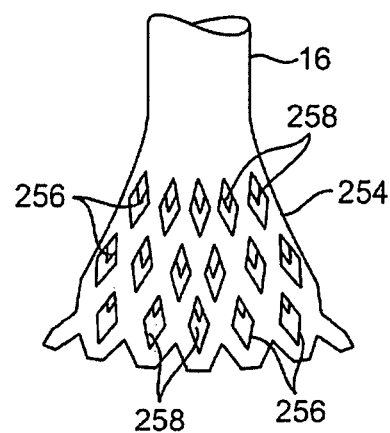

FIGS. 19A and 19B show yet another variation where the distal portion of deployment catheter 16 may be fabricated from a flexible metallic or polymeric material to form a radially expanding hood 254. A plurality of slots 256 may be formed in a uniform pattern over the distal portion of deployment catheter 16, as shown in FIG. 19A. The slots 256 may be formed in a pattern such that when the distal portion is urged radially open, utilizing any of the methods described above, a radially expanded and conically-shaped hood 254 may be formed by each of the slots 256 expanding into an opening, as shown in FIG. 19B. A distensible membrane 258 may overlie the exterior surface or the interior surface of the hood 254 to form a fluid-impermeable hood 254 such that the hood 254 may be utilized as an imaging hood. Alternatively, the distensible membrane 258 may alternatively be formed in each opening 258 to form the fluid-impermeable hood 254. Once the imaging procedure has been completed, hood 254 may be retracted into its low-profile configuration.

Figure 20A:
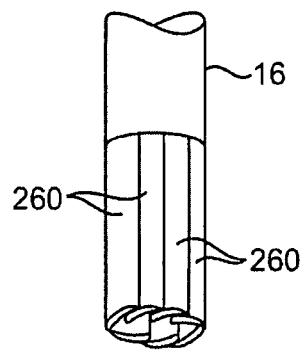
FIGS. 20A and 20B show another variation where the imaging hood may be formed from a plurality of overlapping hood members which overlie one another in an overlapping pattern.
Figure 20B:
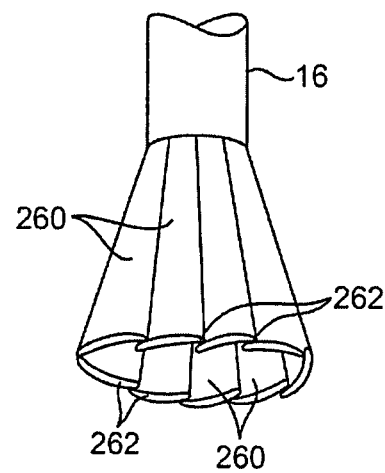

Yet another configuration for the imaging hood may be seen in FIGS. 20A and 20B where the imaging hood may be formed from a plurality of overlapping hood members 260 which overlie one another in an overlapping pattern. When expanded, each of the hood members 260 may extend radially outward relative to deployment catheter 16 to form a conically-shaped imaging hood, as shown in FIG. 20B. Adjacent hood members 260 may overlap one another along an overlapping interface 262 to form a fluid-retaining surface within the imaging hood. Moreover, the hood members 260 may be made from any number of biocompatible materials, e.g., Nitinol, stainless steel, polymers, etc., which are sufficiently strong to optionally retract surrounding tissue from the tissue region of interest.

Figure 21A:
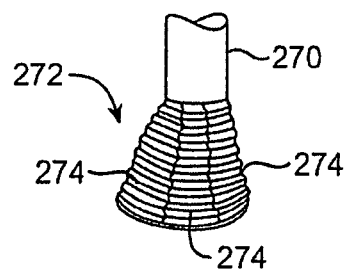
FIGS. 21A and 21B show another example of an expandable hood which is highly conformable against tissue anatomy with varying geography.
Figure 21B:
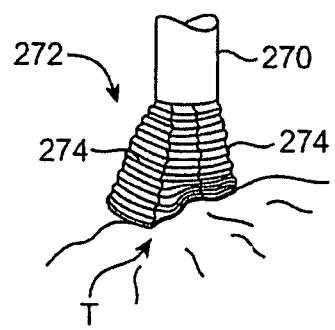

Although it is generally desirable to have an imaging hood contact against a tissue surface in a normal orientation, the imaging hood may be alternatively configured to contact the tissue surface at an acute angle. An imaging hood configured for such contact against tissue may also be especially suitable for contact against tissue surfaces having an unpredictable or uneven anatomical geography. For instance, as shown in the variation of FIG. 21A, deployment catheter 270 may have an imaging hood 272 that is configured to be especially compliant. In this variation, imaging hood 272 may be comprised of one or more sections 274 that are configured to fold or collapse, e.g., by utilizing a pleated surface. Thus, as shown in FIG. 21B, when imaging hood 272 is contacted against uneven tissue surface T, sections 274 are able to conform closely against the tissue. These sections 274 may be individually collapsible by utilizing an accordion style construction to allow conformation, e.g., to the trabeculae in the heart or the uneven anatomy that may be found inside the various body lumens.

Figure 22A:
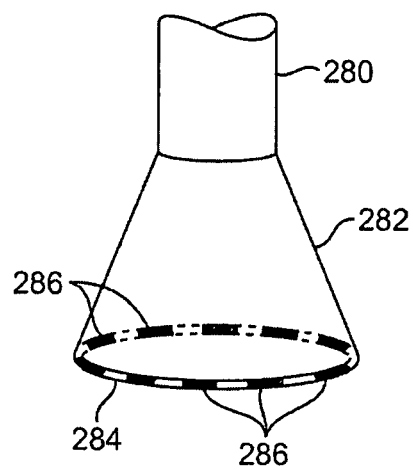
FIG. 22A shows yet another example of an expandable hood having a number of optional electrodes placed about the contact edge or lip of the hood for sensing tissue contact or detecting arrhythmias.

In yet another alternative, FIG. 22A shows another variation in which an imaging hood 282 is attached to deployment catheter 280. The contact lip or edge 284 may comprise one or more electrical contacts 286 positioned circumferentially around contact edge 284. The electrical contacts 286 may be configured to contact the tissue and indicate affirmatively whether tissue contact was achieved, e.g., by measuring the differential impedance between blood and tissue. Alternatively, a processor, e.g., processor 98, in electrical communication with contacts 286 may be configured to determine what type of tissue is in contact with electrical contacts 286. In yet another alternative, the processor 98 may be configured to measure any electrical activity that may be occurring in the underlying tissue, e.g., accessory pathways, for the purposes of electrically mapping the cardiac tissue and subsequently treating, as described below, any arrhythmias which may be detected.

Figure 22B:
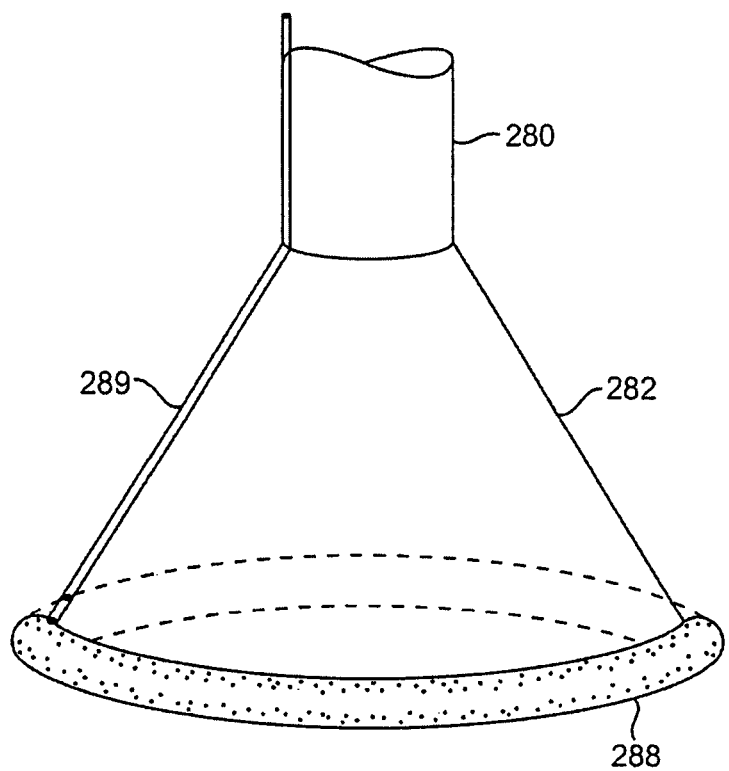
FIG. 22B shows another variation for conforming the imaging hood against the underlying tissue where an inflatable contact edge may be disposed around the circumference of the imaging hood.

Another variation for ensuring contact between imaging hood 282 and the underlying tissue may be seen in FIG. 22B. This variation may have an inflatable contact edge 288 around the circumference of imaging hood 282. The inflatable contact edge 288 may be inflated with a fluid or gas through inflation lumen 289 when the imaging hood 282 is to be placed against a tissue surface having an uneven or varied anatomy. The inflated circumferential surface 288 may provide for continuous contact over the hood edge by conforming against the tissue surface and facilitating imaging fluid retention within hood 282.

Figure 23:
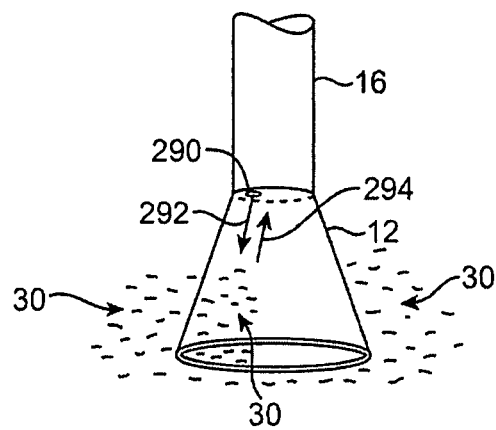
FIG. 23 shows a variation of the system which may be instrumented with a transducer for detecting the presence of blood seeping back into the imaging hood.

Aside from the imaging hood, various instrumentation may be utilized with the imaging and manipulation system. For instance, after the field within imaging hood 12 has been cleared of the opaque blood and the underlying tissue is visualized through the clear fluid, blood may seep back into the imaging hood 12 and obstruct the view. One method for automatically maintaining a clear imaging field may utilize a transducer, e.g., an ultrasonic transducer 290, positioned at the distal end of deployment catheter within the imaging hood 12, as shown in FIG. 23. The transducer 290 may send an energy pulse 292 into the imaging hood 12 and wait to detect back-scattered energy 294 reflected from debris or blood within the imaging hood 12. If back-scattered energy is detected, the pump may be actuated automatically to dispense more fluid into the imaging hood until the debris or blood is no longer detected.

Figure 24A:
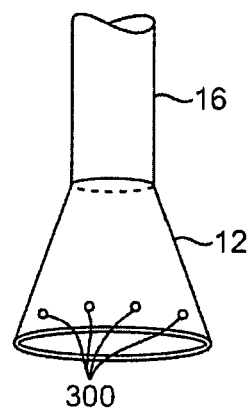
FIGS. 24A and 24B show variations of the imaging hood instrumented with sensors for detecting various physical parameters; the sensors may be instrumented around the outer surface of the imaging hood and also within the imaging hood.

Alternatively, one or more sensors 300 may be positioned on the imaging hood 12 itself, as shown in FIG. 24A, to detect a number of different parameters. For example, sensors 300 may be configured to detect for the presence of oxygen in the surrounding blood, blood and/or imaging fluid pressure, color of the fluid within the imaging hood, etc. Fluid color may be particularly useful in detecting the presence of blood within the imaging hood 12 by utilizing a reflective type sensor to detect back reflection from blood. Any reflected light from blood which may be present within imaging hood 12 may be optically or electrically transmitted through deployment catheter 16 and to a red colored filter within control electronics 118. Any red color which may be detected may indicate the presence of blood and trigger a signal to the physician or automatically actuate the pump to dispense more fluid into the imaging hood 12 to clear the blood.

Alternative methods for detecting the presence of blood within the hood 12 may include detecting transmitted light through the imaging fluid within imaging hood 12. If a source of white light, e.g., utilizing LEDs or optical fibers, is illuminated inside imaging hood 12, the presence of blood may cause the color red to be filtered through this fluid. The degree or intensity of the red color detected may correspond to the amount of blood present within imaging hood 12. A red color sensor can simply comprise, in one variation, a phototransistor with a red transmitting filter over it which can establish how much red light is detected, which in turn can indicate the presence of blood within imaging hood 12. Once blood is detected, the system may pump more clearing fluid through and enable closed loop feedback control of the clearing fluid pressure and flow level.

Figure 24B:
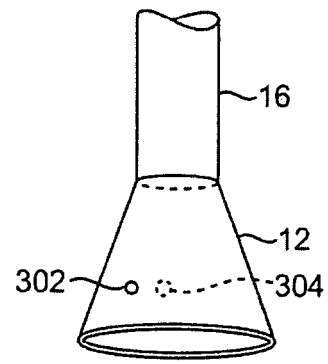

Any number of sensors may be positioned along the exterior 302 of imaging hood 12 or within the interior 304 of imaging hood 12 to detect parameters not only exteriorly to imaging hood 12 but also within imaging hood 12. Such a configuration, as shown in FIG. 24B, may be particularly useful for automatically maintaining a clear imaging field based upon physical parameters such as blood pressure, as described above for FIGS. 10A and 10B.

Figure 25A:
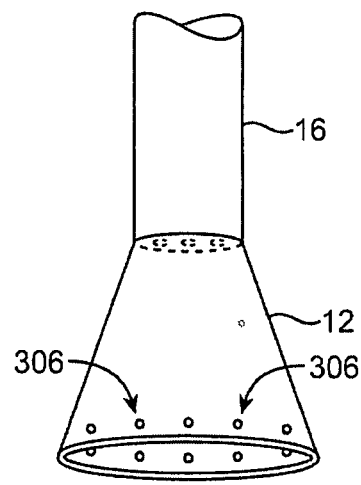
FIGS. 25A and 25B show a variation where the imaging hood may have one or more LEDs over the hood itself for providing illumination of the tissue to be visualized.
Figure 25B:
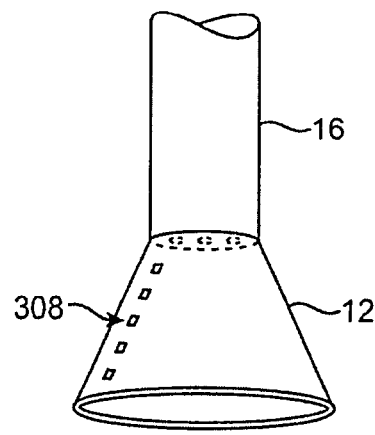

Aside from sensors, one or more light emitting diodes (LEDs) may be utilized to provide lighting within the imaging hood 12. Although illumination may be provided by optical fibers routed through deployment catheter 16, the use of LEDs over the imaging hood 12 may eliminate the need for additional optical fibers for providing illumination. The electrical wires connected to the one or more LEDs may be routed through or over the hood 12 and along an exterior surface or extruded within deployment catheter 16. One or more LEDs may be positioned in a circumferential pattern 306 around imaging hood 12, as shown in FIG. 25A, or in a linear longitudinal pattern 308 along imaging hood 12, as shown in FIG. 25B. Other patterns, such as a helical or spiral pattern, may also be utilized. Alternatively, LEDs may be positioned along a support member forming part of imaging hood 12.

Figure 26A:
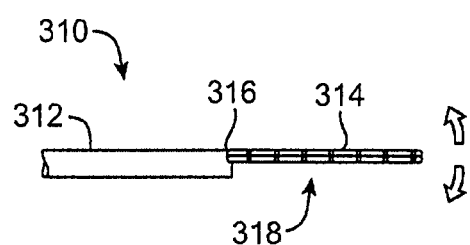
FIGS. 26A and 26B show another variation in which a separate illumination tool having one or more LEDs mounted thereon may be utilized within the imaging hood.
Figure 26B:
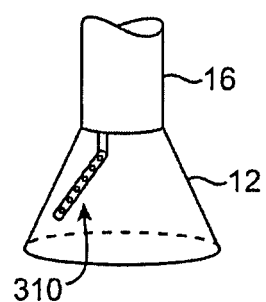

In another alternative for illumination within imaging hood 12, a separate illumination tool 310 may be utilized, as shown in FIG. 26A. An example of such a tool may comprise a flexible intravascular delivery member 312 having a carrier member 314 pivotably connected 316 to a distal end of delivery member 312. One or more LEDs 318 may be mounted along carrier member 314. In use, delivery member 312 may be advanced through deployment catheter 16 until carrier member 314 is positioned within imaging hood 12. Once within imaging hood 12, carrier member 314 may be pivoted in any number of directions to facilitate or optimize the illumination within the imaging hood 12, as shown in FIG. 26B.

In utilizing LEDs for illumination, whether positioned along imaging hood 12 or along a separate instrument, the LEDs may comprise a single LED color, e.g., white light. Alternatively, LEDs of other colors, e.g., red, blue, yellow, etc., may be utilized exclusively or in combination with white LEDs to provide for varied illumination of the tissue or fluids being imaged. Alternatively, sources of infrared or ultraviolet light may be employed to enable imaging beneath the tissue surface or cause fluorescence of tissue for use in system guidance, diagnosis, or therapy.

Figure 27:
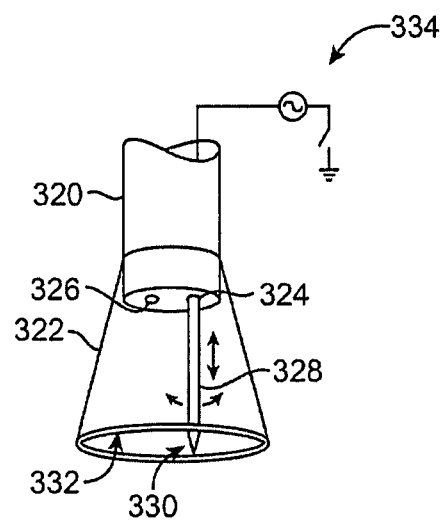
FIG. 27 shows one example of how a therapeutic tool may be advanced through the tissue imager for treating a tissue region of interest.

Aside from providing a visualization platform, the imaging assembly may also be utilized to provide a therapeutic platform for treating tissue being visualized. As shown in FIG. 27, deployment catheter 320 may have imaging hood 322, as described above, and fluid delivery lumen 324 and imaging lumen 326. In this variation, a therapeutic tool such as needle 328 may be delivered through fluid delivery lumen 324 or in another working lumen and advanced through open area 332 for treating the tissue which is visualized. In this instance, needle 328 may define one or several ports 330 for delivering drugs therethrough. Thus, once the appropriate region of tissue has been imaged and located, needle 328 may be advanced and pierced into the underlying tissue where a therapeutic agent may be delivered through ports 330. Alternatively, needle 328 may be in electrical communication with a power source 334, e.g., radio-frequency, microwave, etc., for ablating the underlying tissue area of interest.

Figure 28:
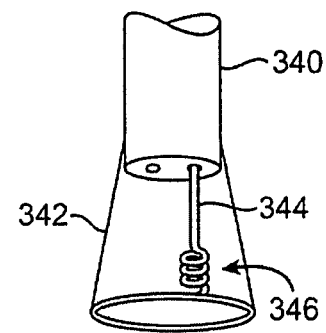
FIG. 28 shows another example of a helical therapeutic tool for treating the tissue region of interest.

FIG. 28 shows another alternative in which deployment catheter 340 may have imaging hood 342 attached thereto, as above, but with a therapeutic tool 344 in the configuration of a helical tissue piercing device 344. Also shown and described above in FIGS. 7A and 7B for use in stabilizing the imaging hood relative to the underlying tissue, the helical tissue piercing device 344 may also be utilized to manipulate the tissue for a variety of therapeutic procedures. The helical portion 346 may also define one or several ports for delivery of therapeutic agents therethrough.

Figure 29:
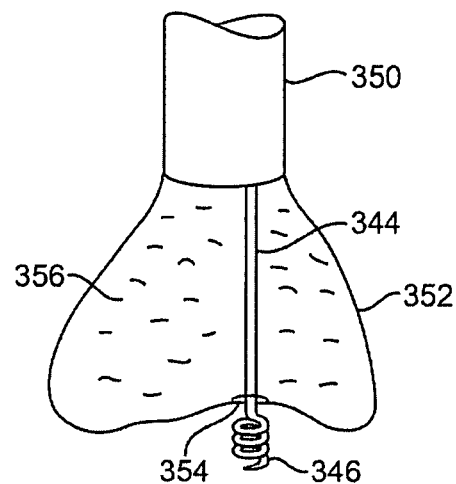
FIG. 29 shows a variation of how a therapeutic tool may be utilized with an expandable imaging balloon.

In yet another alternative, FIG. 29 shows a deployment catheter 350 having an expandable imaging balloon 352 filled with, e.g., saline 356. A therapeutic tool 344, as above, may be translatable relative to balloon 352. To prevent the piercing portion 346 of the tool from tearing balloon 352, a stop 354 may be formed on balloon 352 to prevent the proximal passage of portion 346 past stop 354.

Figure 30A:
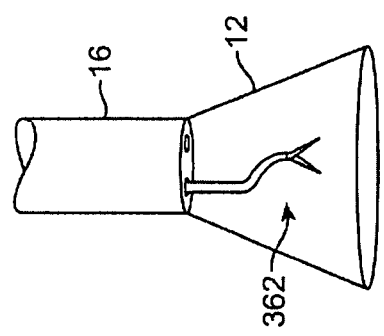
FIGS. 30A and 30B show alternative configurations for therapeutic instruments which may be utilized; one variation is shown having an angled instrument arm and another variation is shown with an off-axis instrument arm.
Figure 30B:
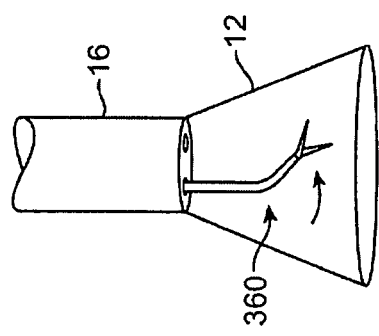

Alternative configurations for tools which may be delivered through deployment catheter 16 for use in tissue manipulation within imaging hood 12 are shown in FIGS. 30A and 30B. FIG. 30A shows one variation of an angled instrument 360, such as a tissue grasper, which may be configured to have an elongate shaft for intravascular delivery through deployment catheter 16 with a distal end which may be angled relative to its elongate shaft upon deployment into imaging hood 12. The elongate shaft may be configured to angle itself automatically, e.g., by the elongate shaft being made at least partially from a shape memory alloy, or upon actuation, e.g., by tensioning a pullwire. FIG. 30B shows another configuration for an instrument 362 being configured to reconfigure its distal portion into an off-axis configuration within imaging hood 12. In either case, the instruments 360, 362 may be reconfigured into a low-profile shape upon withdrawing them proximally back into deployment catheter 16.

Figure 31A:
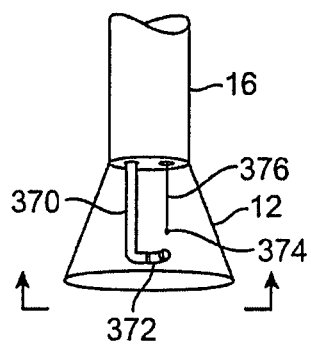
FIGS. 31A to 31C show side and end views, respectively, of an imaging system which may be utilized with an ablation probe.
Figure 31B:
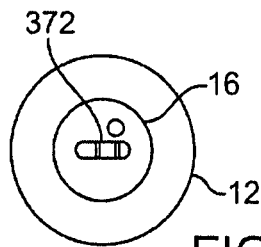
Figure 31C:
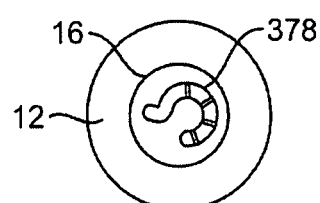

Other instruments or tools which may be utilized with the imaging system is shown in the side and end views of FIGS. 31A to 31C. FIG. 31A shows a probe 370 having a distal end effector 372, which may be reconfigured from a low-profile shape to a curved profile. The end effector 372 may be configured as an ablation probe utilizing radio-frequency energy, microwave energy, ultrasound energy, laser energy or even cryo-ablation. Alternatively, the end effector 372 may have several electrodes upon it for detecting or mapping electrical signals transmitted through the underlying tissue.

In the case of an end effector 372 utilized for ablation of the underlying tissue, an additional temperature sensor such as a thermocouple or thermistor 374 positioned upon an elongate member 376 may be advanced into the imaging hood 12 adjacent to the distal end effector 372 for contacting and monitoring a temperature of the ablated tissue. FIG. 31B shows an example in the end view of one configuration for the distal end effector 372 which may be simply angled into a perpendicular configuration for contacting the tissue. FIG. 31C shows another example where the end effector may be reconfigured into a curved end effector 378 for increased tissue contact.

Figure 32A:
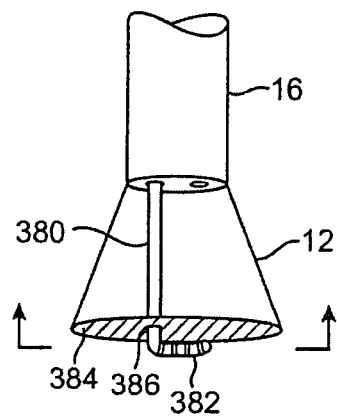
FIGS. 32A and 32B show side and end views, respectively, of another variation of the imaging hood with an ablation probe, where the imaging hood may be enclosed for regulating a temperature of the underlying tissue.
Figure 32B:
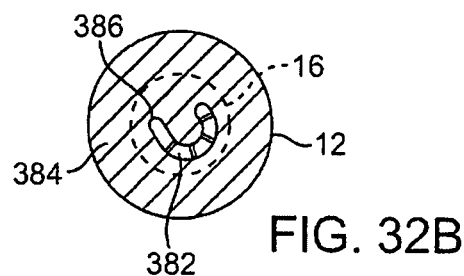

FIGS. 32A and 32B show another variation of an ablation tool utilized with an imaging hood 12 having an enclosed bottom portion. In this variation, an ablation probe, such as a cryo-ablation probe 380 having a distal end effector 382, may be positioned through the imaging hood 12 such that the end effector 382 is placed distally of a transparent membrane or enclosure 384, as shown in the end view of FIG. 32B. The shaft of probe 380 may pass through an opening 386 defined through the membrane 384. In use, the clear fluid may be pumped into imaging hood 12, as described above, and the distal end effector 382 may be placed against a tissue region to be ablated with the imaging hood 12 and the membrane 384 positioned atop or adjacent to the ablated tissue. In the case of cryo-ablation, the imaging fluid may be warmed prior to dispensing into the imaging hood 12 such that the tissue contacted by the membrane 384 may be warmed during the cryo-ablation procedure. In the case of thermal ablation, e.g., utilizing radio-frequency energy, the fluid dispensed into the imaging hood 12 may be cooled such that the tissue contacted by the membrane 384 and adjacent to the ablation probe during the ablation procedure is likewise cooled.

Figure 33A:
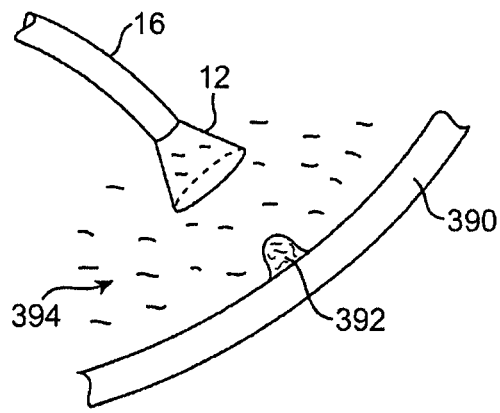
FIGS. 33A and 33B show an example in which the imaging fluid itself may be altered in temperature to facilitate various procedures upon the underlying tissue.
Figure 33B:
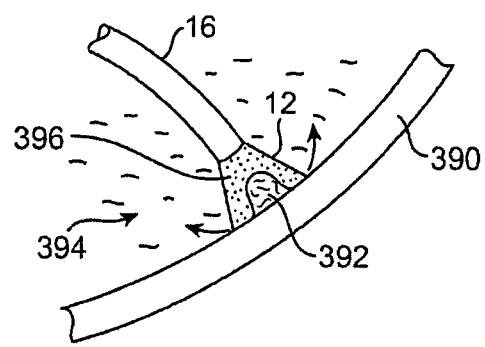

In either example described above, the imaging fluid may be varied in its temperature to facilitate various procedures to be performed upon the tissue. In other cases, the imaging fluid itself may be altered to facilitate various procedures. For instance as shown in FIG. 33A, a deployment catheter 16 and imaging hood 12 may be advanced within a hollow body organ, such as a bladder filled with urine 394, towards a lesion or tumor 392 on the bladder wall. The imaging hood 12 may be placed entirely over the lesion 392, or over a portion of the lesion. Once secured against the tissue wall 390, a cryo-fluid, i.e., a fluid which has been cooled to below freezing temperatures of, e.g., water or blood, may be pumped into the imaging hood 12 to cryo-ablate the lesion 390, as shown in FIG. 33B while avoiding the creation of ice on the instrument or surface of tissue.

As the cryo-fluid leaks out of the imaging hood 12 and into the organ, the fluid may be warmed naturally by the patient body and ultimately removed. The cryo-fluid may be a colorless and translucent fluid which enables visualization therethrough of the underlying tissue. An example of such a fluid is Fluorinert™ (3M, St. Paul, Minn.), which is a colorless and odorless perfluorinated liquid. The use of a liquid such as Fluorinert™ enables the cryo-ablation procedure without the formation of ice within or outside of the imaging hood 12. Alternatively, rather than utilizing cryo-ablation, hyperthermic treatments may also be effected by heating the Fluorinert™ liquid to elevated temperatures for ablating the lesion 392 within the imaging hood 12. Moreover, Fluorinert™ may be utilized in various other parts of the body, such as within the heart.

Figure 34A:
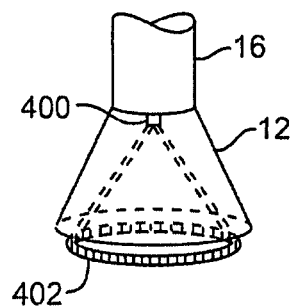
FIGS. 34A and 34B show an example of a laser ring generator which may be utilized with the imaging system and an example for applying the laser ring generator within the left atrium of a heart for treating atrial fibrillation.

FIG. 34A shows another variation of an instrument which may be utilized with the imaging system. In this variation, a laser ring generator 400 may be passed through the deployment catheter 16 and partially into imaging hood 12. A laser ring generator 400 is typically used to create a circular ring of laser energy 402 for generating a conduction block around the pulmonary veins typically in the treatment of atrial fibrillation. The circular ring of laser energy 402 may be generated such that a diameter of the ring 402 is contained within a diameter of the imaging hood 12 to allow for tissue ablation directly upon tissue being imaged. Signals which cause atrial fibrillation typically come from the entry area of the pulmonary veins into the left atrium and treatments may sometimes include delivering ablation energy to the ostia of the pulmonary veins within the atrium. The ablated areas of the tissue may produce a circular scar which blocks the impulses for atrial fibrillation.

When using the laser energy to ablate the tissue of the heart, it may be generally desirable to maintain the integrity and health of the tissue overlying the surface while ablating the underlying tissue. This may be accomplished, for example, by cooling the imaging fluid to a temperature below the body temperature of the patient but which is above the freezing point of blood (e.g., 2° C. to 35° C.). The cooled imaging fluid may thus maintain the surface tissue at the cooled fluid temperature while the deeper underlying tissue remains at the patient body temperature. When the laser energy (or other types of energy such as radio frequency energy, microwave energy, ultrasound energy, etc.) irradiates the tissue, both the cooled tissue surface as well as the deeper underlying tissue will rise in temperature uniformly. The deeper underlying tissue, which was maintained at the body temperature, will increase to temperatures which are sufficiently high to destroy the underlying tissue. Meanwhile, the temperature of the cooled surface tissue will also rise but only to temperatures that are near body temperature or slightly above.

Figure 34B:
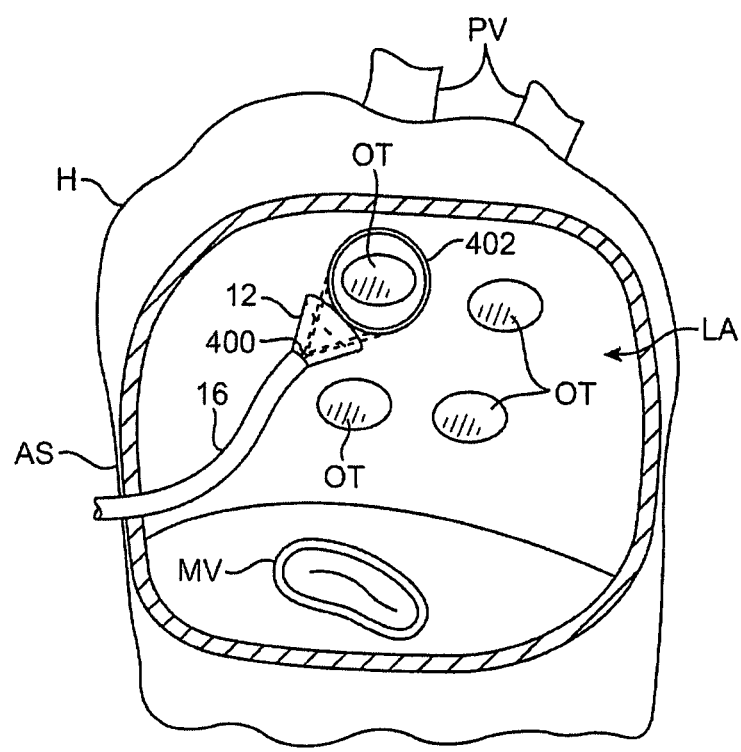

Accordingly, as shown in FIG. 34B, one example for treatment may include passing deployment catheter 16 across the atrial septum AS and into the left atrium LA of the patient's heart H. Other methods of accessing the left atrium LA may also be utilized. The imaging hood 12 and laser ring generator 400 may be positioned adjacent to or over one or more of the ostium OT of the pulmonary veins PV and the laser generator 400 may ablate the tissue around the ostium OT with the circular ring of laser energy 402 to create a conduction block. Once one or more of the tissue around the ostium OT have been ablated, the imaging hood 12 may be reconfigured into a low profile for removal from the patient heart H.

One of the difficulties in treating tissue in or around the ostium OT is the dynamic fluid flow of blood through the ostium OT. The dynamic forces make cannulation or entry of the ostium OT difficult. Thus, another variation on instruments or tools utilizable with the imaging system is an extendible cannula 410 having a cannula lumen 412 defined therethrough, as shown in FIG. 35A. The extendible cannula 410 may generally comprise an elongate tubular member which may be positioned within the deployment catheter 16 during delivery and then projected distally through the imaging hood 12 and optionally beyond, as shown in FIG. 35B.

In use, once the imaging hood 12 has been desirably positioned relative to the tissue, e.g., as shown in FIG. 35C outside the ostium OT of a pulmonary vein PV, the extendible cannula 410 may be projected distally from the deployment catheter 16 while optionally imaging the tissue through the imaging hood 12, as described above. The extendible cannula 410 may be projected distally until its distal end is extended at least partially into the ostium OT. Once in the ostium OT, an instrument or energy ablation device may be extended through and out of the cannula lumen 412 for treatment within the ostium OT. Upon completion of the procedure, the cannula 410 may be withdrawn proximally and removed from the patient body. The extendible cannula 410 may also include an inflatable occlusion balloon at or near its distal end to block the blood flow out of the PV to maintain a clear view of the tissue region. Alternatively, the extendible cannula 410 may define a lumen therethrough beyond the occlusion balloon to bypass at least a portion of the blood that normally exits the pulmonary vein PV by directing the blood through the cannula 410 to exit proximal of the imaging hood.

Figure 36A:
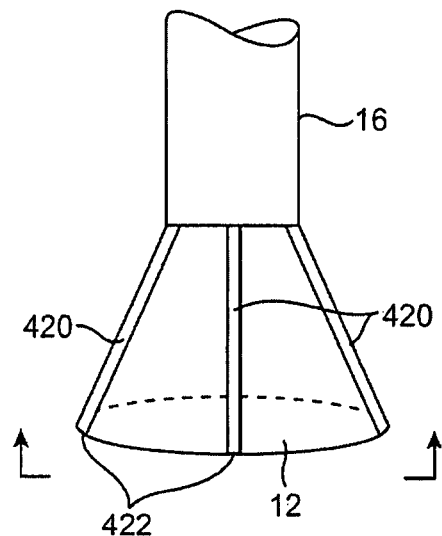
FIGS. 36A and 36B show side and end views, respectively, of an imaging hood having one or more tubular support members integrated with the hood for passing instruments or tools therethrough for treatment upon the underlying tissue.
Figure 36B:
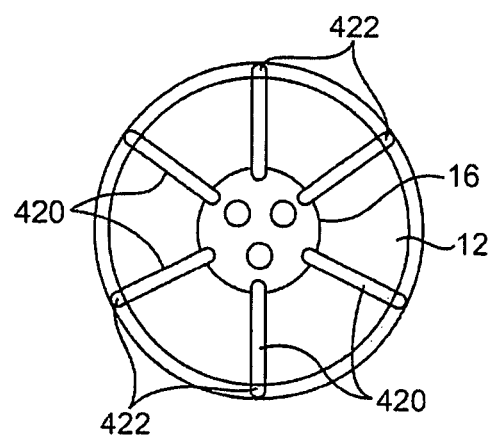

Yet another variation for tool or instrument use may be seen in the side and end views of FIGS. 36A and 36B. In this variation, imaging hood 12 may have one or more tubular support members 420 integrated with the hood 12. Each of the tubular support members 420 may define an access lumen 422 through which one or more instruments or tools may be delivered for treatment upon the underlying tissue. One particular example is shown and described above for FIG. 7C.

Figure 37A:
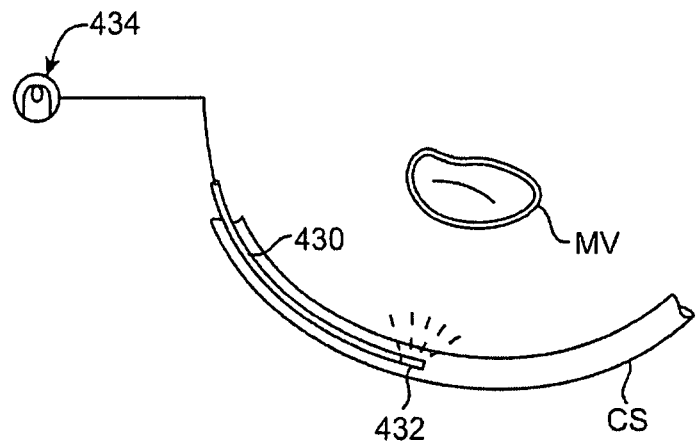
FIGS. 37A and 37B illustrate how an imaging device may be guided within a heart chamber to a region of interest utilizing a lighted probe positioned temporarily within, e.g., a lumen of the coronary sinus.
Figure 37B:
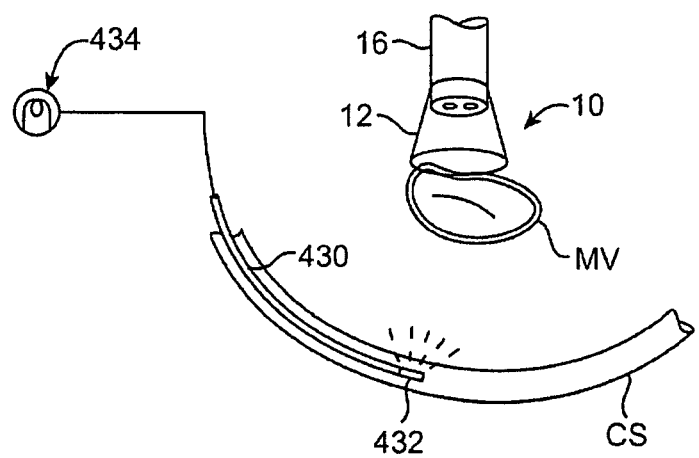

Various methods and instruments may be utilized for using or facilitating the use of the system. For instance, one method may include facilitating the initial delivery and placement of a device into the patient's heart. In initially guiding the imaging assembly within the heart chamber to, e.g., the mitral valve MV, a separate guiding probe 430 may be utilized, as shown in FIGS. 37A and 37B. Guiding probe 430 may, for example, comprise an optical fiber through which a light source 434 may be used to illuminate a distal tip portion 432. The tip portion 432 may be advanced into the heart through, e.g., the coronary sinus CS, until the tip is positioned adjacent to the mitral valve MV. The tip 432 may be illuminated, as shown in FIG. 37A, and imaging assembly 10 may then be guided towards the illuminated tip 432, which is visible from within the atrial chamber, towards mitral valve MV.

Figure 38A:
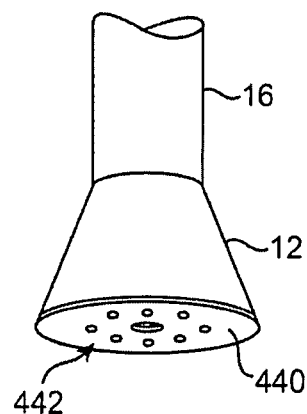
FIGS. 38A and 38B show an imaging hood having a removable disk-shaped member for implantation upon the tissue surface.
Figure 38B:
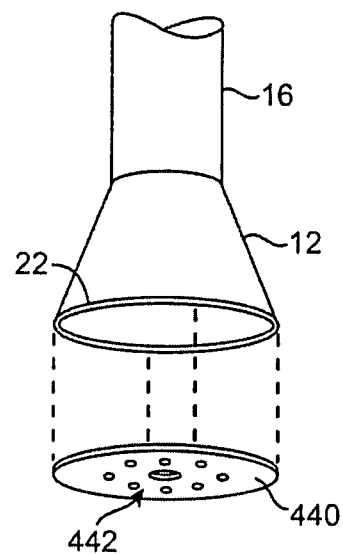

Aside from the devices and methods described above, the imaging system may be utilized to facilitate various other procedures. Turning now to FIGS. 38A and 38B, the imaging hood of the device in particular may be utilized. In this example, a collapsible membrane or disk-shaped member 440 may be temporarily secured around the contact edge or lip of imaging hood 12. During intravascular delivery, the imaging hood 12 and the attached member 440 may both be in a collapsed configuration to maintain a low profile for delivery. Upon deployment, both the imaging hood 12 and the member 440 may extend into their expanded configurations.

The disk-shaped member 440 may be comprised of a variety of materials depending upon the application. For instance, member 440 may be fabricated from a porous polymeric material infused with a drug eluting medicament 442 for implantation against a tissue surface for slow infusion of the medicament into the underlying tissue. Alternatively, the member 440 may be fabricated from a non-porous material, e.g., metal or polymer, for implantation and closure of a wound or over a cavity to prevent fluid leakage. In yet another alternative, the member 440 may be made from a distensible material which is secured to imaging hood 12 in an expanded condition. Once implanted or secured on a tissue surface or wound, the expanded member 440 may be released from imaging hood 12. Upon release, the expanded member 440 may shrink to a smaller size while approximating the attached underlying tissue, e.g., to close a wound or opening.

One method for securing the disk-shaped member 440 to a tissue surface may include a plurality of tissue anchors 444, e.g., barbs, hooks, projections, etc., which are attached to a surface of the member 440. Other methods of attachments may include adhesives, suturing, etc. In use, as shown in FIGS. 39A to 39C, the imaging hood 12 may be deployed in its expanded configuration with member 440 attached thereto with the plurality of tissue anchors 444 projecting distally. The tissue anchors 444 may be urged into a tissue region to be treated 446, as seen in FIG. 39A, until the anchors 444 are secured in the tissue and member 440 is positioned directly against the tissue, as shown in FIG. 39B. A pullwire may be actuated to release the member 440 from the imaging hood 12 and deployment catheter 16 may be withdrawn proximally to leave member 440 secured against the tissue 446.

Figure 40A:
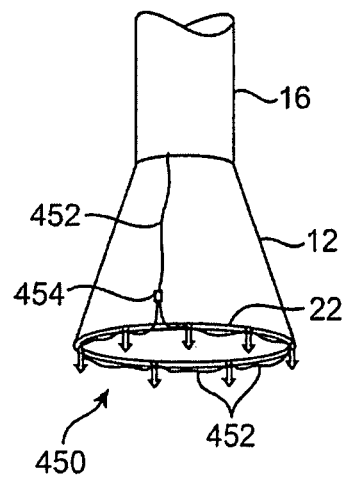
FIGS. 40A and 40B illustrate an imaging hood having a deployable anchor assembly attached to the tissue contact edge and an assembly view of the anchors and the suture or wire connected to the anchors, respectively
Figure 40B:
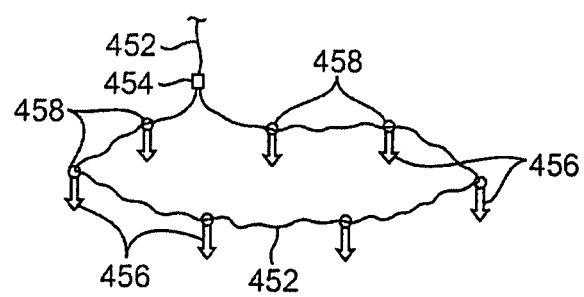

Another variation for tissue manipulation and treatment may be seen in the variation of FIG. 40A, which illustrates an imaging hood 12 having a deployable anchor assembly 450 attached to the tissue contact edge 22. FIG. 40B illustrates the anchor assembly 450 detached from the imaging hood 12 for clarity. The anchor assembly 450 may be seen as having a plurality of discrete tissue anchors 456, e.g., barbs, hooks, projections, etc., each having a suture retaining end, e.g., an eyelet or opening 458 in a proximal end of the anchors 456. A suture member or wire 452 may be slidingly connected to each anchor 456 through the openings 458 and through a cinching element 454, which may be configured to slide uni-directionally over the suture or wire 452 to approximate each of the anchors 456 towards one another. Each of the anchors 456 may be temporarily attached to the imaging hood 12 through a variety of methods. For instance, a pullwire or retaining wire may hold each of the anchors within a receiving ring around the circumference of the imaging hood 12. When the anchors 456 are released, the pullwire or retaining wire may be tensioned from its proximal end outside the patient body to thereby free the anchors 456 from the imaging hood 12.

One example for use of the anchor assembly 450 is shown in FIGS. 41A to 41D for closure of an opening or wound 460, e.g., patent foramen ovale (PFO). The deployment catheter 16 and imaging hood 12 may be delivered intravascularly into, e.g., a patient heart. As the imaging hood 12 is deployed into its expanded configuration, the imaging hood 12 may be positioned adjacent to the opening or wound 460, as shown in FIG. 41A. With the anchor assembly 450 positioned upon the expanded imaging hood 12, deployment catheter 16 may be directed to urge the contact edge of imaging hood 12 and anchor assembly 450 into the region surrounding the tissue opening 460, as shown in FIG. 41B. Once the anchor assembly 450 has been secured within the surrounding tissue, the anchors may be released from imaging hood 12 leaving the anchor assembly 450 and suture member 452 trailing from the anchors, as shown in FIG. 41C. The suture or wire member 452 may be tightened by pulling it proximally from outside the patient body to approximate the anchors of anchor assembly 450 towards one another in a purse-string manner to close the tissue opening 462, as shown in FIG. 41D. The cinching element 454 may also be pushed distally over the suture or wire member 452 to prevent the approximated anchor assembly 450 from loosening or widening.

Figure 42:
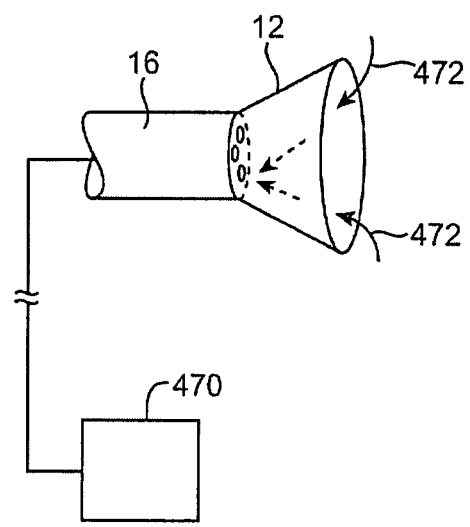
FIG. 42 shows another variation in which the imaging system may be fluidly coupled to a dialysis unit for filtering a patient's blood.

Another example for an alternative use is shown in FIG. 42, where the deployment catheter 16 and deployed imaging hood 12 may be positioned within a patient body for drawing blood 472 into deployment catheter 16. The drawn blood 472 may be pumped through a dialysis unit 470 located externally of the patient body for filtering the drawn blood 472 and the filtered blood may be reintroduced back into the patient.

Figure 43A:
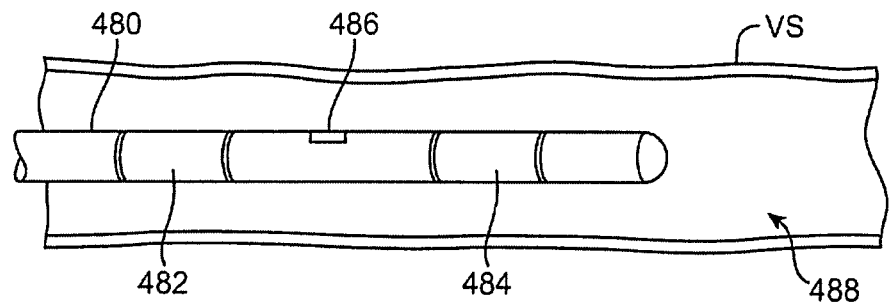
FIGS. 43A and 43B show a variation of the deployment catheter having a first deployable hood and a second deployable hood positioned distal to the first hood; the deployment catheter may also have a side-viewing imaging element positioned between the first and second hoods for imaging tissue between the expanded hoods.
Figure 43B:
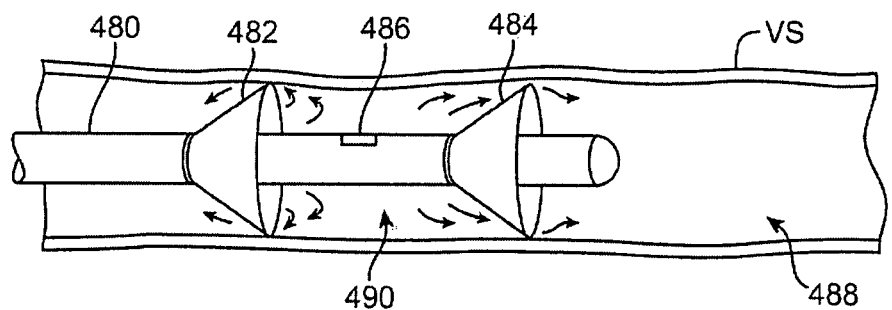

Yet another variation is shown in FIGS. 43A and 43B, which show a variation of the deployment catheter 480 having a first deployable hood 482 and a second deployable hood 484 positioned distal to the first hood 482. The deployment catheter 480 may also have a side-viewing imaging element 486 positioned between the first and second hoods 482, 484 along the length of the deployment catheter 480. In use, such a device may be introduced through a lumen 488 of a vessel VS, where one or both hoods 482, 484 may be expanded to gently contact the surrounding walls of vessel VS. Once hoods 482, 484 have been expanded, the clear imaging fluid may be pumped in the space defined between the hoods 482, 484 to displace any blood and to create an imaging space 490, as shown in FIG. 43B. With the clear fluid in-between hoods 482, 484, the imaging element 486 may be used to view the surrounding tissue surface contained between hoods 482, 484. Other instruments or tools may be passed through deployment catheter 480 and through one or more openings defined along the catheter 480 for additionally performing therapeutic procedures upon the vessel wall.

Another variation of a deployment catheter 500 which may be used for imaging tissue to the side of the instrument may be seen in FIGS. 44A to 45B. FIGS. 44A and 44B show side and end views of deployment catheter 500 having a side-imaging balloon 502 in an un-inflated low-profile configuration. A side-imaging element 504 may be positioned within a distal portion of the catheter 500 where the balloon 502 is disposed. When balloon 502 is inflated, it may expand radially to contact the surrounding tissue, but where the imaging element 504 is located, a visualization field 506 may be created by the balloon 502, as shown in the side, top, and end views of FIGS. 45A to 45B, respectively. The visualization field 506 may simply be a cavity or channel which is defined within the inflated balloon 502 such that the visualization element 504 is provided an image of the area within field 506 which is clear and unobstructed by balloon 502.

Figure 46B:
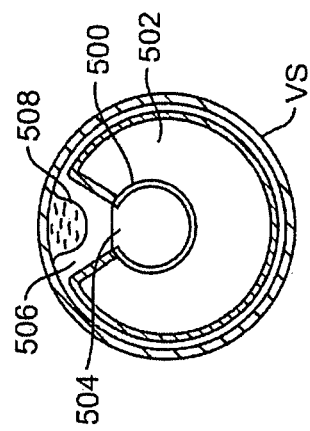
FIGS. 46A and 46B show side and cross-sectional end views, respectively, for one method of use in visualizing a lesion upon a vessel wall within the visualization field of the inflated balloon from FIGS. 45A to 45C.
Figure 46A:
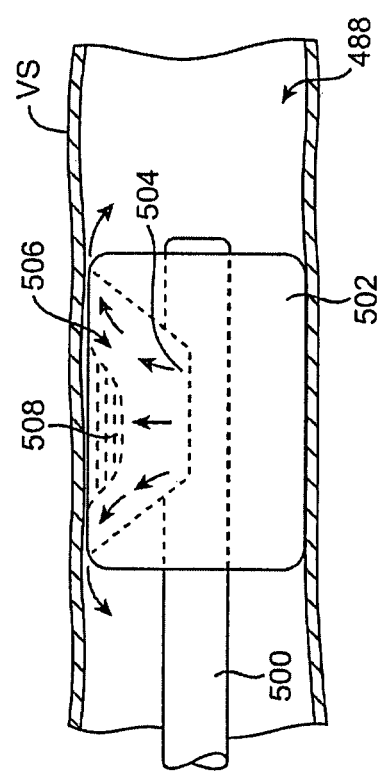

In use, deployment catheter 500 may be advanced intravascularly through vessel lumen 488 towards a lesion or tumor 508 to be visualized and/or treated. Upon reaching the lesion 508, deployment catheter 500 may be positioned adjacently to the lesion 508 and balloon 502 may be inflated such that the lesion 508 is contained within the visualization field 506. Once balloon 502 is fully inflated and in contact against the vessel wall, clear fluid may be pumped into visualization field 506 through deployment catheter 500 to displace any blood or opaque fluids from the field 506, as shown in the side and end views of FIGS. 46A and 46B, respectively. The lesion 508 may then be visually inspected and treated by passing any number of instruments through deployment catheter 500 and into field 506.

In additional variations of the imaging hood and deployment catheter, the various assemblies may be configured in particular for crossing through a septal wall, e.g., the atrial septum AS, for trans-septally accessing an atrial chamber such as the left atrium LA, also as illustrated above in FIG. 5, while under direct visualization. In particular, the devices and assemblies may be configured to facilitate passage across the atrial septum AS from the right atrium RA to the left atrium LA.

Figure 47A:
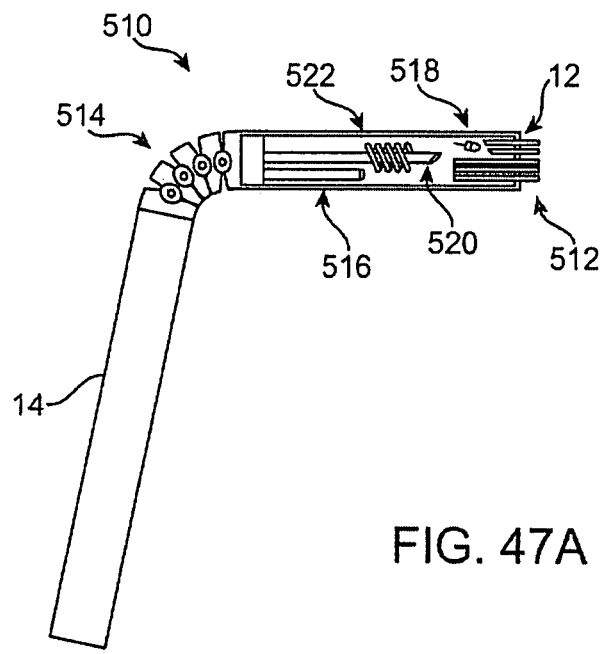
FIG. 47A shows a partial cross-sectional side view of an imaging hood assembly in its low-profile configuration within an outer sheath.

One variation of assembly 510 is illustrated in the partial cross-sectional side view in FIG. 47A, which shows some of the components of imaging hood assembly 512 contained in its low-profile configuration within sheath 14. An articulatable/steerable section 514 may optionally be defined near or at a distal portion of sheath 14 to provide steering capabilities for hood assembly 512. Steering may be accomplished via one or more push-pull wires routed through one or more steering lumens. Alternatively, articulatable/steerable section 514 may be comprised of several links which are serially aligned and pivotably connected to one another such that one or more steering wires passing through the links and controlled via their proximal ends from outside the patient body may be variously tensioned to effect steering of the links. The individual links may accordingly comprise pin links, bump links, etc. to provide at least for steering in a planar motion. Adjacent links which are pivotably coupled to one another in a single plane may be alternated with links which are pivotably coupled to one another in a transverse plane such that the section 514 and imaging hood 12 may be articulated and steered in multiple planes relative to the deployment catheter 16 or sheath 14. Also contained within hood 12 is an off-axis imaging element 518, as described above as a CCD or CMOS imager, mounted along the hood interior as well as piercing needle 520, which may further define one or more tissue engaging features 522, e.g., helical screw or threads, proximal to the piercing tip for facilitating tissue engagement. Additionally, flushing port 516 may also be included to provide for fluid introduction within the hood 12 when the surrounding blood is to be flushed or purged out from the hood 12 to provide the clear viewing field, as described above.

Figure 47B:
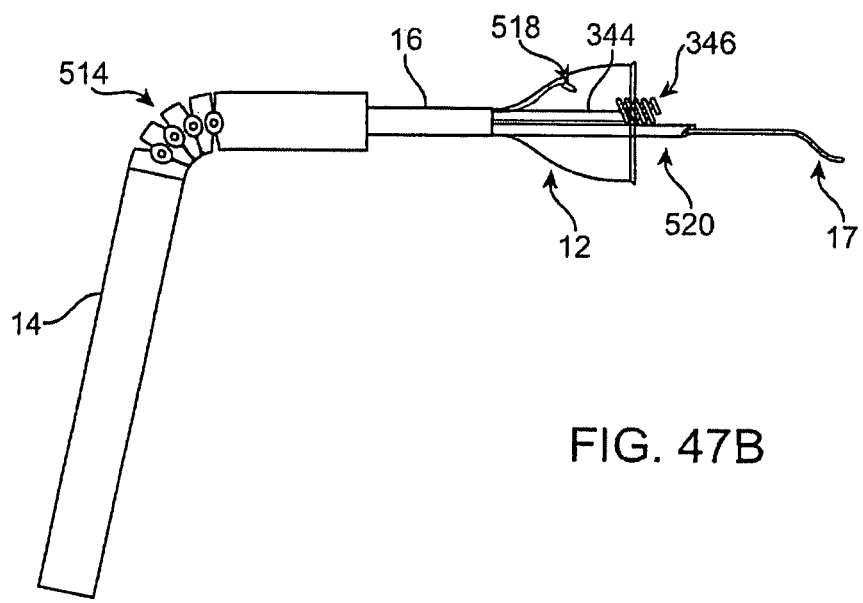
FIG. 47B shows a partial cross-sectional side view of another variation of the imaging hood having a piercing instrument with a guidewire passed therethrough.

When deployed, imaging hood 12 may be advanced via deployment catheter 16 distally of sheath 14, whereupon hood 12 may be expanded into its deployed configuration, as shown in FIG. 47B, where imaging element 518 is positioned off-axis relative to a longitudinal axis of catheter 16. Once a targeted region of tissue, such as the atrial septum AS, has been engaged by the helical portion 346 of tissue piercing device 344 and needle 520 has been advanced to pierce through the tissue wall, guidewire 17 may be advanced through a lumen defined within needle 520 into the atrial chamber, as described in further detail below.

Figure 47C:
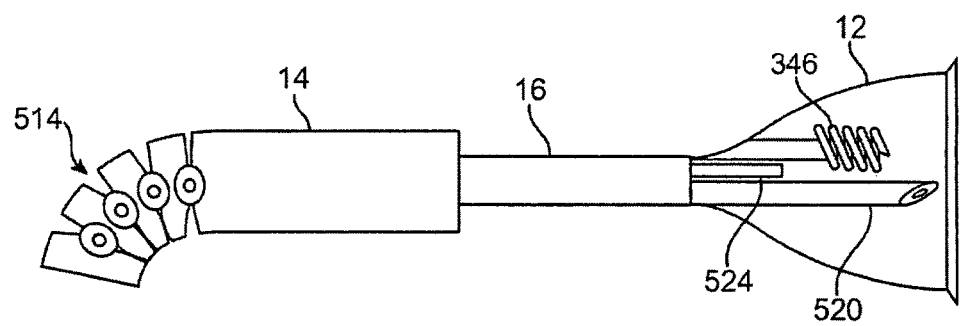
FIG. 47C shows a variation of an expanded imaging hood having an optical imaging element, e.g., one or more optical fiber bundles.
Figure 47D:
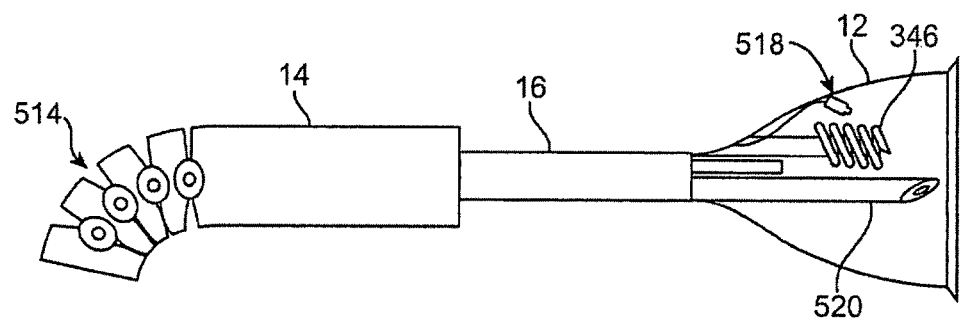
FIG. 47D shows another variation of an expanded imaging hood having an off-axis electronic imaging element.

Another variation is illustrated in the side view of FIG. 47C where imaging hood 12 has been expanded and an optical imaging element 524, e.g., one or more optical fiber bundles, may be positioned within a lumen of catheter 16 to provide for direct in-line visualization. FIG. 47D further illustrates the variation of imaging element 518 configured as an electronic imager, as above, with the piercing needle 520 for passing into or through a tissue region such as the septal wall and the tissue engager 346 grabbing and maintaining the tissue region relative to hood 12.

Figure 48A:
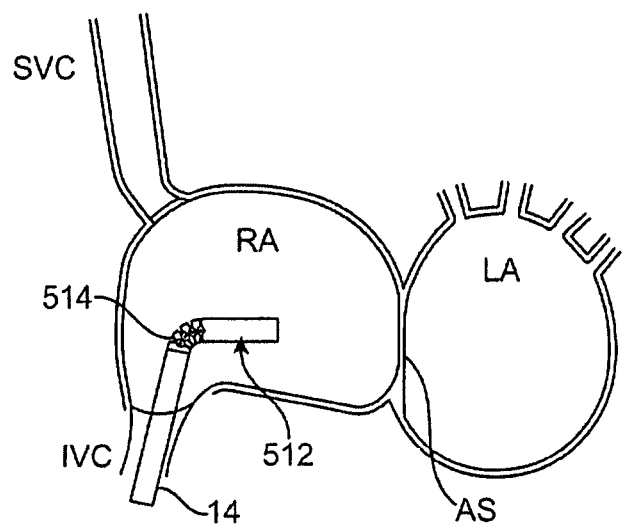
FIGS. 48A to 48C illustrate a method where a sheath may be advanced intravascularly through the inferior vena cava and into the right atrium where an imaging hood is engaged to the septal wall and purged with the clear fluid to provide direct visualization.
Figure 48B:
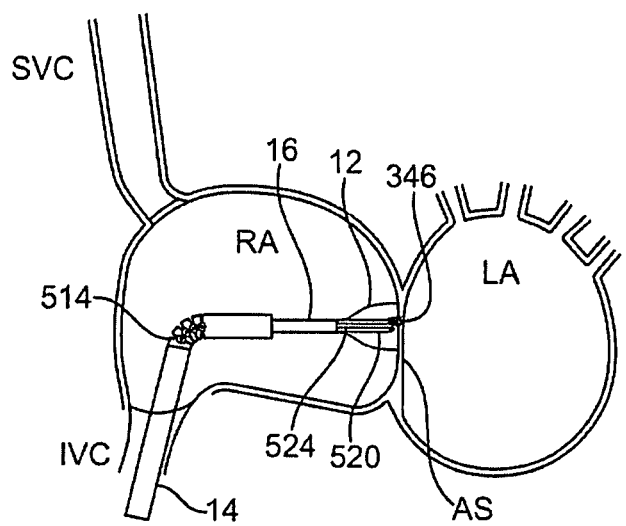

The tissue-imaging catheter provides a clear direct visualization within the heart allowing instruments within the imaging hood to perform various procedures, such as a trans-septal procedure for locating and crossing a device from the right atrium RA to the left atrium LA via the atrial septum AS. FIG. 48A illustrates a method where sheath 14 may be advanced intravascularly through the inferior vena cava IVC and into the right atrium RA. The sheath 14 distal portion may be articulated via steerable portion 514 to direct the distal end towards the atrial septum AS. Deployment catheter 16 and imaging hood 12 may then be deployed from sheath 14 and advanced towards the wall of the atrial septum AS where it may be positioned, e.g., to locate the fossa ovalis along the septal wall. The catheter 16 could be repositioned if necessary to determine the best location to cross the fossa ovalis using a trans-septal puncture described below. Once positioned, tissue engager 346 may be utilized to temporarily engage or grab onto the underlying tissue to provide for a relatively secure positioning between hood 12 and the tissue, as shown in FIG. 48B.

The catheter assembly may contain a number of articulation and manipulation controls. For example, one or more push-pull wires may be used for steering the distal end portion of the device in various directions to desirably position the imaging hood 12 adjacent to a region of tissue to be visualized. The push-pull wire or wires may be articulated via their proximal ends from outside the patient body. Alternatively, the deployment catheter may be articulated by computer control, as described above.

Figure 48C:
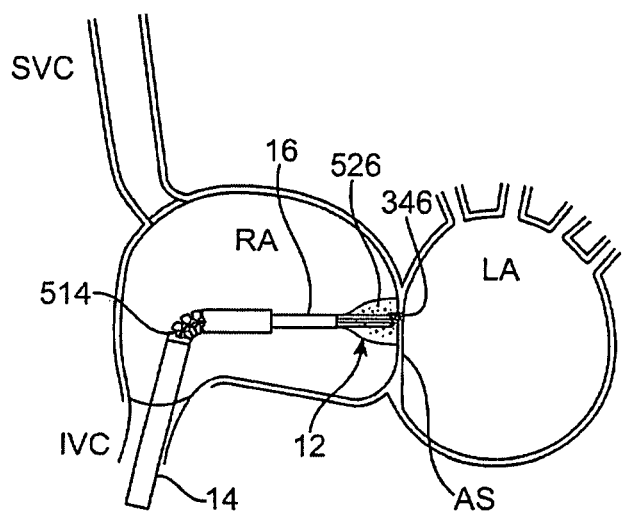

To obtain a visible image, the imaging hood 12 may be purged with the displacing fluid 526 pumped at a positive pressure through a fluid delivery lumen until the fluid fills the open area or field 26 within hood 12 partially or completely and displaces the blood within hood 12, as shown in FIG. 48C. The displacing fluid 526 flow may be laminarized to improve its clearing effect and to help prevent blood from re-entering the imaging hood 12. The flow rate can be monitored and adjusted to ensure image quality.

Moreover, the flow rate may be adjusted manually by the physician or via an active feedback mechanism to automatically adjust the flow rate.

Figure 49A:
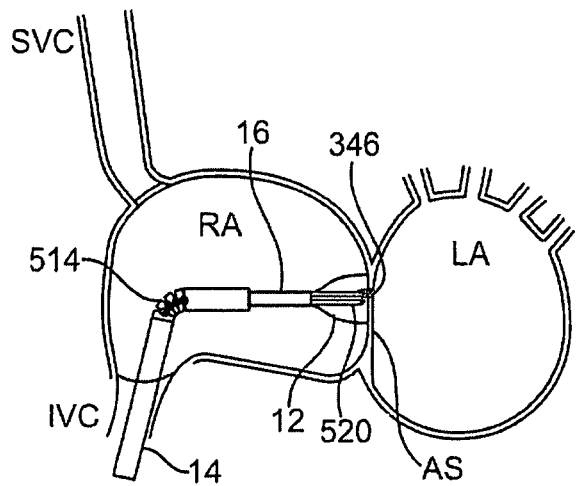
FIGS. 49A to 49C illustrate another method where a guidewire may be passed through the atrial septum by a piercing instrument.
Figure 49B:
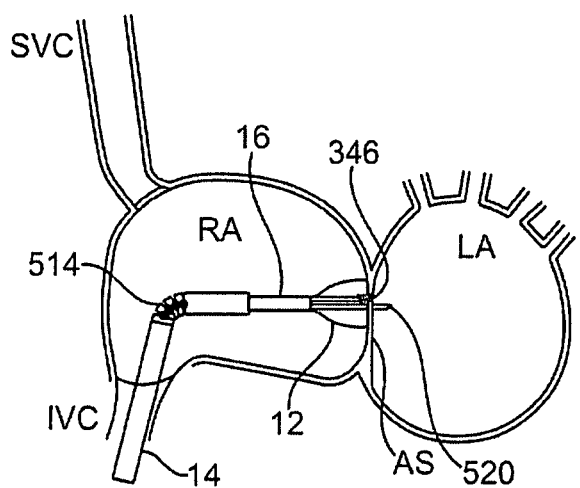
Figure 49C:
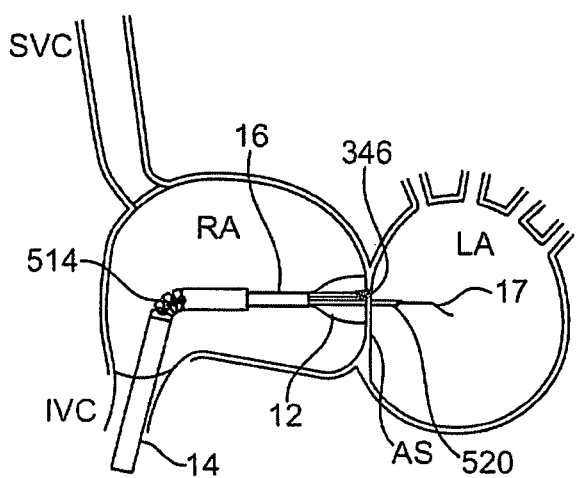

Once the imaging hood 12 has been cleared and direct visual confirmation of the underlying tissue has been obtained by the physician, piercing needle 520 may be advanced within hood 12 while under direct visualization, as shown in FIG. 49A, until needle 520 has punctured into and through atrial septum AS, as shown in FIG. 49B. Once the needle 520 is at least partially within the left atrium LA, a guidewire 17 may be passed through the needle lumen and into the left atrium LA, as shown in FIG. 49C. Once the guidewire 17 has been passed trans-septally, direct visual confirmation under imaging hood 12 may be further attained of the guidewire 17 position. The needle 520 and catheter 16 may be withdrawn to leave behind guidewire 17 positioned trans-septally within left atrium LA to facilitate access for other instruments passed intravascularly from the right atrium RA into the left atrium LA over or along guidewire 17.

Figure 50A:
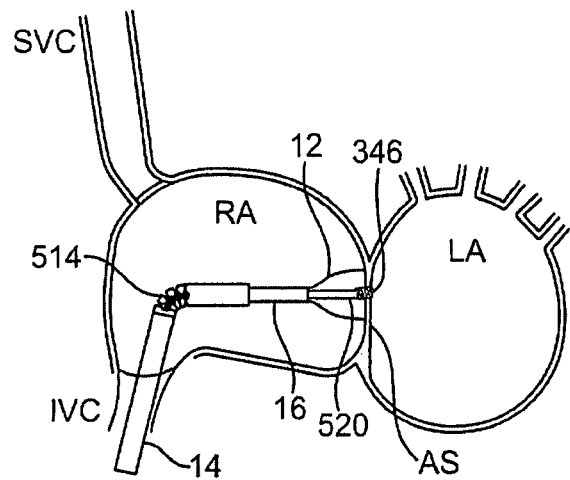
FIGS. 50A to 50C illustrate another method where an engaging element may be placed directly upon the needle such that a guidewire may be concentrically delivered within the penetrating device across the atrial septum.
Figure 50B:
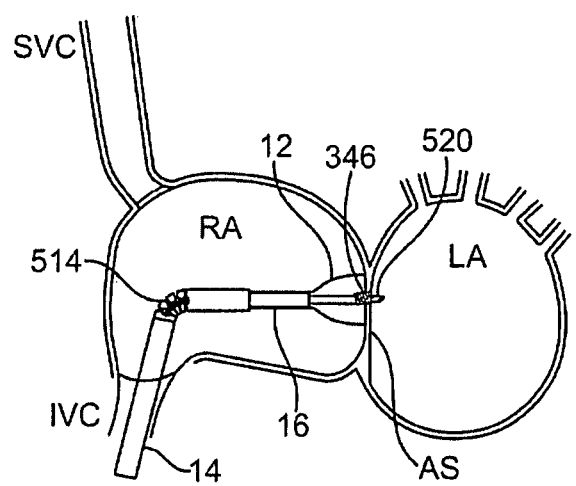
Figure 50C:
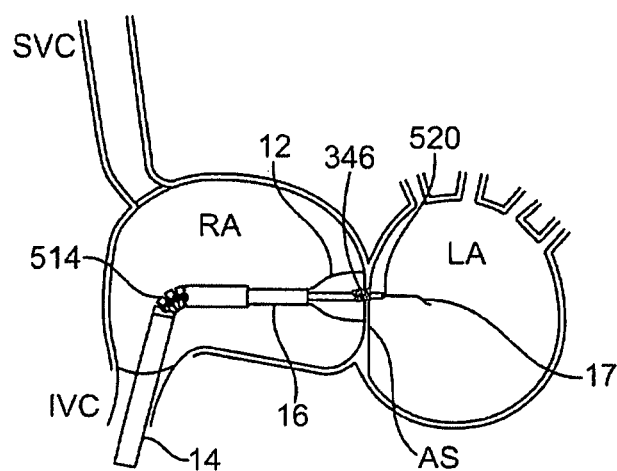

In another variation for crossing the atrial septum AS, FIG. 50A illustrates use of an engaging element 346 placed directly upon the needle 520 as shown in FIG. 47A where guidewire 17 may be concentrically delivered within the penetrating device across the atrial septum 520. Once imaging hood 12 and catheter 16 has been desirably positioned with respect to atrial septum AS, needle 520 may be pierced into the tissue and engaged via element 346. The needle 520 may be further advanced with the tissue engaged until the distal tip is passed into the left atrium LA, as shown in FIG. 50B. Alternatively, a penetrating device such as a cannula may be used to puncture and cross the tissue layer into the left atrium LA of the heart. Guidewire 17 may then be delivered concentrically through the needle 520, as shown in FIG. 50C, and across the atrial septum AS. With the guidewire 17 in place, additional devices (not shown) may be delivered into the left atrium LA along or over guidewire 17. Moreover, dilating devices may be placed over guidewire 17 to provide access of additional various therapeutic devices into the left atrium LA.

Figure 51:
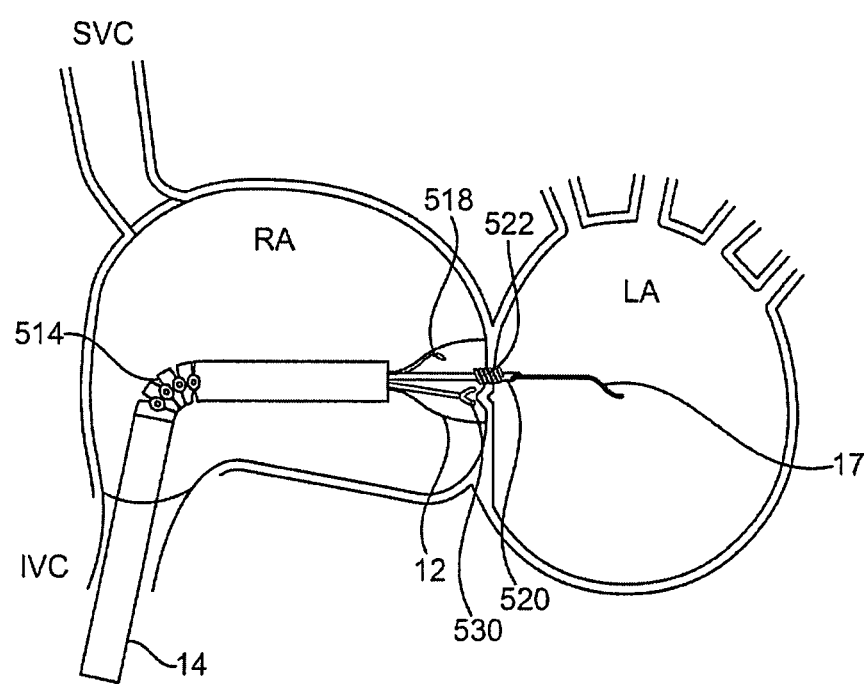
FIG. 51 shows another variation utilizing a tissue grasper to engage the tissue allowing the penetrating needle to cross the atrial septum by pulling proximally on the tissue with the tissue graspers and distally pushing the needle across the tissue layer.

FIG. 51 shows another variation utilizing a tissue grasper 530 to engage the tissue allowing the penetrating needle 520 to cross the atrial septum AS by pulling proximally on the tissue with the tissue graspers 530 and distally pushing the needle 520 across the tissue layer. The guidewire 17 may be concentrically positioned within the needle 520 and subsequently advanced into the left atrium LA. By pulling proximally on the tissue towards the interior of hood 12, tenting of the tissue into the left atrium LA may be avoided when pushing distally with needle 520 upon the tissue wall. Moreover, by pulling proximally on the tissue, accidental puncturing of surrounding anatomical structures may be potentially avoided when passing needle 520 through the tissue by preventing or inhibiting tissue tenting, as described below in further detail.

Figure 52A:
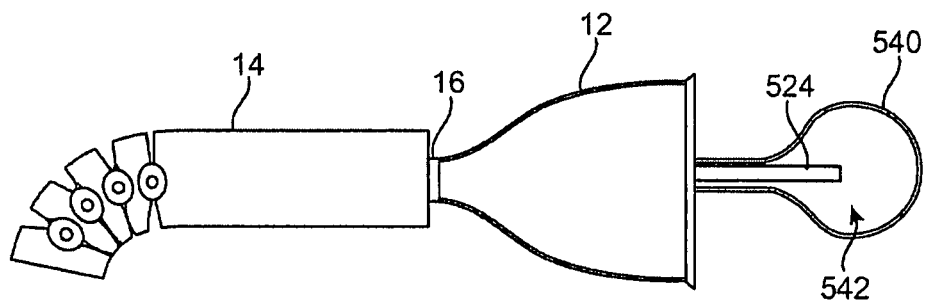
FIGS. 52A and 52B show side views of imaging assemblies utilizing an imaging balloon inflatable within or distal to the imaging hood and having the imaging element either contained within the balloon or adjacent thereto, respectively.
Figure 52B:
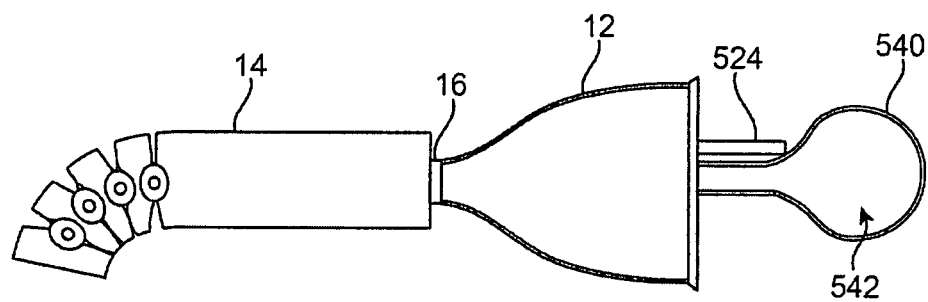

Yet another variation for the tissue visualization assembly is illustrated in the side views of FIGS. 52A and 52B. This variation utilizes a translucent imaging balloon 540 which may be optionally included in combination with the imaging hood 12 for inflation and placement against the tissue surface to provide the physician an initial determination of a position of the catheter distal end prior to expansion of the visualization imaging hood 12 and/or prior to deployment of the imaging hood 12 against the tissue wall. The balloon 540 may be inflated with any of the translucent gases or fluids described above and the imager 524 may be optionally positioned within the balloon interior 542, as shown in FIG. 52A, or outside and proximal to the balloon 540, as shown in FIG. 52B. Additionally, a contrast agent may be utilized to fill the balloon to provide for further visualization by an extra-corporeal visual modality, e.g., fluoroscopy, ultrasound, etc.

Figure 53:
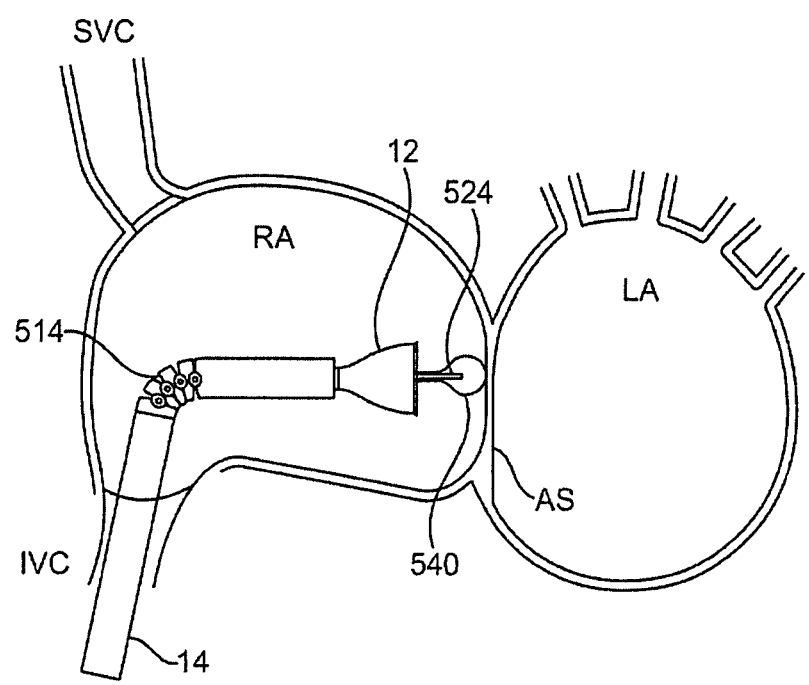
FIG. 53 shows an imaging hood having an inflatable balloon expanded and placed against the tissue wall for obtaining an initial determination of catheter placement relative to the septal wall.

As shown in FIG. 53, imaging hood 12 may be expanded and balloon 540 may be inflated and positioned within the hood 12 or distal thereof. In either case, with balloon 540 inflated and imager 524 (such as an optical fiber bundle, CCD or CMOS camera, etc.) positioned within, the underlying tissue surface may be visualized by pressing balloon 540 against the tissue surface prior to hood expansion and/or deployment to provide an initial image and visual assessment of catheter location relative to the atrial septum AS.

If the initial visual assessment indicates that the catheter should be moved to another location for trans-septal puncture, the catheter position may be adjusted and moved while visualizing against the tissue wall or the catheter may be removed from the tissue wall and repositioned for another visual assessment. Alternatively, balloon 540 may be deflated and the catheter repositioned to another location along the tissue wall, where balloon 540 may again be re-inflated for visualization. Once the catheter position has been visually confirmed as being positioned at a desirable location for puncture, the balloon 540 may be deflated and optionally withdrawn from imaging hood 12 and the purging fluid may be pumped into hood 12 to provide the open space for visualization and treatment by additional tools, as described above.

Figure 54A:
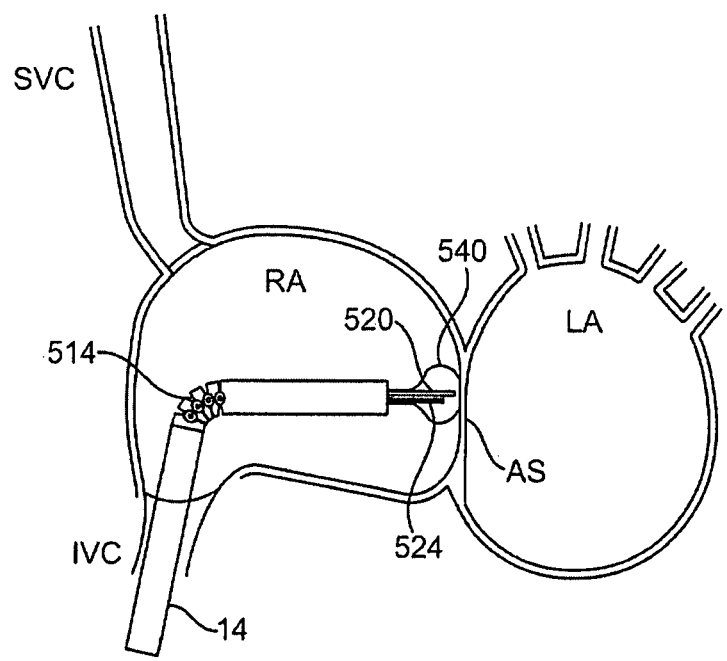
FIGS. 54A and 54B show an example of utilizing the inflatable balloon without the use of the imaging hood for obtaining transseptal access.
Figure 54B:
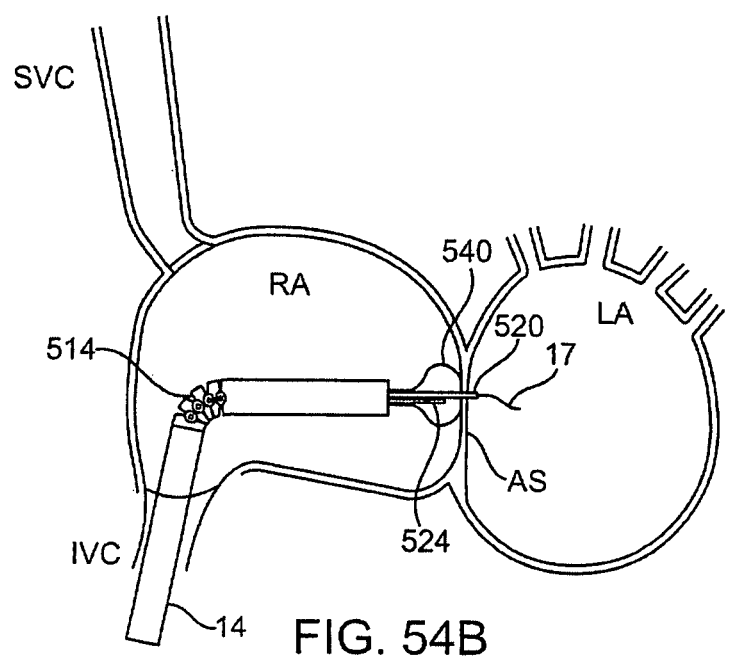

Alternatively, as shown in FIGS. 54A and 54B, imaging hood 12 may be omitted entirely and balloon 540 having a working channel could be positioned against the tissue wall directly, e.g., at the fossa ovalis. Imaging element 524 can be used to provide an image of the tissue as the balloon 540 is positioned against the wall of the heart, as shown in FIG. 54A. The balloon 540 itself is used to displace the blood and provide a clear image of the tissue when positioned against the wall where a tissue engager and/or needle 520 may be passed directly through the balloon interior and pierced through the balloon membrane to cross the atrial septum AS, as shown in FIG. 54B. The needle 520 can have a guidewire 17 passed therethrough to allow for entry into the left atrium LA.

Figure 55A:
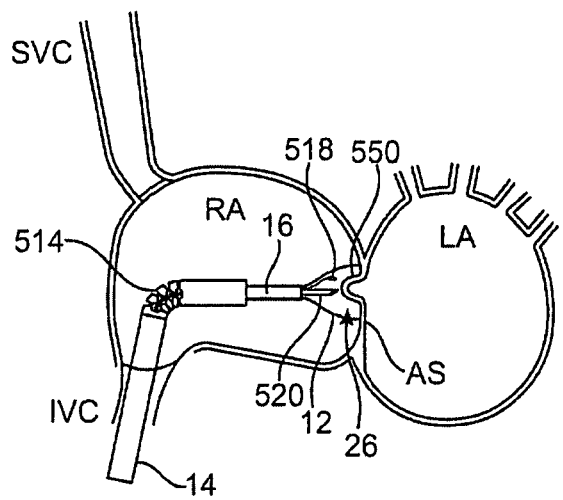
FIGS. 55A to 55C illustrate another method for transseptal access with an imaging hood utilizing a vacuum created within the hood for engaging the septal wall.
Figure 55B:
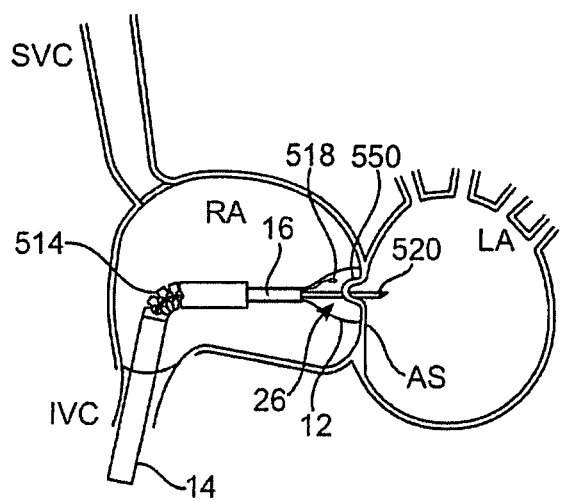
Figure 55C:
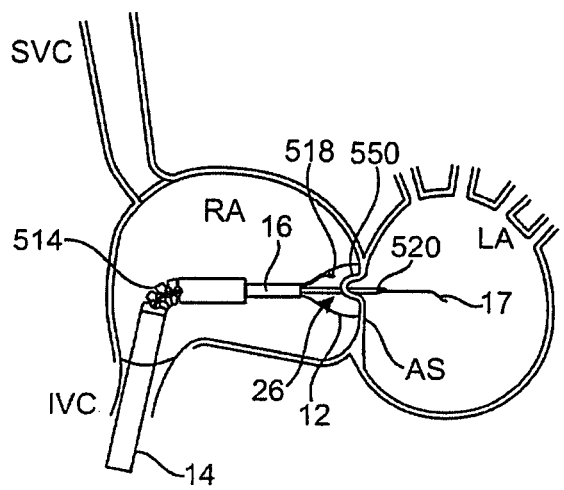

In yet another variation, as shown in FIGS. 55A to 55C, the tissue of the atrial septum AS can be engaged using a vacuum created within imaging hood 12. Initially, the imaging hood 12 may be deployed and the location for crossing the atrial septum AS determined using the imaging element and flushing port as described above. Once the location has been determined, the tissue may be engaged using a suction port within the multi-lumen catheter 16 and the imaging hood 12 may function as a vacuum chamber to draw in the approximated tissue 550 and hold it securely within hood 12, as shown in FIG. 55A. While the tissue 550 is engaged using the vacuum, needle 520 can be passed through the atrial septum AS and into the left atrium LA, as shown in FIG. 55B. As described above, needle 520 may pass guidewire 17 therethrough across the atrial septum AS, as shown in FIG. 55C. As described above, by pulling proximally on the tissue, accidental puncturing of surrounding anatomical structures may be potentially avoided when passing needle 520 through the tissue by preventing or inhibiting tissue tenting.

Figure 56A:
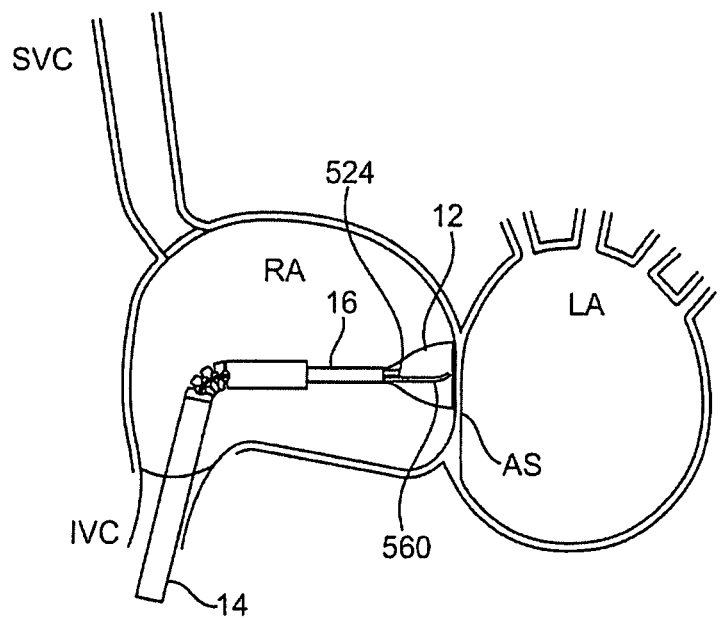
FIGS. 56A and 56B illustrate another method for transseptal access where an energizable probe is used to pass through the tissue.
Figure 56B:
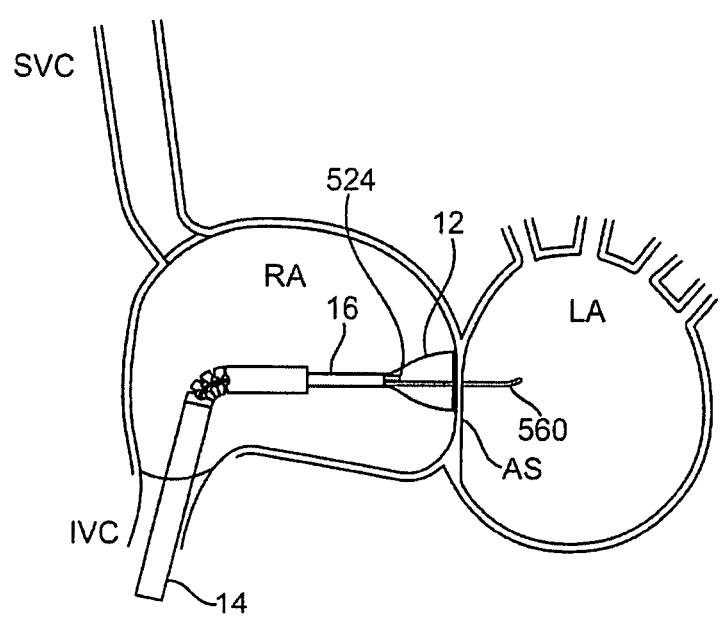

In yet another variation, the tissue can be engaged using a cryo-probe configured to reduce its temperature to below 0° C. to temporarily adhere to the underlying tissue. Once the probe temperature has been reduced, it may be adhered to the tissue to engage it and once the procedure has been completed, the probe may be allowed to warm or heated to thus release the adhered tissue. Another variation utilizing an energizable probe 560 using an energy modality (e.g., a radio-frequency, laser, microwave, high intensity ultrasound, etc.) may be used to pierce or pass through the septal wall, as shown in FIGS. 56A and 56B. Because the energizable probe 560 utilizes energy to pass through the tissue rather than a mechanical piercing force, the probe 560 may be advanced within the hood 12 and passed through the atrial septum AS, while under direct visualization within the hood 12, potentially without the use of an engaging element, as shown in FIG. 56B. As above, a guidewire may be positioned through the transseptal opening created using the probe 560.

Figure 57A:
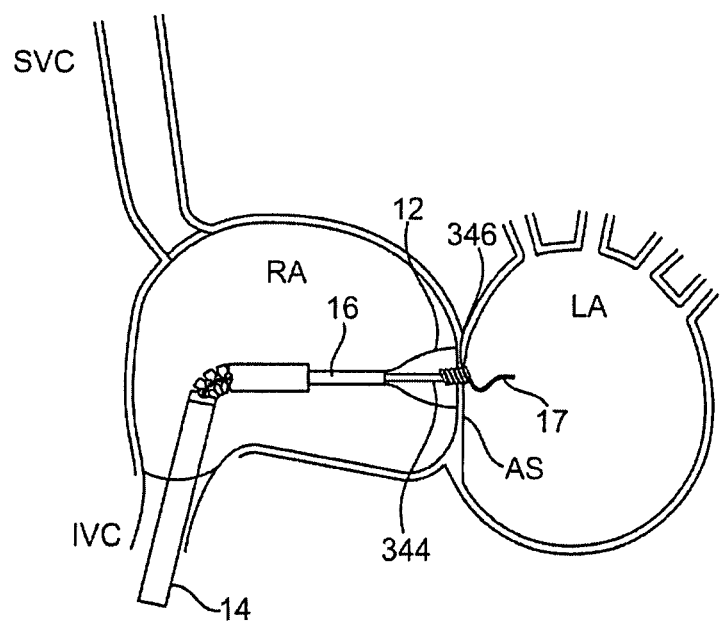
FIGS. 57A and 57B show yet another variation where a penetrating helical tissue engager may be advanced through the tissue wall and a guidewire may be advanced through a lumen defined within the tissue engager.
Figure 57B:
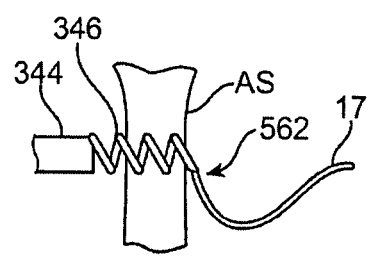

FIG. 57A shows yet another variation where a penetrating helical tissue engager 346 may be advanced through the atrial septal AS such that a distal end of the engager 346 is positioned within the left atrium LA. A guidewire 17 may then be advanced through guidewire lumen 562 defined through the helical member, as shown in FIG. 57B, until guidewire 17 is advanced into the left atrium LA. Once the guidewire 17 has been advanced sufficiently into the left atrium LA, the engager 346 may be withdrawn from the septal wall and/or the catheter 16 may be removed leaving the guidewire 17 in place through the atrial septum AS.

Figure 58:
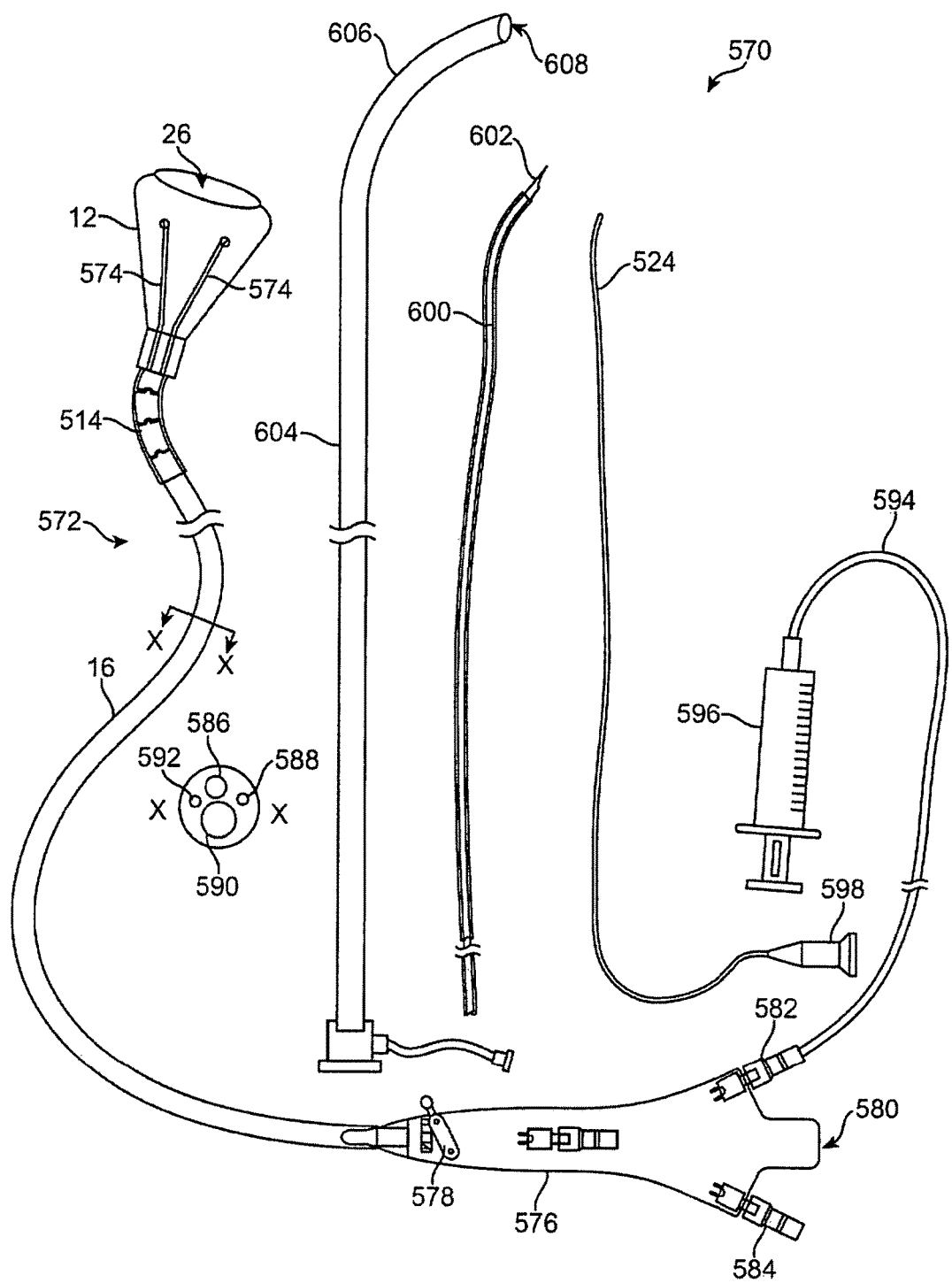
FIG. 58 shows an introduction assembly which may be utilized for achieving transseptal access.

In yet other variations for accomplishing intravascular trans-septal access, the imaging assembly may be utilized with various introduction sheaths to facilitate the articulation and positioning of the imaging hood 12 with respect to the septal wall. One example of an introduction assembly 570 is illustrated in FIG. 58 including imaging assembly 572. The imaging assembly 572, as described above, may generally comprise the imaging hood 12, shown in this variation as having multiple support struts 574 extending along the hood 12 to provide structural support to the hood 12 when expanded. The deployment catheter 16 may be seen extending from hood 12 to handle 576 where one or more articulation controls 578 may be coupled for providing the manipulation and articulation of hood 12 via articulatable/steerable section 514.

Handle 576 may be manipulated by the physician from outside the patient body and may also include one or more entry ports for providing intravascular access from outside the patient body, through the catheter shaft 16, and into the body. Entry port 580 on handle 576 may be utilized for the insertion of an imager such as imaging assembly 524, which has imager connector 598 at its proximal end for connection to a video input. Fluid port 582 on handle 576 may provide entry for fluid channel 594 connected to fluid reservoir 596, e.g., a syringe, pressured fluid bag, motorized pump, etc., which is used to introduce the purging fluid within imaging hood 12. Entry port 584 on handle 576 can be utilized for the insertion of a piercing instrument, such as piercing instrument 600 having a piercing tip 602, e.g., needle body, beveled sheath tip, etc. for creating a trans-septal passage through the tissue wall.

The cross-sectional view of catheter 16 may also be seen illustrating one variation for the relative placement and positioning of lumens with respect to one another. As seen, imaging assembly lumen 586 for the passage of imager 524 and fluid lumen 588 and piercing instrument lumen 590 for instrument 600 may be adjacent to one another. Moreover, pullwire lumen 592 may also be shown for the routing of one or more push-pull wires therethrough which may be articulated via control 578 for effecting movement of imaging hood 12.

Also shown in the figure is introducer sheath 604 which defines an introducer sheath lumen 608 therethrough for the passage of imaging hood 12 and deployment catheter 16 therethrough within the body. Sheath 604 may optionally define a curved or pre-bent section 606 relative to a longitudinal axis of sheath 604 configured in one of several shapes to facilitate the movement of imaging hood 12 within the body, as described in further detail below. The curved or pre-bent section 606 may be angled relative to the sheath 604 anywhere in a range from 0° to 45° or more depending upon the desired angle of approach to the septal wall.

Figure 59A:
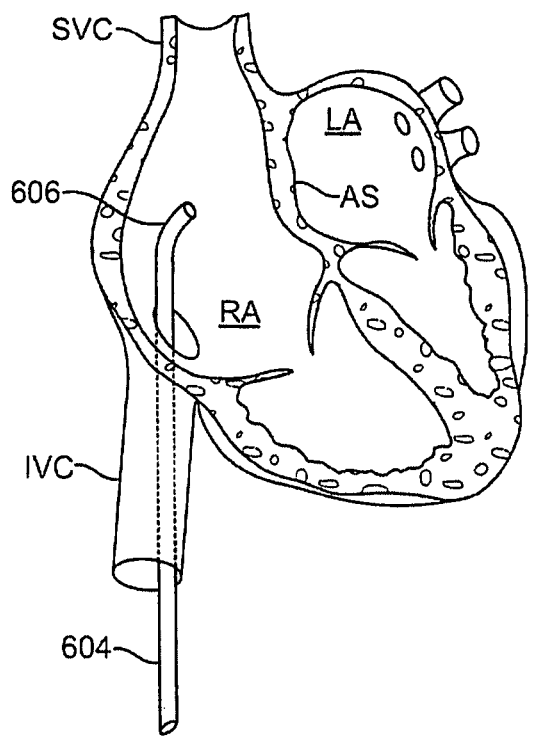
FIGS. 59A to 59E illustrate one method for intravascularly accessing and positioning an imaging assembly utilizing a curved or pre-bent sheath which is angled towards the atrial septum.
Figure 59B:
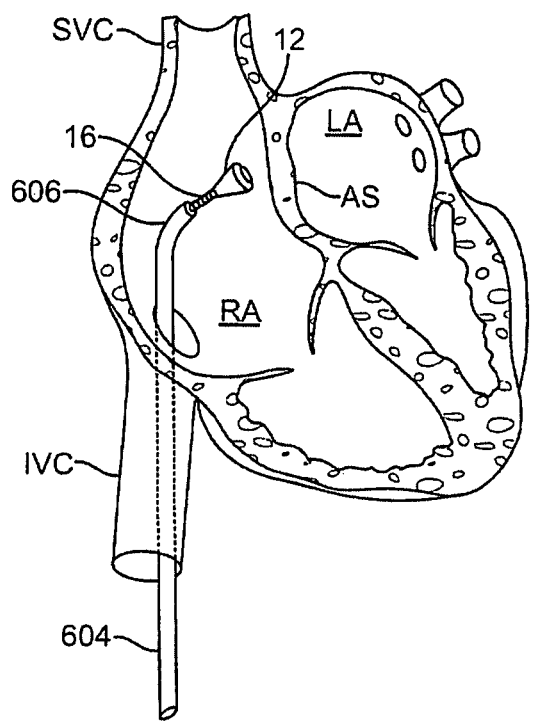
Figure 59C:
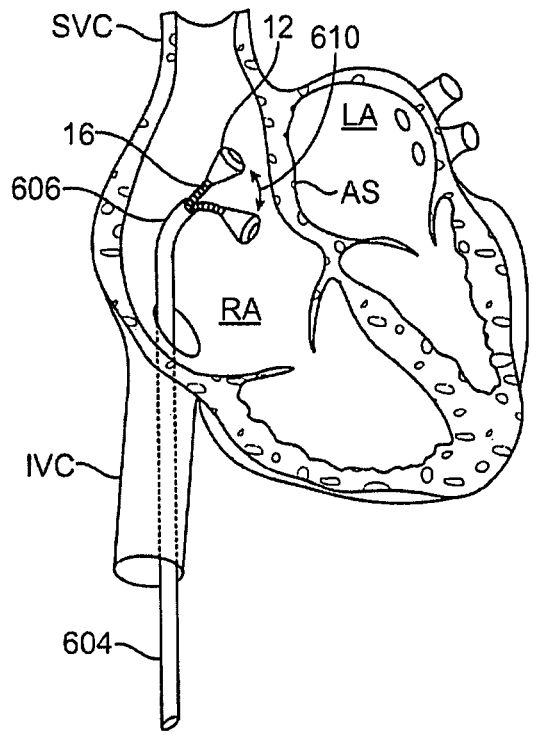
Figure 59D:
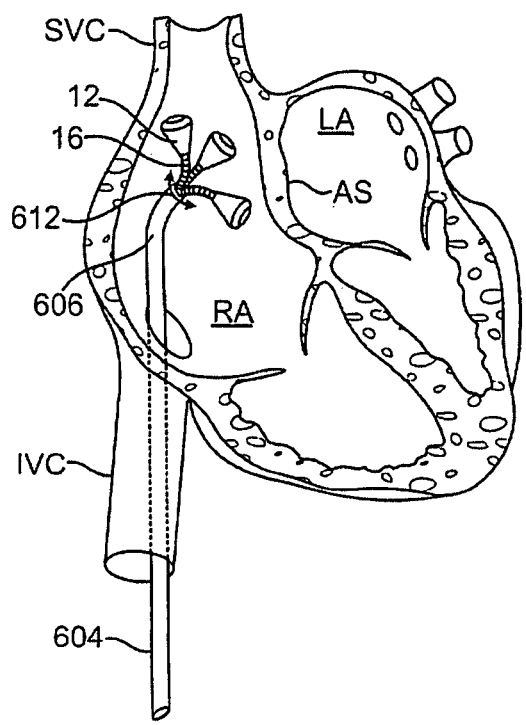
Figure 59E:
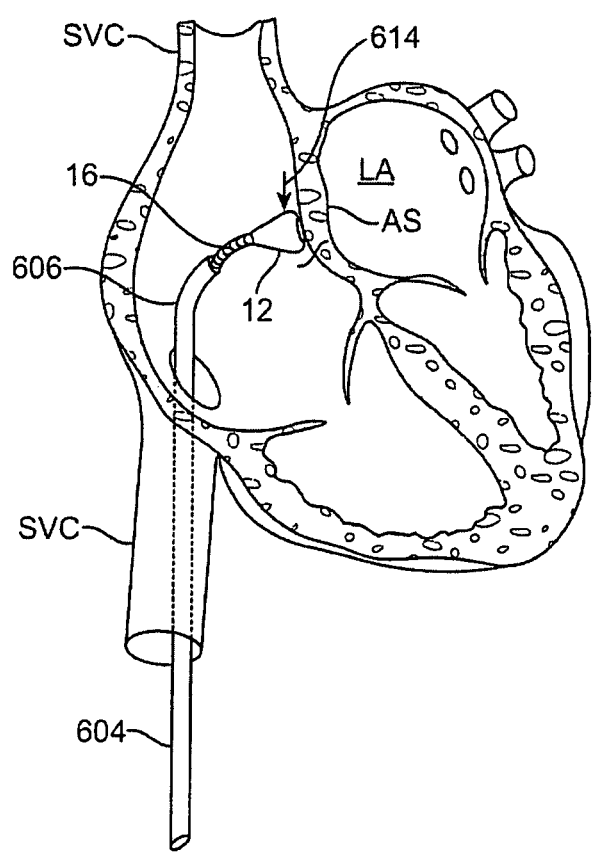

In utilizing an introducer sheath 604 having the curved or pre-bent section 606, FIG. 59A shows how the curved section 606 of sheath 604 may be introduced, in this example, through the IVC and into the right atrium RA of the patient. As curved section 606 takes its curved configuration, the distal end of sheath 604 may be rotated to angle it towards the atrial septum AS to ensure a direct path for imaging hood 12 to the tissue wall, as shown in FIG. 59A. Deployment catheter 16 and imaging hood 12 may then be advanced out of sheath 604 and into the right atrium RA where hood 12 may be expanded, as shown in FIG. 59B. As imaging hood 12 is pre-bent via section 606 towards the atrial septum AS, catheter 16 may be articulated via control 578 on handle 576, as indicated by the direction of planar articulation 610 in FIG. 59C, and/or rotated by its proximal end to torque the imaging hood 12 as indicated by the direction of rotational articulation 612 in FIG. 59D, to desirably position the imaging hood 12 relative to the atrial septum AS. Once imaging hood 12 has been contacted against the tissue wall and the blood purged from the viewing field, direct visual confirmation of the hood 12 position along the tissue wall may be accomplished. While viewing the underlying tissue, imaging hood 12 may be moved along the atrial septum to locate anatomical landmarks such as the fossa ovalis and/or the ostium of the coronary sinus to provide visual confirmation as to the positioning of the hood 12 prior to trans-septally puncturing across the septum. Transverse articulation 614 of imaging hood 12 along the atrial septum AS is indicated by the direction of movement as shown in FIG. 59E.

Figure 60A:
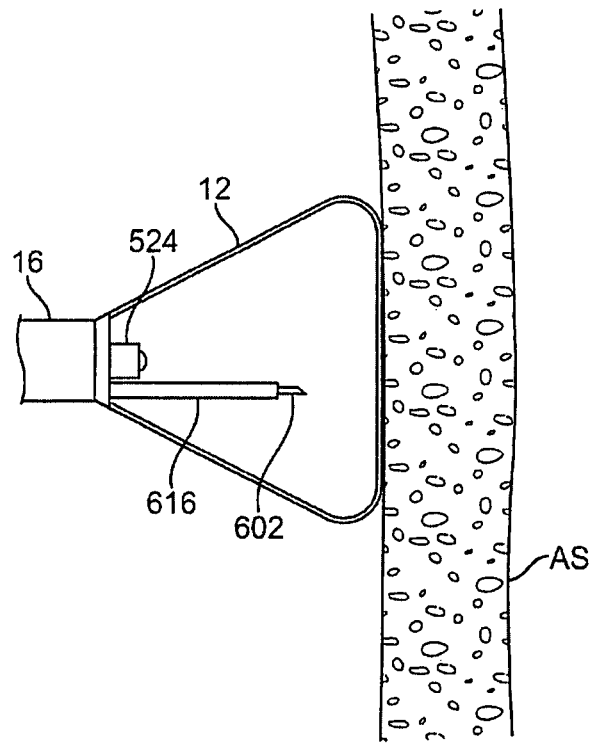
FIGS. 60A to 60G illustrate one method for piercing through the atrial septum and passing a guidewire therethrough while under direct visualization from the imaging hood.
Figure 60B:
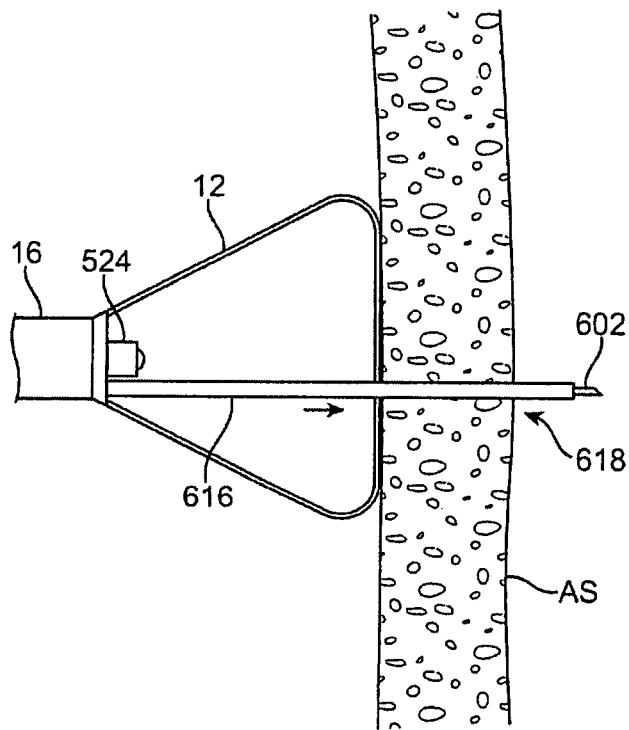

Once the imaging hood 12 has been suitably positioned along the atrial septum and direct visual confirmation of the underlying tissue has been accomplished, the piercing tip 602 of piercing instrument 600 may be advanced through imaging hood 12 while under direct visualization by imager 524 (or an electronic imager positioned along the hood interior wall, as described above), as shown in the partial cross-sectional view of FIG. 60A. Although piercing instrument 600 may be utilized alone, needle sheath 616 may be optionally used to pass the needle instrument 600 through. In either case, both the piercing tip 602 and needle sheath 616, if used, may be punctured through the underlying septal wall to create transseptal puncture 618, as shown in FIG. 60B.

Figure 60C:
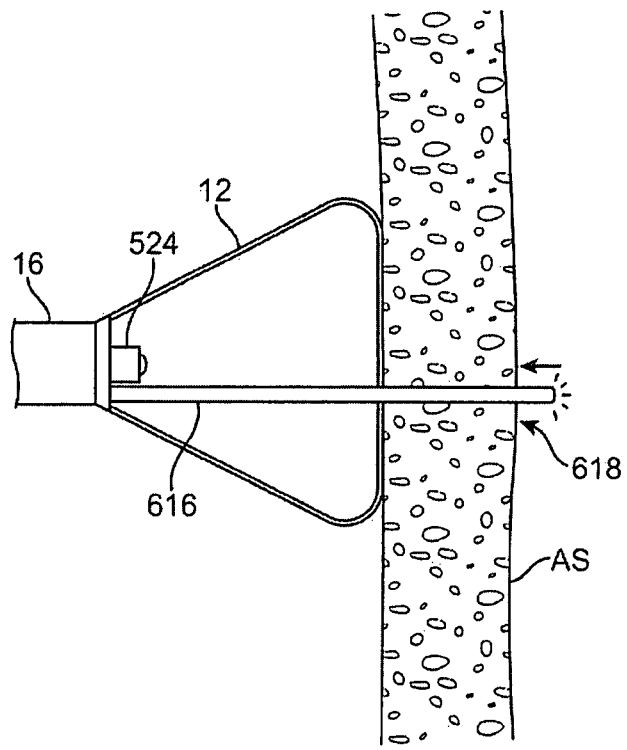
Figure 60D:
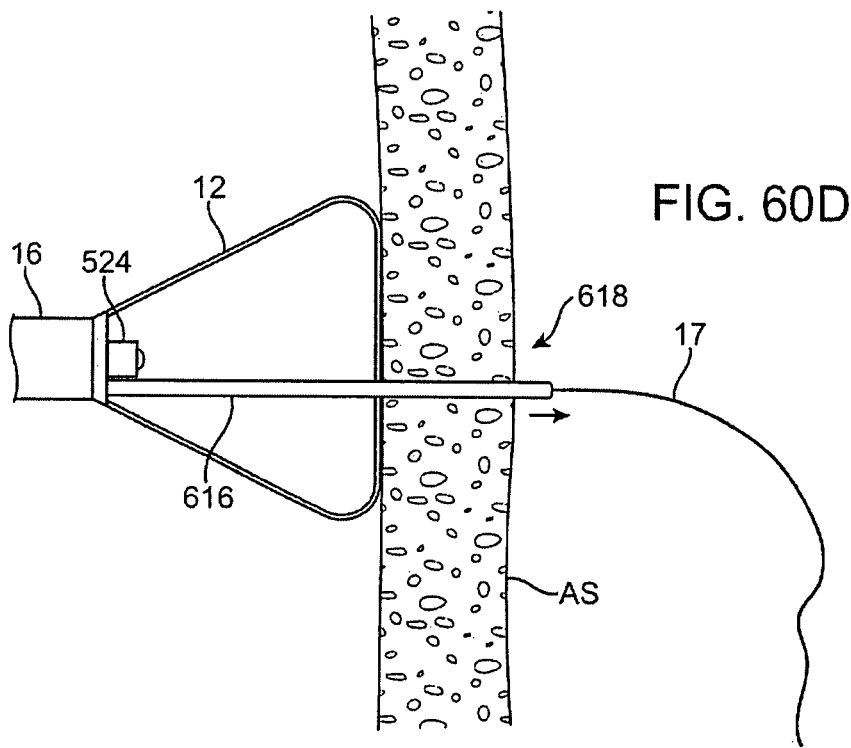
Figure 60E:
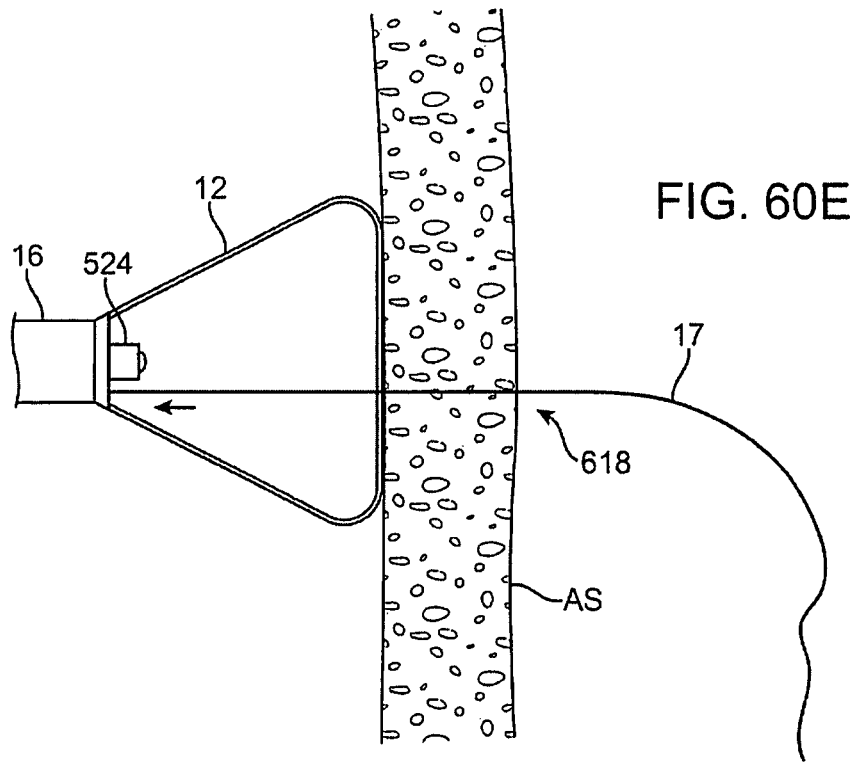
Figure 60F:
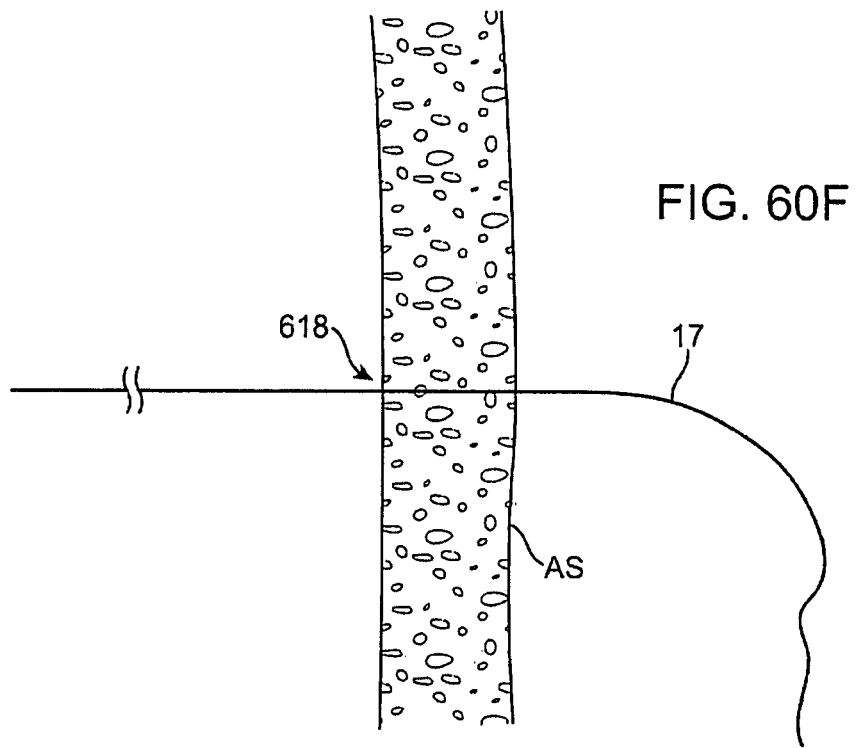
Figure 60G:
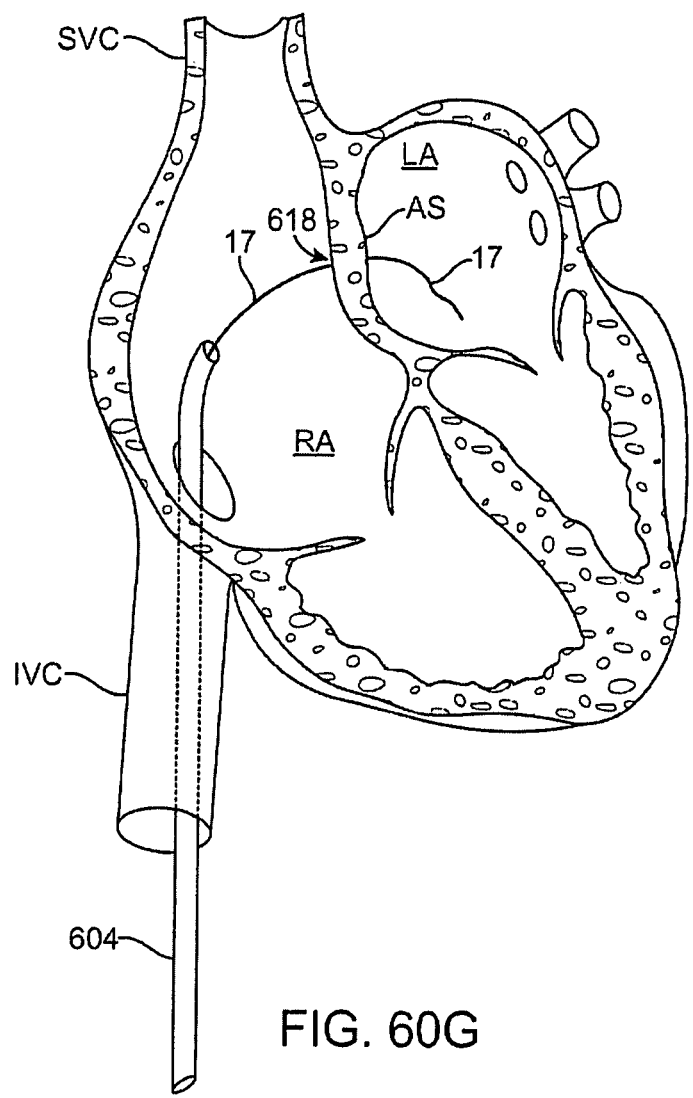

The piercing instrument 600 may be withdrawn from needle sheath 616, which may be left within the transseptal puncture 618 and as shown in FIG. 60C. Guidewire 17 may then be advanced through needle sheath 616 into the left atrium LA and needle sheath 616 may be retracted and withdrawn from puncture 618 leaving guidewire 17, as shown in FIGS. 60D and 60E. The catheter 16 and imaging hood 12 may then be disengaged and removed leaving guidewire 17 crossing puncture 618 for use in advancing additional instruments along or over the guidewire 17 and into the left atrium LA, as shown in FIG. 60F. A portion or the entire transseptal puncture procedure may be accomplished while under direct visualization within imaging hood 12. FIG. 60G illustrates guidewire 17 left crossing the atrial septum AS with imaging hood 12 removed and introducer sheath 604 remaining within the IVC for the introduction of any number of instruments.

Figure 61A:
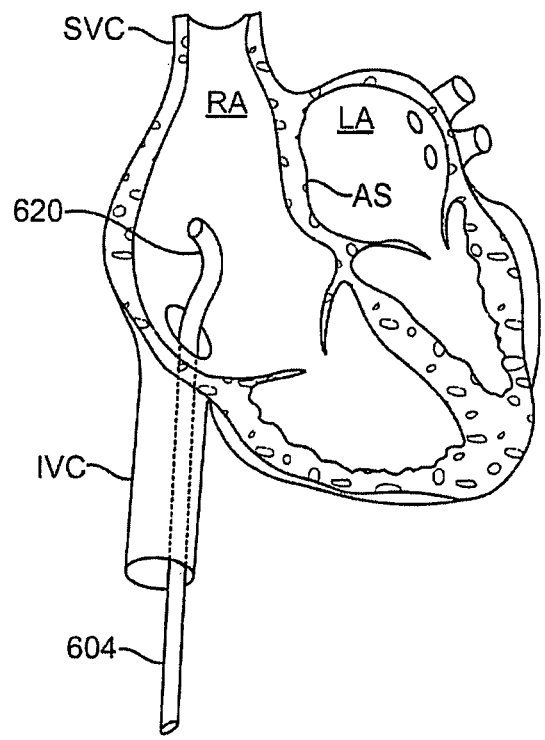
FIGS. 61A to 61C illustrate another method for intravascularly accessing and positioning an imaging assembly utilizing a curved or pre-bent sheath which is angled away from the atrial septum.
Figure 61B:
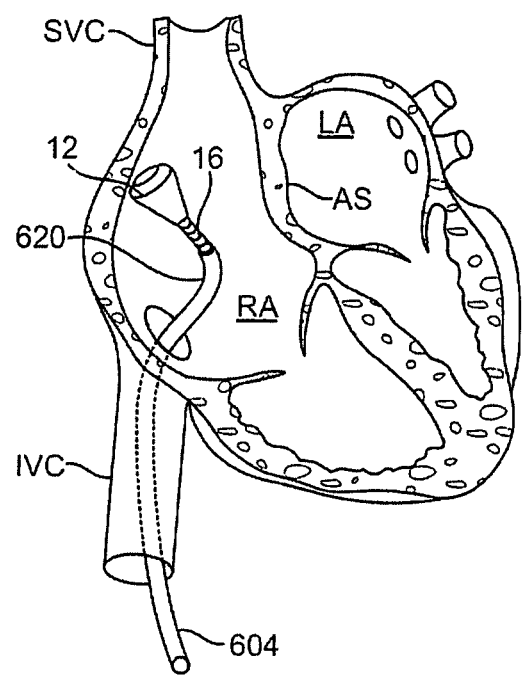
Figure 61C:
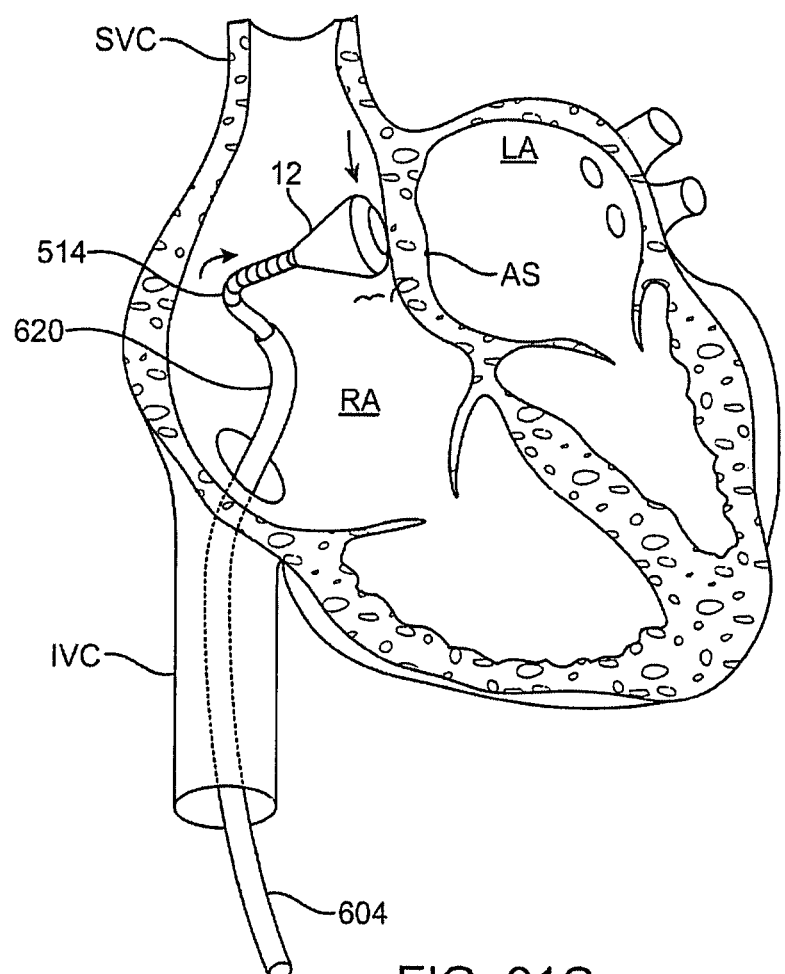

In another method, introducer sheath 604 having an oppositely curved or pre-bent section 620 may be utilized, as shown in FIG. 61A. In such case, a sheath 604 having a curved or pre-bent section like section 606 above may be simply rotated to point away from the atrial septum AS. Alternatively, oppositely curved section 620 having a dual-curved portion may be utilized such that when imaging hood 12 and deployment catheter 16 is advanced out of sheath 604, catheter 16 retains a compound curve such that imaging hood 12 is pointed away from the atrial septum AS, as shown in FIG. 61B. The articulatable portion 514 may then be controlled to curve imaging hood 12 towards the atrial septum AS to provide an approach which is more perpendicular relative to the tissue surface, as shown in FIG. 61C.

Figure 62A:
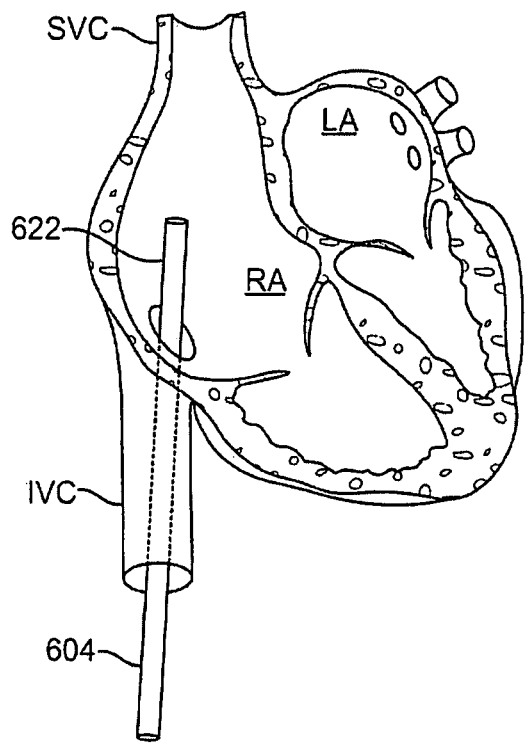
FIGS. 62A to 62C illustrate yet another method for intravascularly accessing and positioning an imaging assembly utilizing a straightened sheath.
Figure 62B:
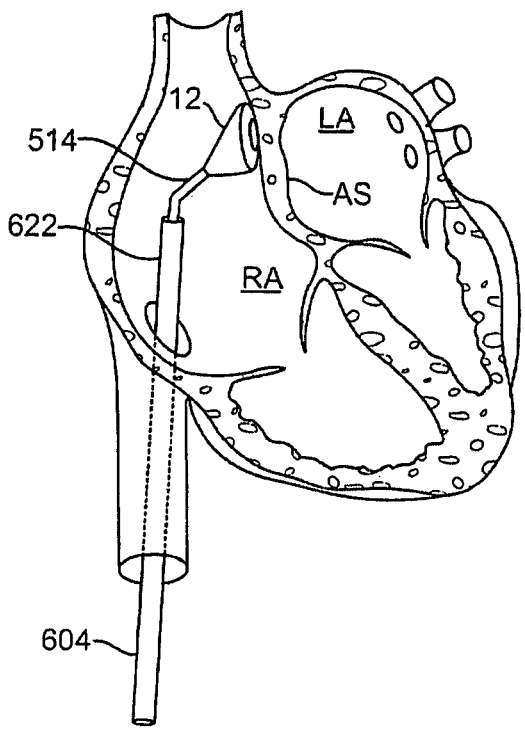
Figure 62C:
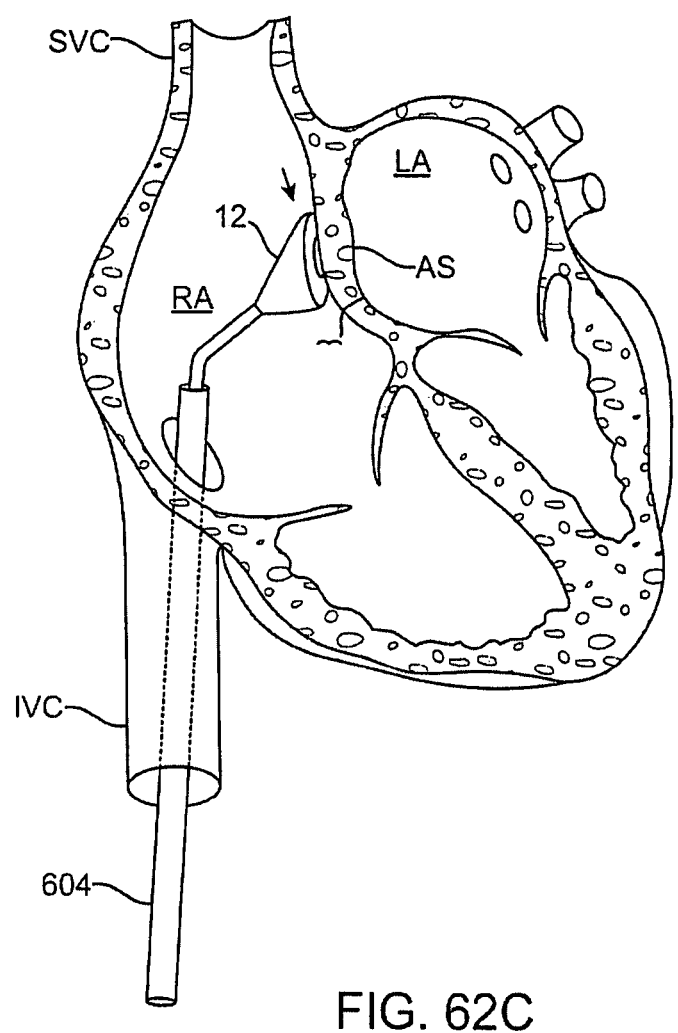

In yet another variation, an introducer sheath 604 having a straightened portion 622 may be utilized, as shown in FIG. 62A, such that imaging hood 12 is articulated via section 514 to approach the atrial septum AS at an angle relative to the tissue surface, as shown in FIG. 62B. Once contact with the tissue wall has been made, imaging hood 12 may be cleared and moved along the atrial septum AS, as shown in FIG. 62C, by translating just the imaging hood 12 or both the hood 12 and sheath 604 until direct visual confirmation of a suitable location has been found for transseptal puncture. As shown in FIGS. 62B and 62C, hood 12 is placed against the tissue surface at an angle relative to the distal end of hood 12 as well as relative to sheath 604. Accordingly, hood 12 may optionally comprise an angled or slanted hood opening or circumference to enable the angled apposition of hood 12 against the tissue surface. Hood 12 may thus be angled or slanted over a various range, e.g., 15° to 60° or greater, relative to a longitudinal axis of hood 12 depending upon the patient anatomy and/or desired angle of approach of hood 12 with respect the tissue surface.

Figure 63A:
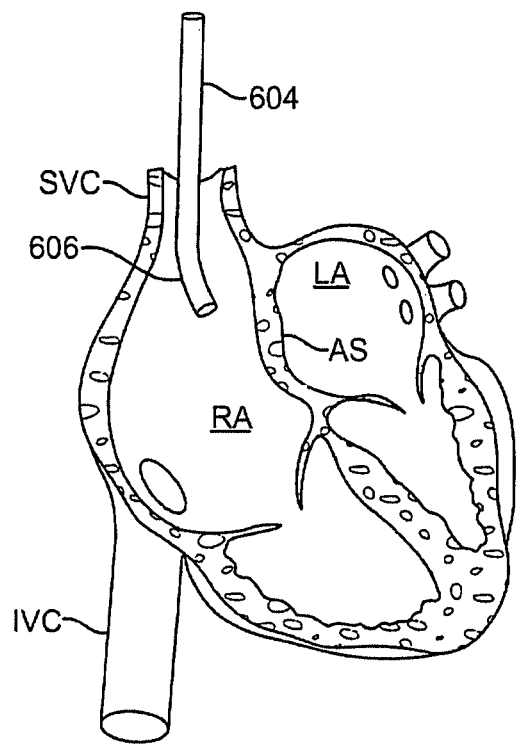
FIGS. 63A to 63C illustrate yet another method for intravascularly accessing and positioning an imaging assembly utilizing an approach through the superior vena cava of the patient.
Figure 63B:
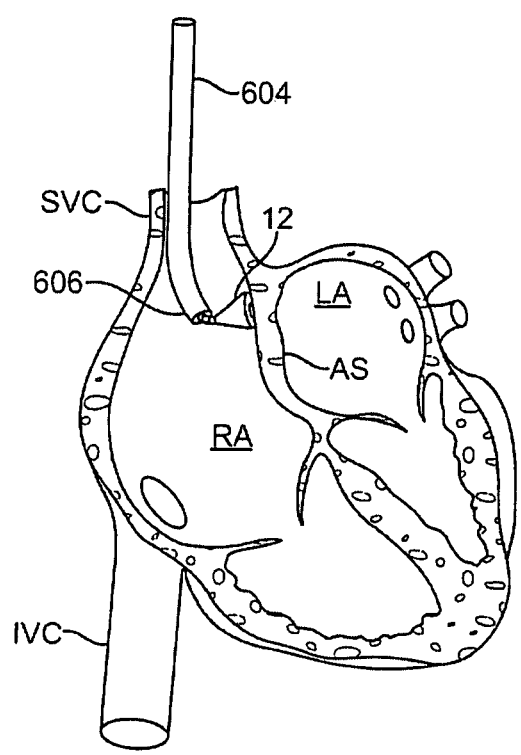
Figure 63C:
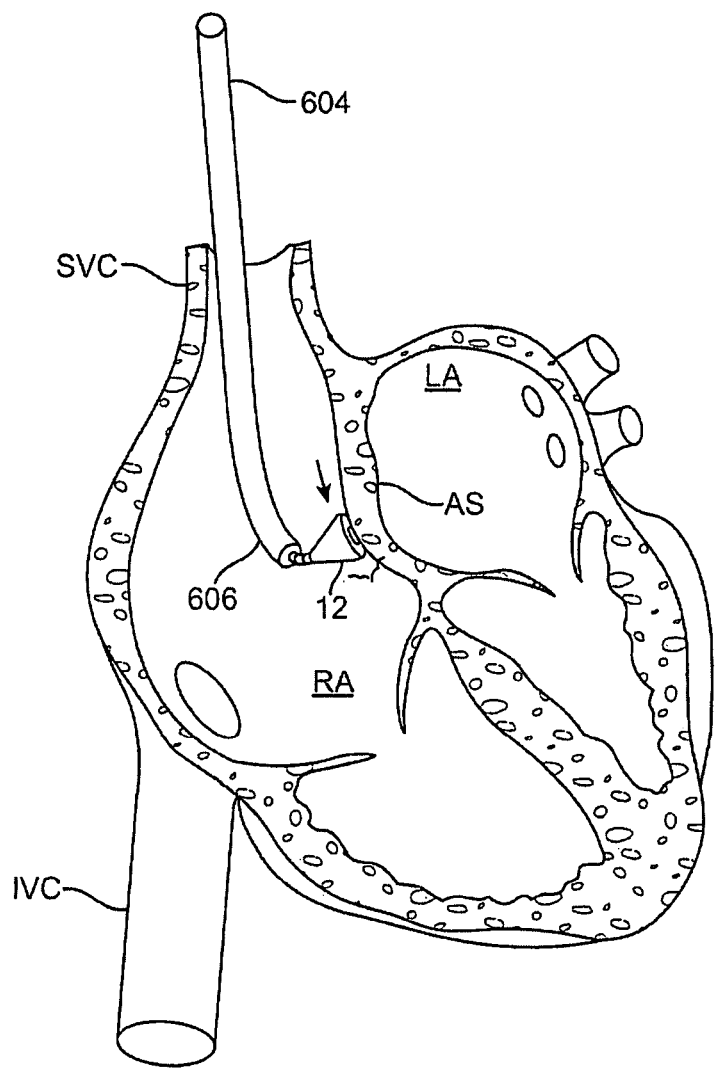

Another variation for approaching the atrial septum AS may include access through the superior vena cava SVC, as shown in FIG. 63A as well as in FIG. 5 above. In this variation, introducer sheath 604 may be advanced intravascularly via the SVC into the right atrium RA. Imaging hood 12 may be introduced into the heart and deployed into contact against a location of the atrial septum AS, as shown in FIG. 63B. Once visual imaging of the tissue has been achieved, sheath 604 and/or imaging hood 12 may be translated along the tissue surface while under direct visualization through the imaging hood 12 until a suitable location for transseptal puncture has been located, as shown in FIG. 63C. A sheath 604 having any of the curved or pre-bent configurations may be utilized as so desired or as suitable.

Whichever intravascular approach is taken, the visualization system is ideally suited for directly visualizing the targeted tissue. Direct in vivo visualization further enables a user to visually identify not only tissue regions generally, but also to distinguish between anatomical landmarks and to visually assess their condition in detail and in color. Such detailed assessment may further allow for a more thorough evaluation and treatment of the underlying tissue also utilizing the system described herein.

Figure 64A:
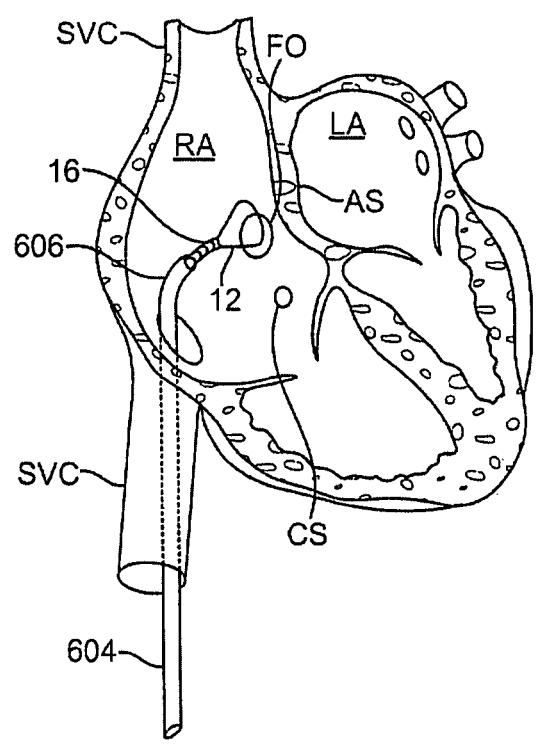
FIGS. 64A and 64B show perspective and partial cross-sectional side views, respectively, of the imaging hood positioned over the fossa ovalis along the septal wall.
Figure 64B:
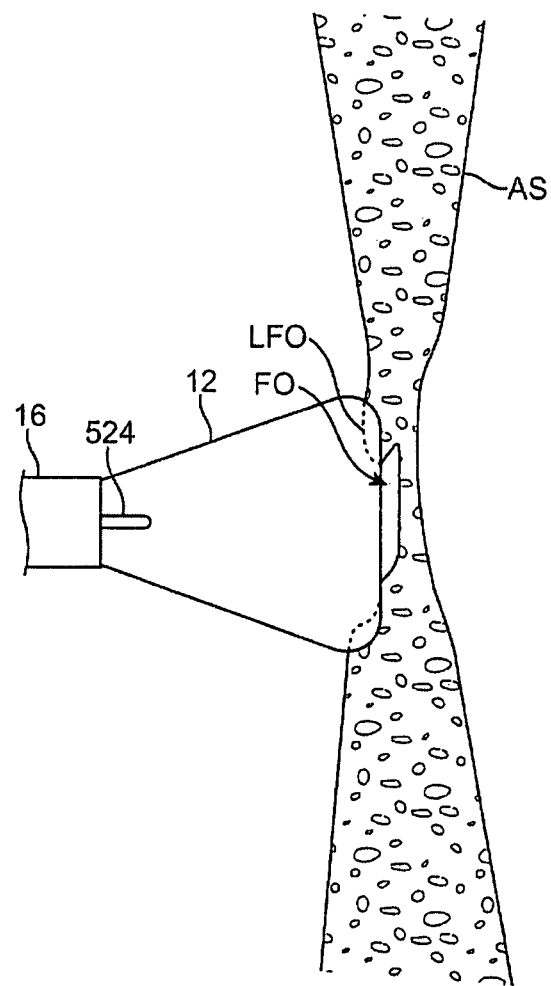
Figure 64C:
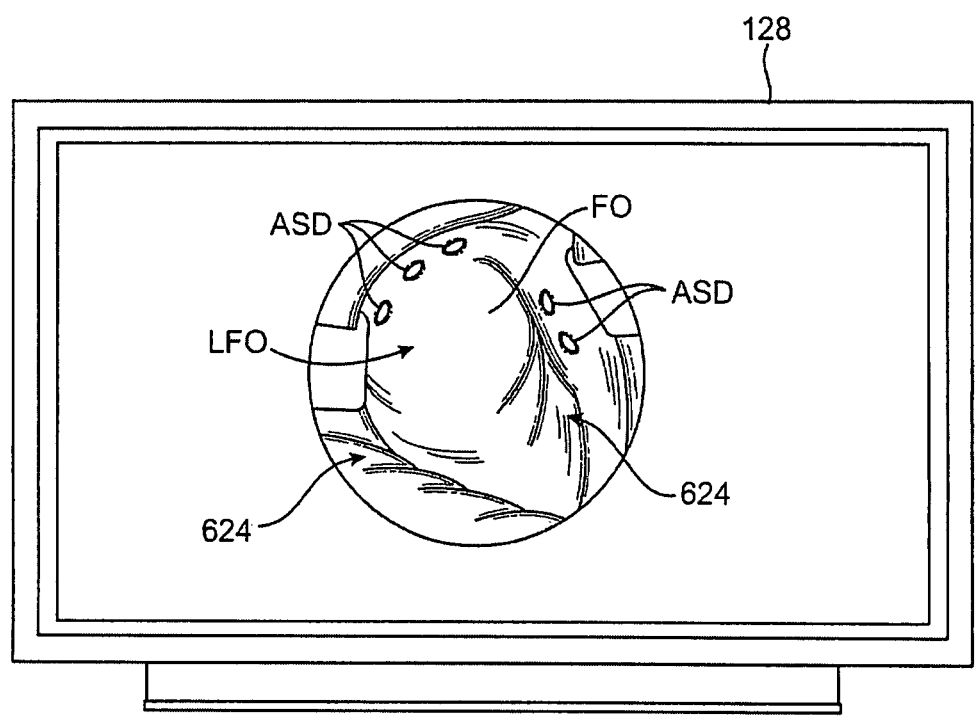
FIG. 64C illustrates various details of anatomical features such as the fossa ovalis and the surrounding tissue which are imaged via the imaging hood.

A further example of visualizing a tissue region is shown in FIG. 64A, which illustrates the deployed imaging hood 12 in apposition to the atrial septal AS wall. While under visualization, imaging hood 12 may be guided along the tissue wall until the fossa ovalis FO is identified. With the imaging hood 12 positioned partially over or directly over or upon the fossa ovalis FO, distinguishing anatomical features of the fossa ovalis FO may be visualized, as shown in the partial cross-sectional side view of FIG. 64B. For instance, features such as the pale white tissue surface of the fossa ovalis FO and the contrasting pink tissue surfaces 624 surrounding the fossa ovalis FO may be directly visualized through imaging hood 12. The images may be captured via any number of imagers described herein, such as imager 524, and displayed upon a monitor 128 for assessment by the user, as shown in FIG. 64C. Additional anatomical features may also be visualized and distinguished, if present, due to the ability of imaging hood 12 to present detailed visual images. For example, anatomical features such as the limbus of the fossa ovalis LFO, located superiorly to the fossa ovalis FO or extending from the fossa ovalis FO, as well as any atrial septal defects ASD which may be present can also be visually distinguished. With the fossa ovalis FO visually distinguished, any number of procedures may be effected upon the tissue, including transseptal puncture and access into the adjacent body lumen.

Figure 65A:
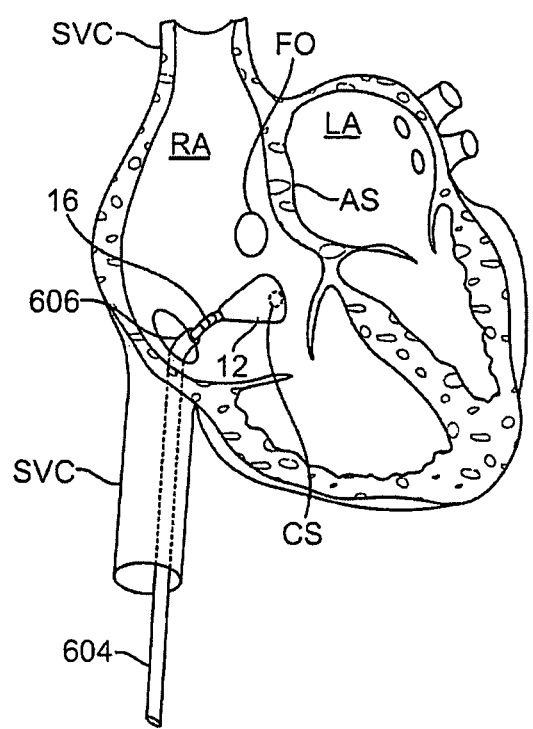
FIGS. 65A and 65B show perspective and partial cross-sectional side views, respectively, of the imaging hood positioned over the coronary sinus along the septal wall.
Figure 65B:
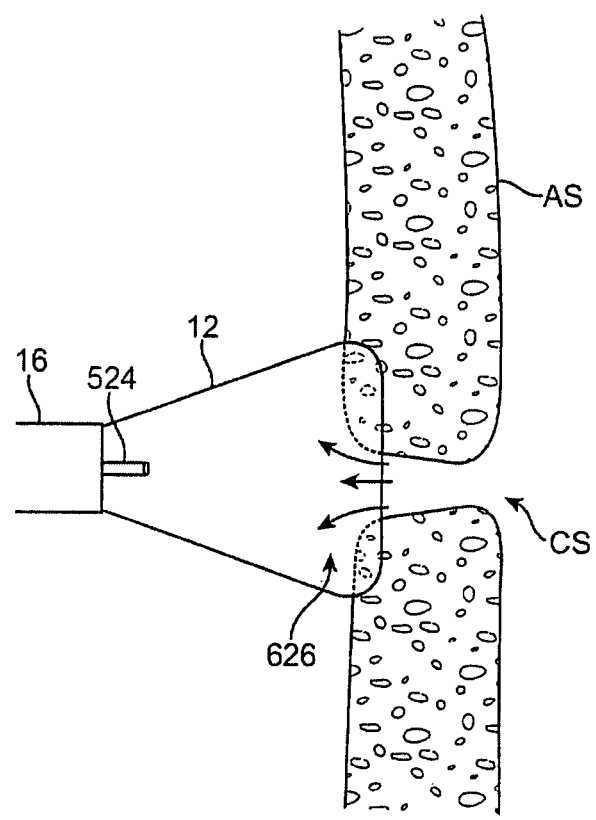
Figure 65C:
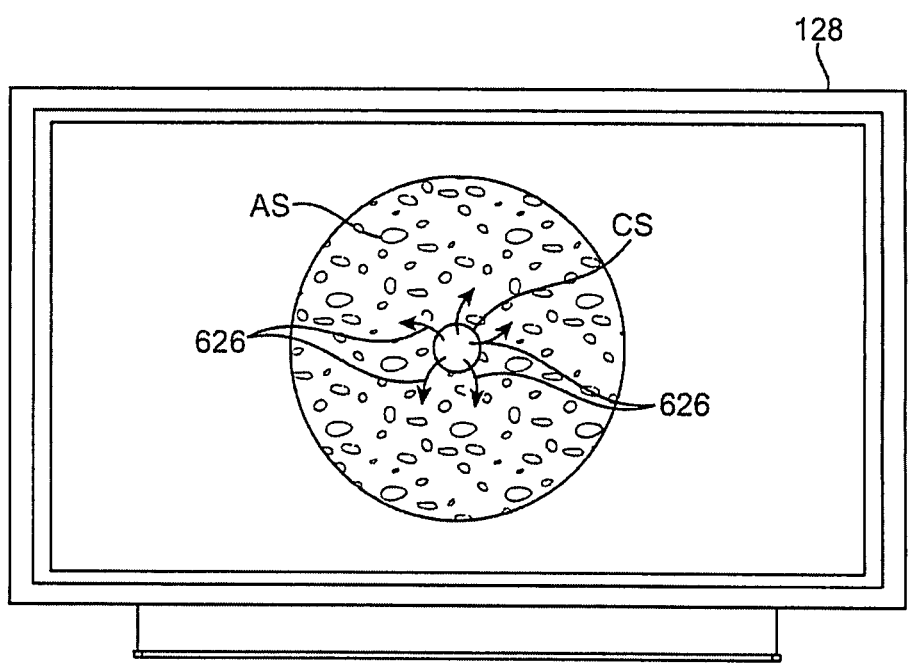
FIG. 65C illustrates the ostium of the coronary sinus and the in-flow of blood into the imaging hood under visualization through the imaging hood.

Another example of visually distinguishing anatomical landmarks may also include visualization of the coronary sinus CS ostium, located inferiorly to the fossa ovalis FO. As above, imaging hood 12 may be translated along the tissue wall of the atrial septum AS while under direct visualization through hood 12 until the ostium of the coronary sinus CS is located, as shown in FIG. 65A. A position of hood 12 over the coronary sinus CS may be confirmed by the visualization of blood flow 626 entering hood 12, as shown in FIG. 65B. With the in-flow of blood 626 into hood 12, visualization of the ostium may begin to become obscured as the blood 626 enters the visualization field in which case additional translucent fluid may be injected into hood 12 to maintain unobscured visualization. FIG. 65C shows an image displayed upon monitor 128 which has been captured within hood 12 illustrating the underlying tissue and the ostium of the coronary sinus CS with the in-flow of blood 626 entering the visualization field within hood 12. Visually identifying the coronary sinus CS, which is a feature in close proximity to the fossa ovalis FO, may further serve as a confirmation of the location of the fossa ovalis FO.

Figure 66A:
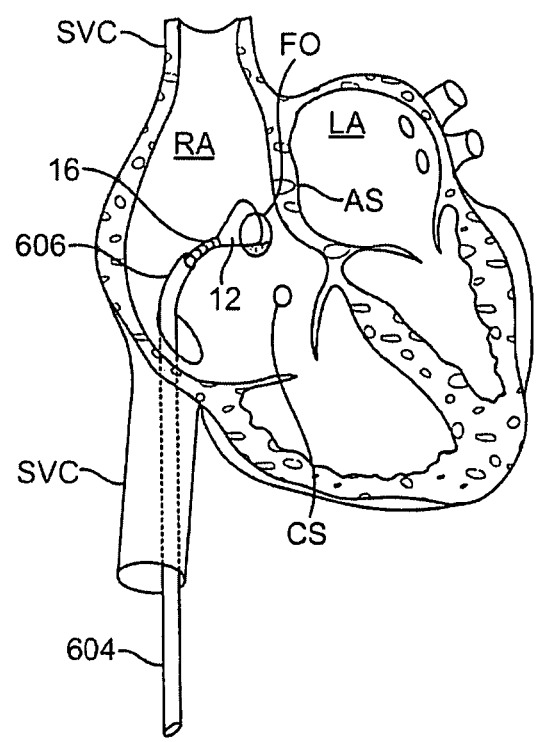
FIGS. 66A and 66B show perspective and partial cross-sectional side views, respectively, of the imaging hood positioned over the fossa ovalis along the septal wall while directly visualizing an atrial septal aneurysm in real-time.
Figure 66B:
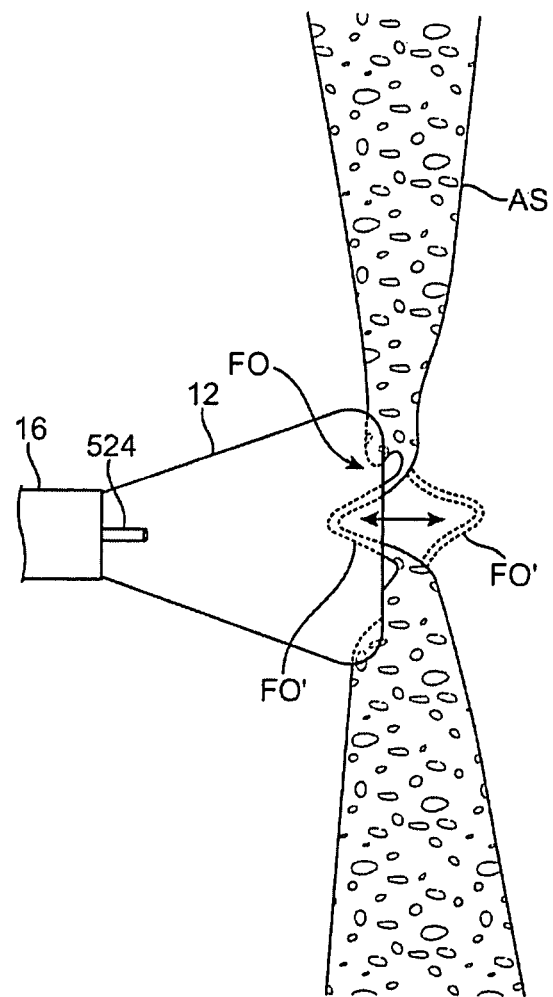

In yet another example, imaging hood 12 may be positioned along, adjacent to, or directly upon the fossa ovalis FO, as above and as shown in FIG. 66A, where conditions of the fossa ovalis FO may be ascertained by visual examination. One condition which may be directly visualized within hood 12 is an atrial septal aneurysm, which is a localized deformity of the atrial septum AS where the fossa ovalis FO' may bulge or oscillate between the left and right atrial chambers of the heart while beating, as illustrated in the partial cross-sectional view of FIG. 66B. Such a condition may be visualized through hood 12 in real-time enabling the user to view the movement of the fossa ovalis FO' and to treat it as appropriate.

Figure 67A:
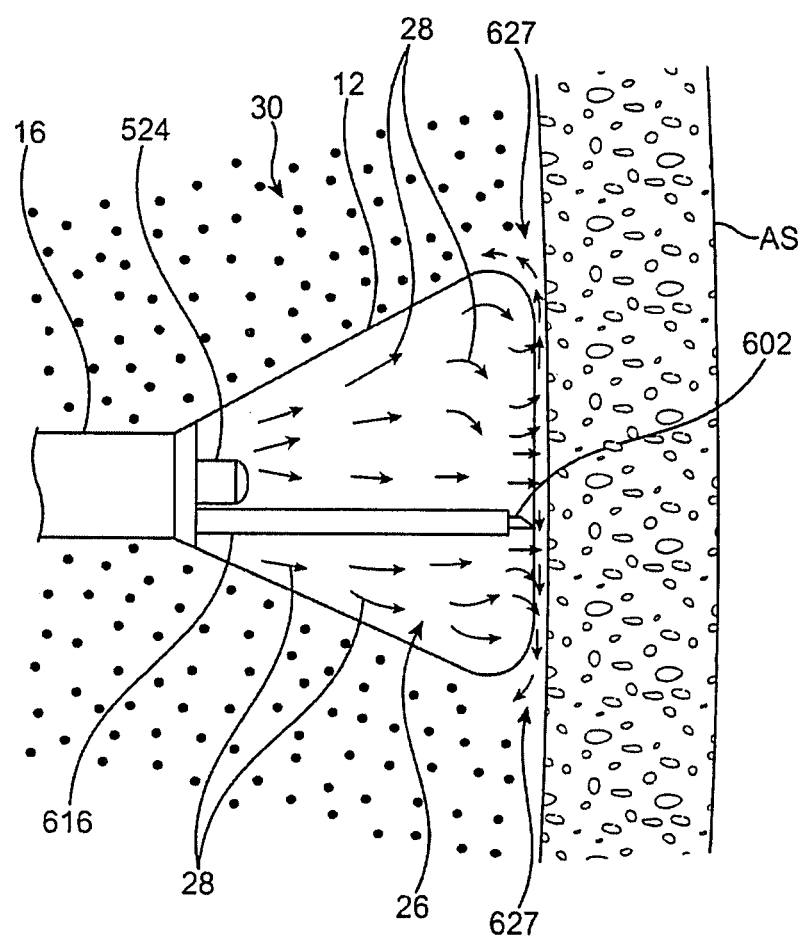
FIGS. 67A and 67B illustrate partial cross-sectional side views of a piercing instrument passing transseptally under direct visualization without tenting or distorting the underlying tissue.
Figure 67B:
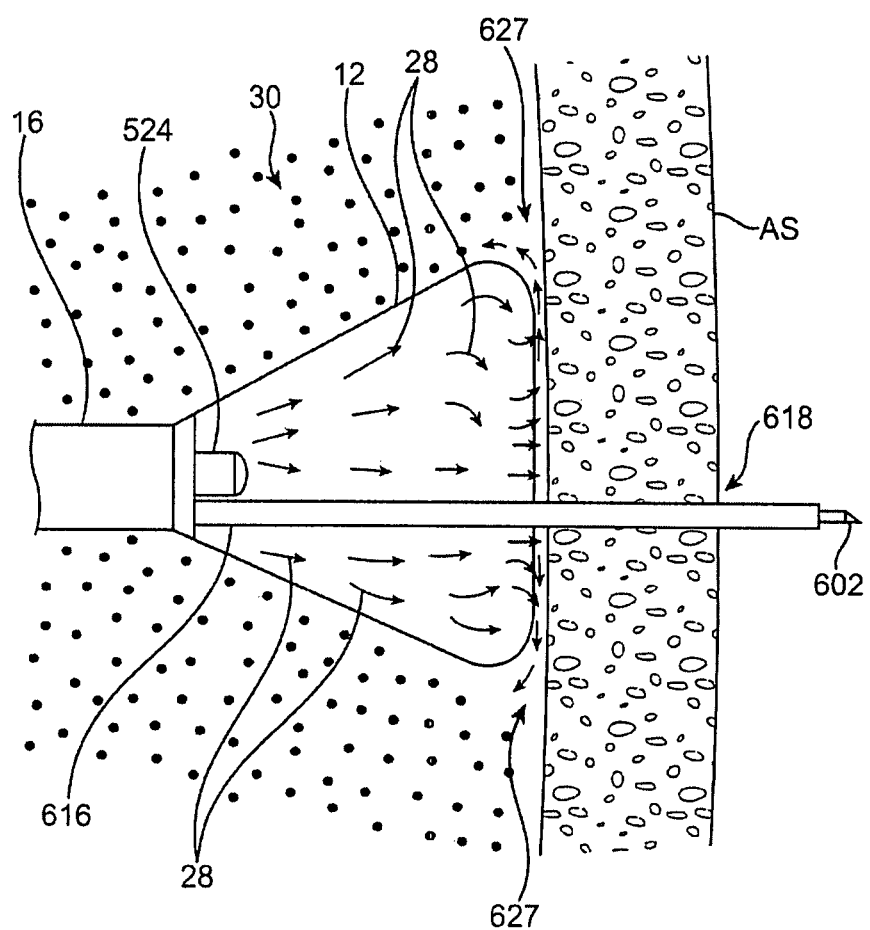

As mentioned above, the imaging hood 12 may be utilized to indicate whether an excessive amount of force is imparted upon the tissue wall during a therapeutic procedure such as transseptal puncture. As also described above, in the case of transseptal puncture, once the open area 26 of imaging hood 12 has been deployed against or adjacent to the region of tissue to be imaged, the translucent fluid 28 may be pumped into the hood 12 via the deployment catheter 16 such that the surrounding opaque fluid, such as blood 30 is displaced from within the hood 12 and the underlying tissue may then be visualized through the translucent fluid 28. A needle sheath 616 and a piercing tip 602 projecting therefrom may be advanced through the hood 12 and pierced into or through the tissue creating a transseptal puncture 618 to access the body lumen, such as the left atrium, beyond the atrial septum AS while under the direct visualization of imager 524, as shown in FIGS. 67A and 67B. As hood 12 and the tissue wall contact and form a temporary seal 627, the out-flow of translucent fluid 28 from hood 12 may be permitted through seal 627 while the in-flow of surrounding blood 30 into the hood open field 26 is inhibited or prevented even when the tissue is punctured.

Figure 68A:
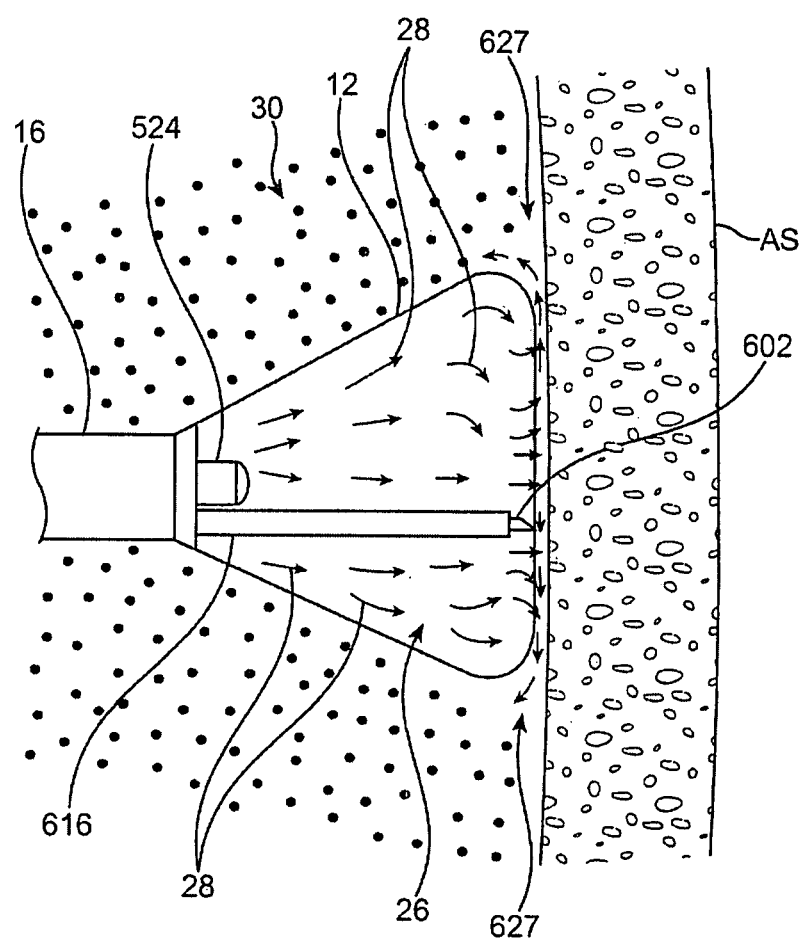
FIGS. 68A and 68B illustrate partial cross-sectional side views of a piercing instrument passing transseptally under direct visualization where tenting or distortion of the underlying tissue occurs and is visually detected.
Figure 68B:
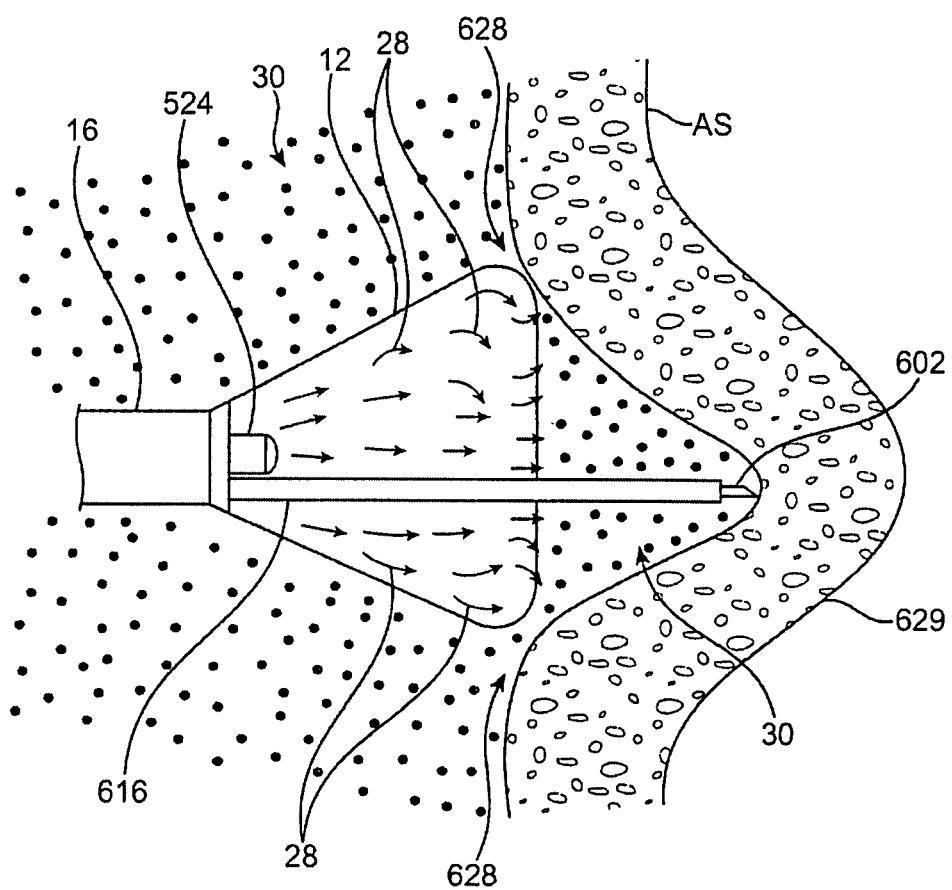

However, in cases where piercing tip 602 is advanced against the tissue wall and fails to pierce into or through the atrial septum AS, the underlying tissue may begin to distort or tent around the piercing instrument, as shown in FIGS. 68A and 68B. When the tissue begins tenting away from the piercing instrument, aside from the tactile feedback that the physician may experience, the lip of the imaging hood 12 may begin to lose contact with the underlying tissue surface. As the seal 628 between hood 12 and the tissue is broken, the surrounding blood 30 may begin to seep into the interior of the hood 12 and into the visualization field 26 where it may begin to dilute in the translucent fluid 28. This blood seepage may be immediately noticeable under direct visualization due to the contrast in color change to the user and may serve as a clear visual indicator that excessive tension may be imparted by the piercing instrument upon the underlying tissue and that distortion and tenting of the tissue 629 may be occurring. With this early visual sign of tissue tension, the user may accordingly adjust the amount of force imparted upon the tissue, substitute another piercing instrument, or he/she may stop the procedure and relocate the imaging hood 12 to another location along the septal wall which may be more suitable for performing a transseptal puncture. Thus, monitoring visualization field within the open area of the hood 12 for the presence of opaque fluid seepage therewithin is indicative of excess distortion of the region of tissue by the piercing instrument.

Figure 69A:
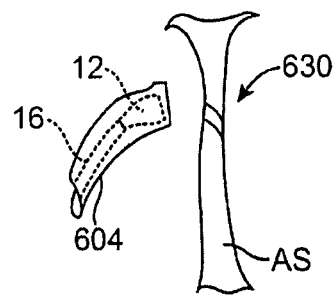
FIGS. 69A to 69C illustrate a method for advancing the imaging hood itself transseptally.
Figure 69B:
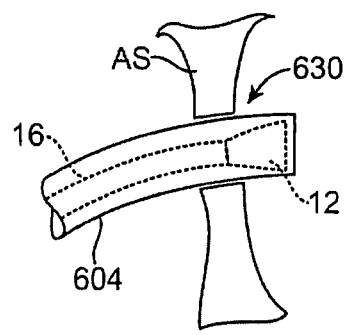
Figure 69C:
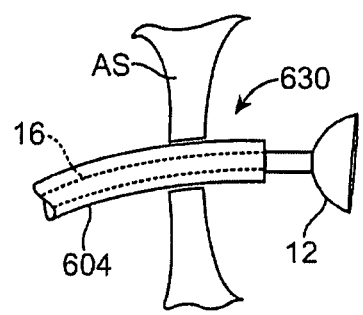

In yet another variation for utilizing the deployment catheter 16 and imaging hood 12, the catheter 16 may be used to facilitate the crossing of the tissue wall, e.g., through an atrial-septal defect (ASD) or patent foramen ovale (PFO) or through an artificially-created transseptal puncture or fistula. As illustrated in FIGS. 69A to 69C, deployment catheter 16 and hood 12 may be articulated to identify a region of tissue, particularly a septal defect such as PFO 630 along the atrial septum AS. Once identified by direct visualization as described above, the introducer sheath 604 may be advanced distally over deployment catheter 16 and hood 12 to retract the hood 12 into its low-profile configuration, as shown in FIG. 69A. Then, utilizing guidewire 17 or by simply urging the sheath 604 and deployment catheter 16 distally through the opening 630, as shown in FIG. 69B, the deployment catheter 16 and imaging hood 12 may be penetrated to access the opposite body lumen, such as the left atrium LA. Once the distal opening of sheath 604 is cleared of opening 630, deployment catheter 16 and imaging hood 12 may be projected from sheath 604 to allow the imaging hood 12 to redeploy into its expanded configuration, as shown in FIG. 69C.

In utilizing the imaging hood 12 in any one of the procedures described herein, the hood 12 may have an open field which is uncovered and clear to provide direct tissue contact between the hood interior and the underlying tissue to effect any number of treatments upon the tissue, as described above. Yet in additional variations, imaging hood 12 may utilize other configurations, as also described above.

Figure 70B:
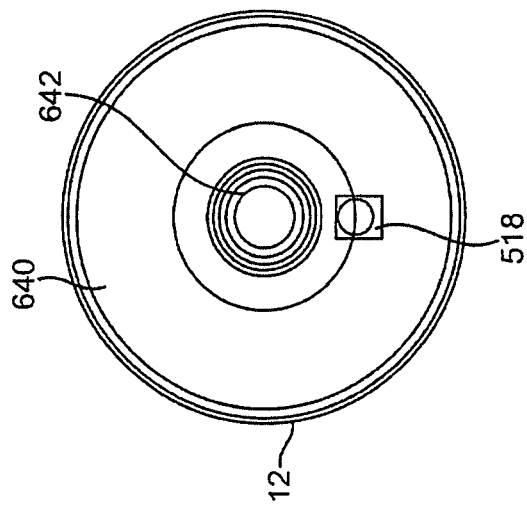
FIGS. 70A and 70B show perspective and end views, respectively, of an imaging hood having at least one layer of a transparent elastomeric membrane over the distal opening of the hood.
Figure 70A:
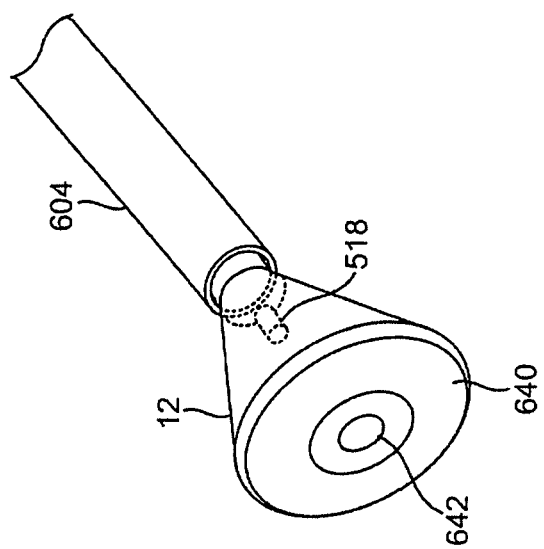

An additional variation of the imaging hood 12 is shown in the perspective and end views, respectively, of FIGS. 70A and 70B, where imaging hood 12 includes at least one layer of a transparent elastomeric membrane 640 over the distal opening of hood 12. An aperture 642 having a diameter which is less than a diameter of the outer lip of imaging hood 12 may be defined over the center of membrane 640 where a longitudinal axis of the hood intersects the membrane such that the interior of hood 12 remains open and in fluid communication with the environment external to hood 12. Furthermore, aperture 642 may be sized, e.g., between 1 to 2 mm or more in diameter and membrane 640 can be made from any number of transparent elastomers such as silicone, polyurethane, latex, etc. such that contacted tissue may also be visualized through membrane 640 as well as through aperture 642.

Aperture 642 may function generally as a restricting passageway to reduce the rate of fluid out-flow from the hood 12 when the interior of the hood 12 is infused with the clear fluid through which underlying tissue regions may be visualized. Aside from restricting out-flow of clear fluid from within hood 12, aperture 642 may also restrict external surrounding fluids from entering hood 12 too rapidly. The reduction in the rate of fluid out-flow from the hood and blood in-flow into the hood may improve visualization conditions as hood 12 may be more readily filled with transparent fluid rather than being filled by opaque blood which may obstruct direct visualization by the visualization instruments.

Moreover, aperture 642 may be aligned with catheter 604 such that any instruments (e.g., piercing instruments, guidewires, tissue engagers, etc.) that are advanced into the hood interior may directly access the underlying tissue uninhibited or unrestricted for treatment through aperture 642. In other variations wherein aperture 642 may not be aligned with catheter 604, instruments passed through catheter 604 may still access the underlying tissue by simply piercing through membrane 640.

Figure 70C:
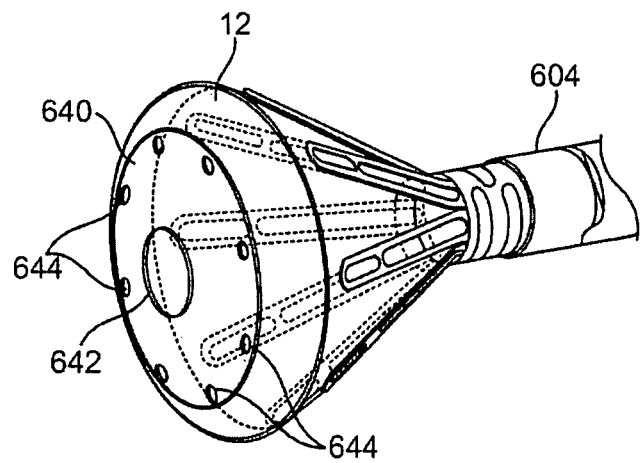
FIGS. 70C and 70D show perspective and end views, respectively, of an imaging hood which includes a membrane with an aperture defined therethrough and a plurality of additional openings defined over the membrane surrounding the aperture.
Figure 70D:
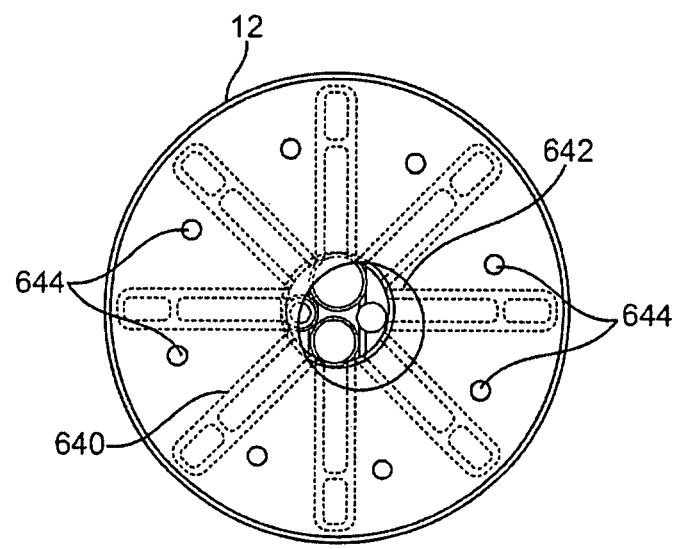

In an additional variation, FIGS. 70C and 70D show perspective and end views, respectively, of imaging hood 12 which includes membrane 640 with aperture 642 defined therethrough, as described above. This variation includes a plurality of additional openings 644 defined over membrane 640 surrounding aperture 642. Additional openings 644 may be uniformly sized, e.g., each less than 1 mm in diameter, to allow for the out-flow of the translucent fluid therethrough when in contact against the tissue surface. Moreover, although openings 644 are illustrated as uniform in size, the openings may be varied in size and their placement may also be non-uniform or random over membrane 640 rather than uniformly positioned about aperture 642 in FIG. 70D. Furthermore, there are eight openings 644 shown in the figures although fewer than eight or more than eight openings 644 may also be utilized over membrane 640.

Figures 71A, 71B:
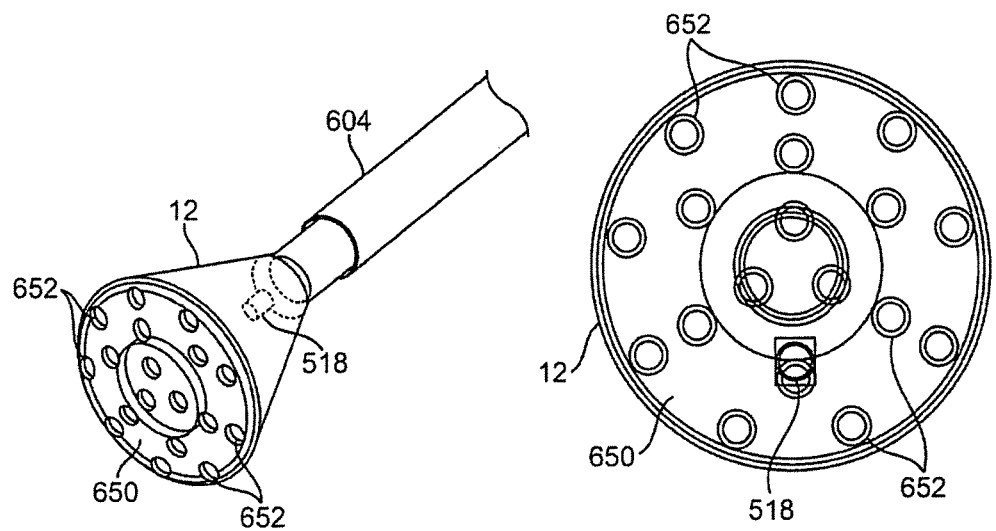
FIGS. 71A and 71B show perspective and end views, respectively, of an imaging hood having a double-layered membrane covering the end of the hood where the membrane defines a plurality of flow reduction apertures.
Figures 72A, 72B:
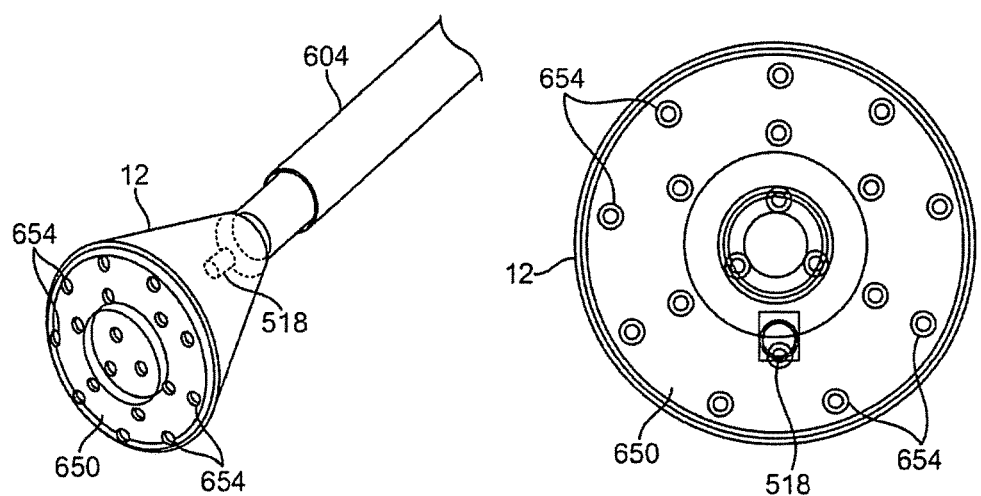
FIGS. 72A and 72B show perspective and end views, respectively, of the imaging hood of FIGS. 71A and 71B where the flow reduction apertures are reduced in size by pressurizing the space between the membranes.

FIGS. 71A and 71B show perspective and end views, respectively, of another variation of imaging hood 12 where a double-layered membrane 650 may cover the end of hood 12. Double-layered membrane 650 may define a plurality of flow reduction apertures 652 through the double-layered membrane 650 where each aperture 652 has a first diameter, e.g., about 1 mm or more in diameter. The diameter of these flow reduction apertures 652 can be reduced in size, e.g., less than 1 mm, or closed entirely by inflating the space between the double-layered membrane with a pressurized fluid or gas such that the apertures 654 result in a second reduced diameter, as shown in the perspective and end views, respectively, of FIGS. 72A and 72B, relative to the un-pressurized openings 652. With respect to positioning of the apertures 652 over membrane 650, the number of openings may be varied and uniform or non-uniform with respect to relative positioning of the openings.

The reduction or closure of the flow reduction apertures 654 may facilitate the sealing of the hood 12 quickly due to the relatively small sized pores and the ability to potentially better distribute clear fluid out-flow over the distal cross sectional area of the hood 12 due to the plurality of small apertures rather than a single central aperture. Moreover, therapeutic instruments can be passed through the membrane 650 through any of the apertures 652 for treating the underlying tissue.

Figures 73A, 73B:
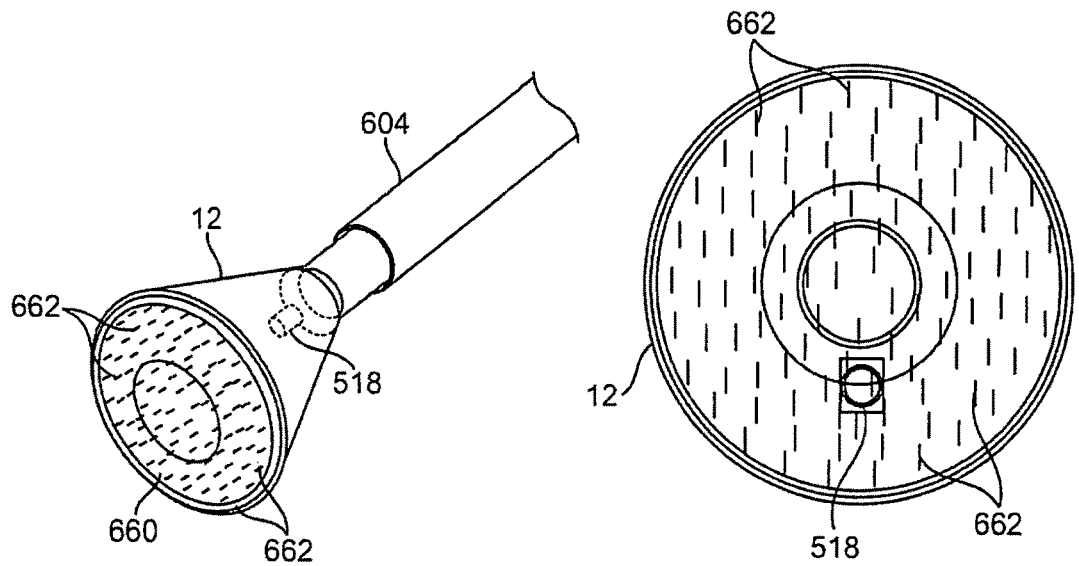
FIGS. 73A and 73B show perspective and end views, respectively, of an imaging hood having a plurality of slits defined over the membrane covering the end of the hood.
Figures 74A, 74B:
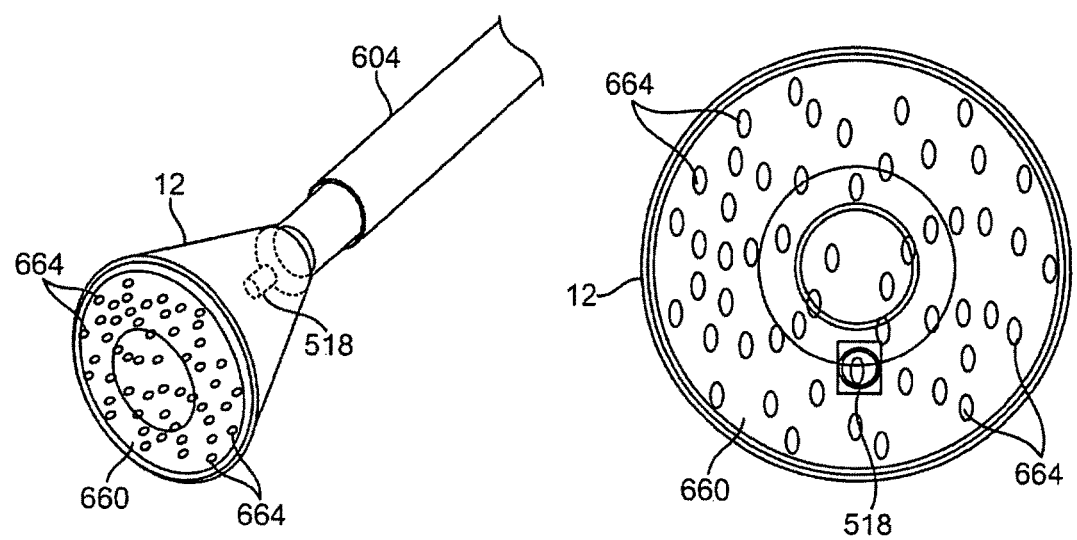
FIGS. 74A and 74B show perspective and end views, respectively, of the imaging hood of FIGS. 73A and 73B where the slits are opened by increased fluid pressure within the hood.

FIGS. 73A and 73B show perspective and end views, respectively, of another variation where a slitted membrane 660 may cover the distal opening of hood 12. The plurality of slits 662 over the membrane 660 may remain closed to facilitate the initial introduction of the clearing fluid into the hood 12 and also to inhibit the seepage of blood into the hood 12 visualization field. However, as internal pressure of the fluid within hood 12 increases as additional saline is injected into the interior of hood 12, the plurality of slits may be opened by the membrane 660 stretching, as shown by the opened apertures 664 in the perspective and end views, respectively, of FIGS. 74A and 74B. Any number of therapeutic instruments may be deployed through the membrane 660 through any of the opened apertures 664 to treat the underlying tissue. Alternatively, the instruments may be simply pierced through membrane 660 to access the underlying tissue.

Figure 75A:
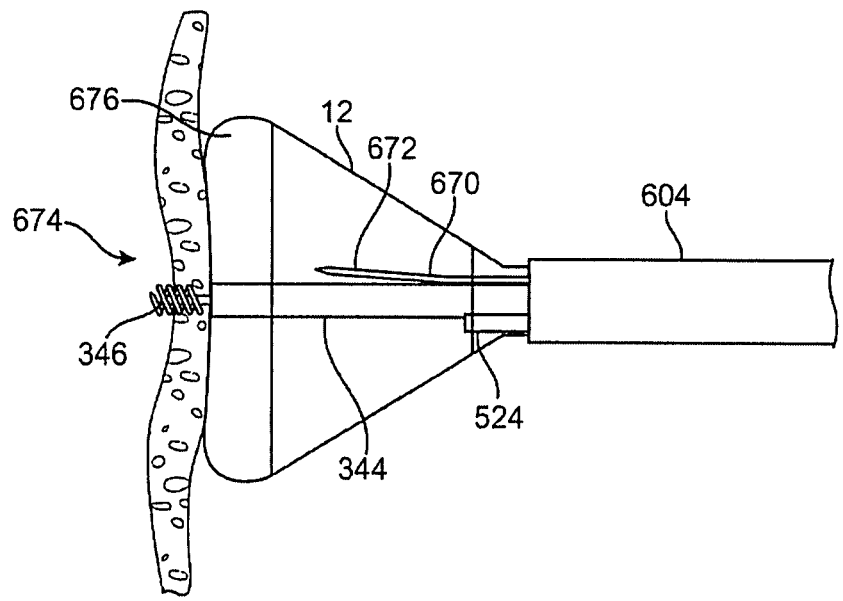
FIGS. 75A and 75B show side views of an imaging hood having an inflatable balloon tip that may be inflated with a clear fluid and which may be pierced through via a needle from within the imaging hood.

In yet another variation of a hood 12 configured to facilitate the introduction of the purging fluid within the visual field, FIG. 75A shows a variation of imaging hood 12 having an inflatable balloon tip 676 that may inflated with a clear fluid such as the fluid used to purge the visualization field within hood 12. The catheter 604 may house a penetrative needle 672 contained within needle sheath 670 which may be utilized for tissue treatment and/or transseptal access. With the balloon tip 676 in contact with the target tissue 674, visualization of the tissue surface may be accomplished through imaging hood 12 as well as through the balloon tip 676.

Figure 75B:
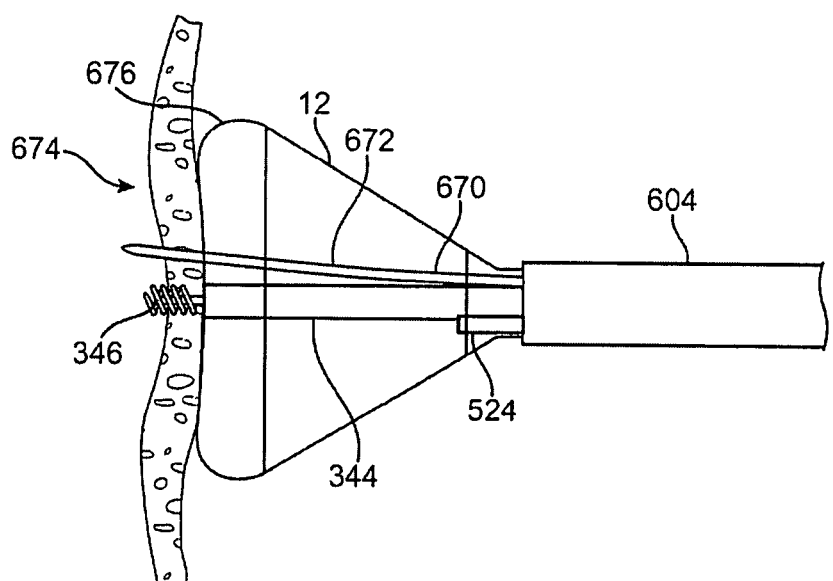

To access the underlying tissue, needle 672 may be advanced from needle sheath 670 from within imaging hood 12 to penetrate through balloon 676 directly to the target tissue 674, as shown in FIG. 75B. Because penetrative needle 672 may be sized to have a relatively small diameter, the penetration of needle 672 into and through balloon 676 will not cause the balloon 676 to burst or the clear fluid to leak when inserted gently. The needle 672 may be inserted into the underlying tissue over a wide range of angles for more precise access to the treatment region.

Figure 76:
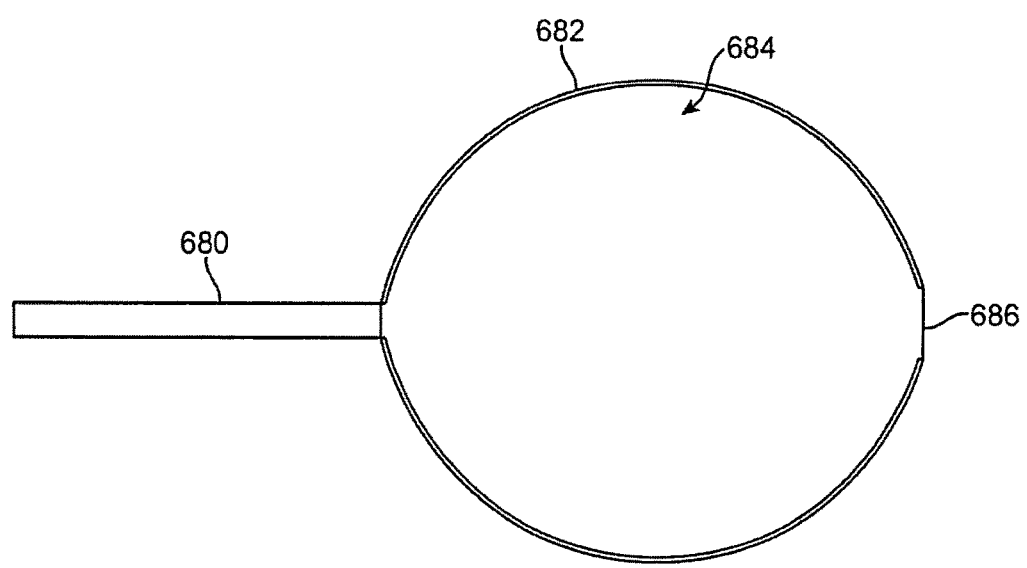
FIG. 76 shows a partial cross-sectional view of a partially-inflatable balloon member extending from the catheter shaft and having a distally located opening in the balloon for placement against the tissue surface.
Figure 77A:
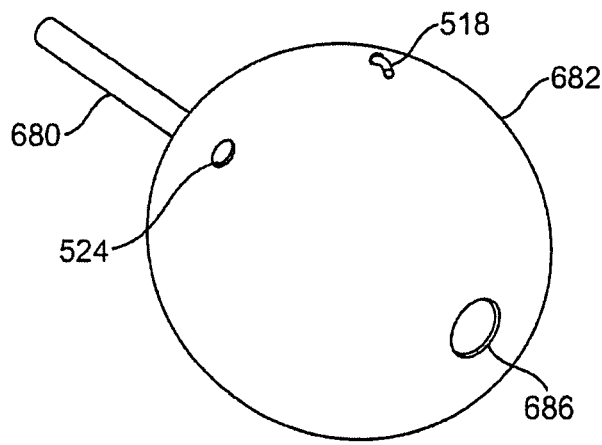
FIG. 77A shows a perspective view of the partially inflatable structure of FIG. 76 showing the opening.

Aside from utilizing a hooded structure, various other structures may be utilized for transseptal access within the heart. FIG. 76 shows a partial cross-sectional view of a partially-inflatable balloon member 682 extending from the catheter shaft 680 and having a distally located opening 686 in the balloon for placement against the tissue surface. Such a partially inflatable structure may be filled with a clear fluid, such as saline to clear the imaging field of blood within the membrane as above, while the opening 686 is placed against the tissue surface to provide access thereto. The balloon structure 682 may be formed of a distensible material or a non-distensible polymeric material which may expand from a collapsed configuration. In either case, the balloon material may be either an opaque or transparent material to facilitate imaging therethrough of any surrounding anatomical structures. FIG. 77A shows a perspective view of the partially inflatable structure showing the opening 686, and examples of imaging devices 524 which may be positioned within the catheter shaft 680 for viewing within the membrane in an in-line view. Alternatively, an imager 518 such as a CMOS or CCD imager, as discussed above, may be positioned along an interior surface of the membrane to provide an off-axis image within the balloon membrane 682 and/or the tissue surface in contact against the opening 686.

Figure 77B:
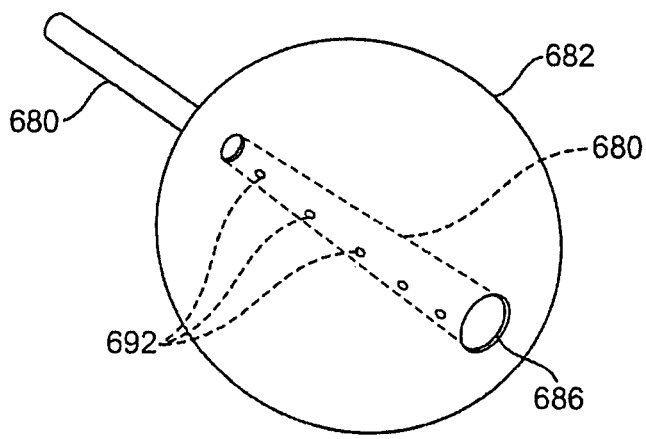
FIG. 77B shows a perspective view of another variation of the partially inflatable structure having a lumen or passageway defined through the structure.

In yet another variation, the inflatable structure 682 may also include a lumen or passageway 690 defined through the structure maintaining a passageway from the catheter 680 to the balloon opening 686 such that instruments passed through the structure may have an unimpeded or direct path to the underlying tissue, as shown in FIG. 77B. Moreover, the lumen 690 may be optionally configured, e.g., via one or more openings 692, to allow for the infusion of the clearing fluid through the lumen 690 and the balloon 682 to facilitate imaging therethrough. The lumen material may be made from a similar or the same material as the balloon and may also be translucent to further facilitate imaging therethrough.

Figure 77C:
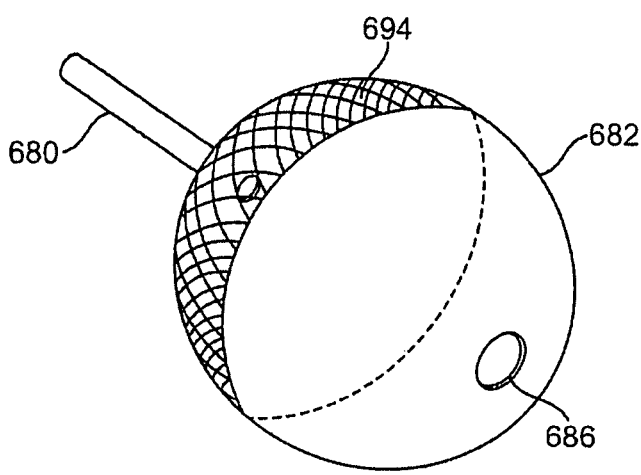
FIG. 77C shows a perspective view of another variation of the partially inflatable structure having a reinforced portion integrated with the balloon material.

Although the membrane of the partially-inflatable balloon may be formed of a uniform material, a proximal portion, e.g., a proximal hemispherical portion, may be reinforced with an additional layer 694, such as cloth, as shown in FIG. 77C. Alternatively, the proximal reinforced portion 694 may have a braided or weaved material integrated with the balloon material to provide additional structural integrity as the balloon is pressed against tissue.

Figure 78A:
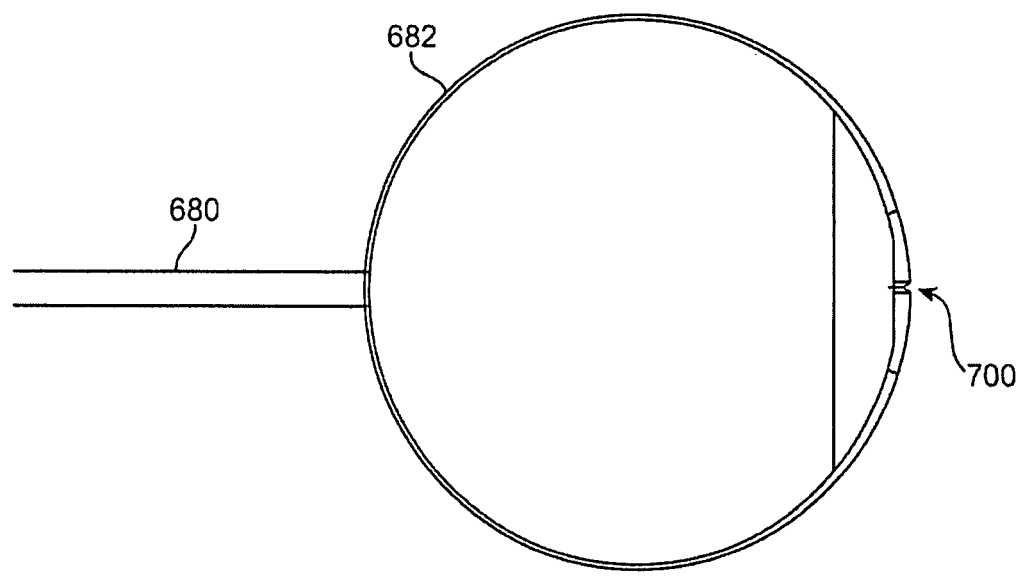
FIGS. 78A and 78B show partial cross-sectional side and perspective views, respectively, of a balloon structure having a flapped valve at its distal end.

Additional variations on the inflatable balloon structure may be seen in the partial cross-sectional side view of FIG. 78A, which illustrates a balloon member 682 having a valve 700, e.g., a flapped valve, at its distal end which may allow for the infusion of clear fluids within the balloon 682 and out through the valve 700 to clear the imaging field. The balloon 682 may be pressed against underlying tissue and instruments may be passed through the valve 700 while allowing for only a minimal amount of blood to seep back into the balloon structure such that a clear imaging field may be maintained.

Figure 78B:
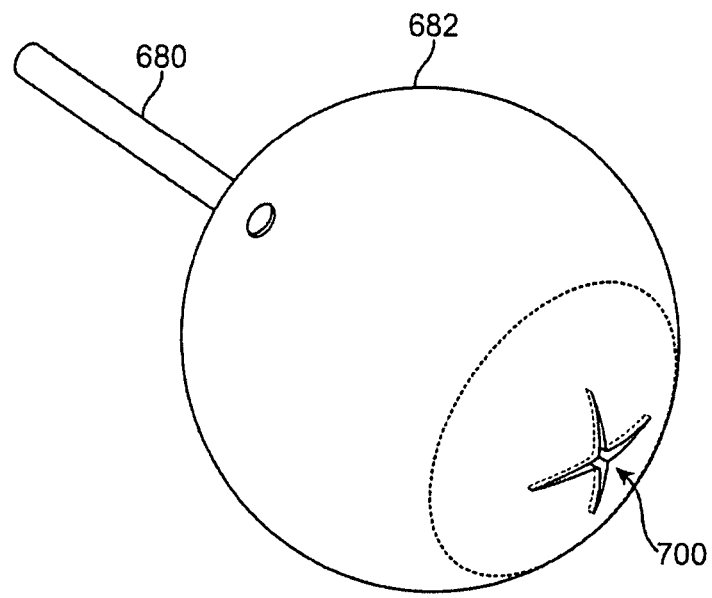
Figure 79A:
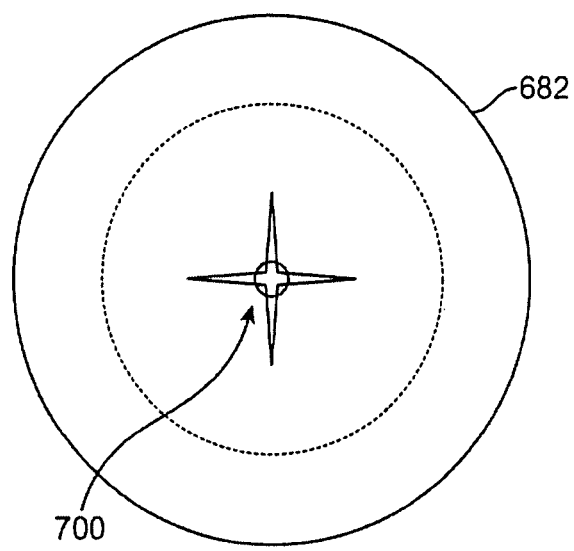
FIGS. 79A and 79B show end views of the flapped valve in its partially open and closed configurations, respectively.
Figure 79B:
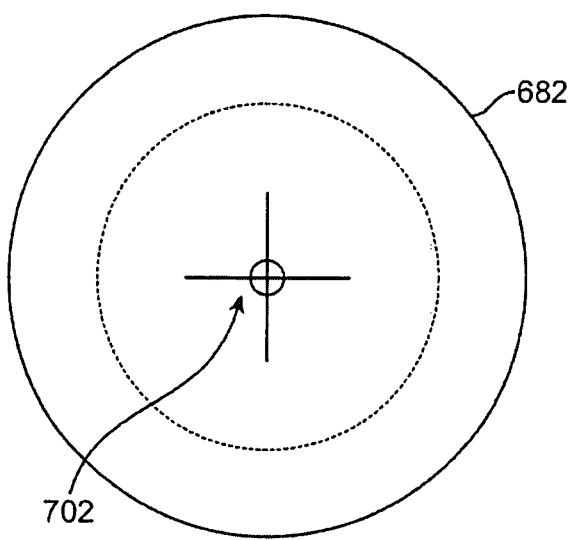

FIG. 78B shows a perspective view of the balloon structure 682 having the flapped valve 700. FIGS. 79A and 79B both show end views of the inflated balloon structure 682, respectively, having the valve in a partially opened configuration 700 when fluid is infused therethrough or when instruments are passed and when the valve is closed 702 minimizing the flow of blood seepage into the balloon 682 or clearing fluid out of the balloon.

Figure 80A:
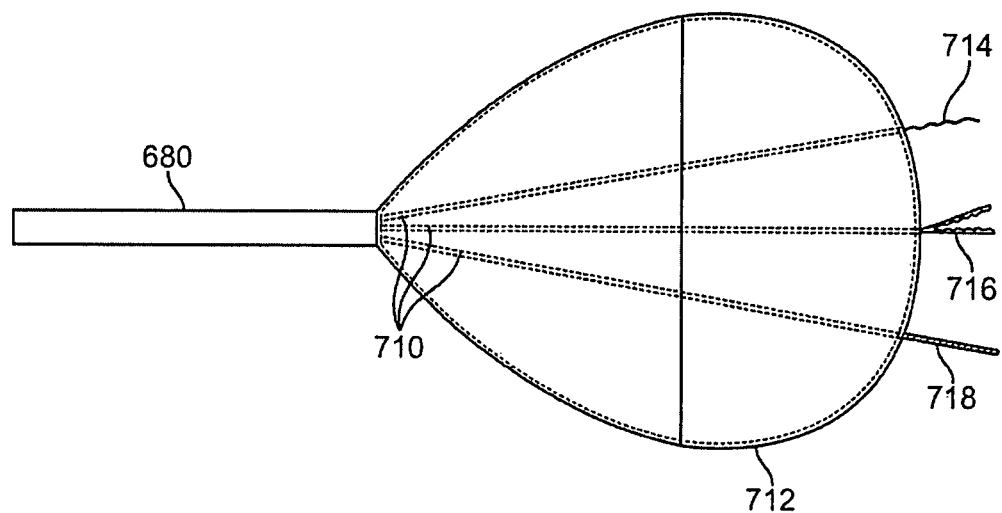
FIGS. 80A and 80B side and perspective views, respectively, of an inflatable balloon structure having one or more instrument lumens defined therethrough.
Figure 80B:
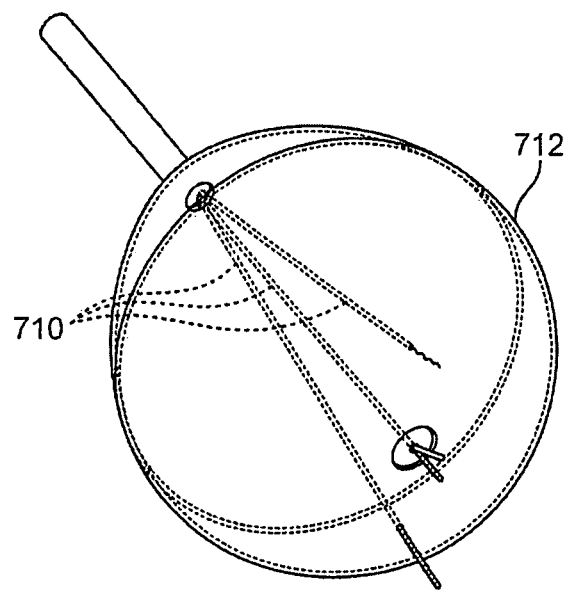

FIG. 80A shows a side view of yet another variation of an inflatable balloon or structure 712 having one or more instrument lumens 710 defined therethrough extending from the catheter 680 to a corresponding opening located on a distal end portion of the balloon member 712. The balloon member 712 may be inflated with a clearing fluid while the imager may be positioned within the balloon member 712 within the catheter 680 or within one of the instrument lumens 710. As illustrated, one or more instruments may be passed through the lumens 710, such as a helical engager 714, graspers 716, an RF ablation probe 718, etc., to perform any number of procedures on the underlying tissue. Moreover, the balloon structure 712 may be partially open to allow for the infused fluid to pass through. FIG. 80B shows a perspective view of the assembly of FIG. 80A.

Figure 81A:
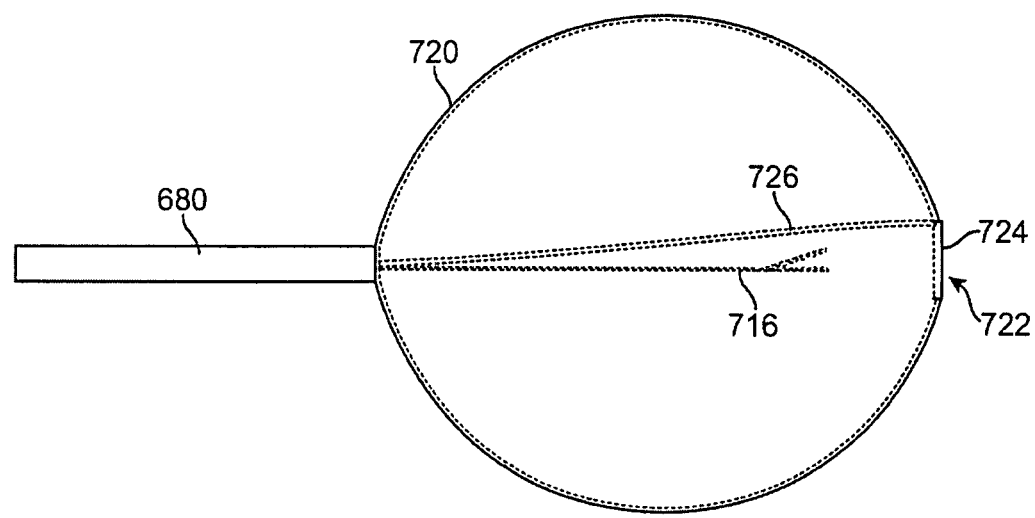
FIGS. 81A and 81B show side and perspective views, respectively, an inflatable balloon structure having an opening reinforced via ring and an elongate member projection from the catheter.
Figure 81B:
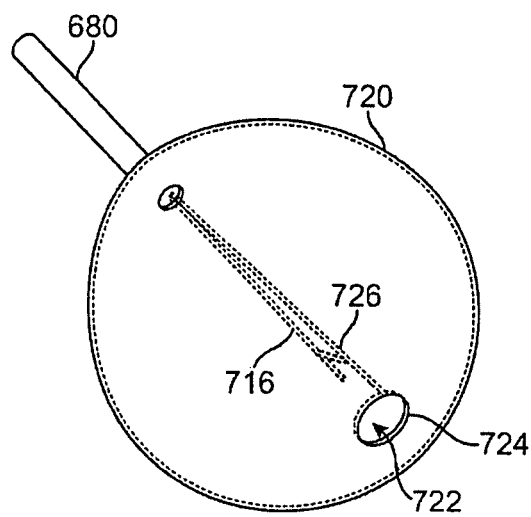

FIG. 81A shows yet another variation of an inflatable structure 720 having an opening 722 reinforced via a ring 724 and an elongate member 726 projecting from the catheter 680. To expand the membrane, the ring structure 724 may be urged distally via the elongate member 726 to allow the membrane to reconfigure from a low-profile shape to its expanded shape. Once expanded, the clearing fluid may be infused within the structure 720 to clear the imaging field. Additionally, one or more instruments, e.g., graspers 716, may be advanced through the catheter 680 and into the structure 720 to access the underlying tissue within the ringed opening 722. FIG. 81B shows a perspective view of the assembly of FIG. 81A illustrating the opening 722 and the ring structure 724.

Figure 82A:
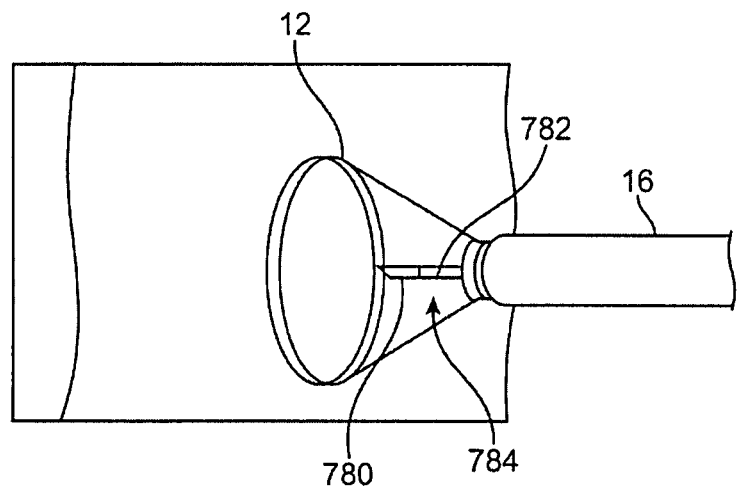
FIGS. 82A and 82B show perspective views of the tissue visualization catheter with a needle body positioned therethrough having multi-colored gradations or markings along its shaft extending from the needle tip used in conjunction with the tissue visualization catheter.
Figure 82B:
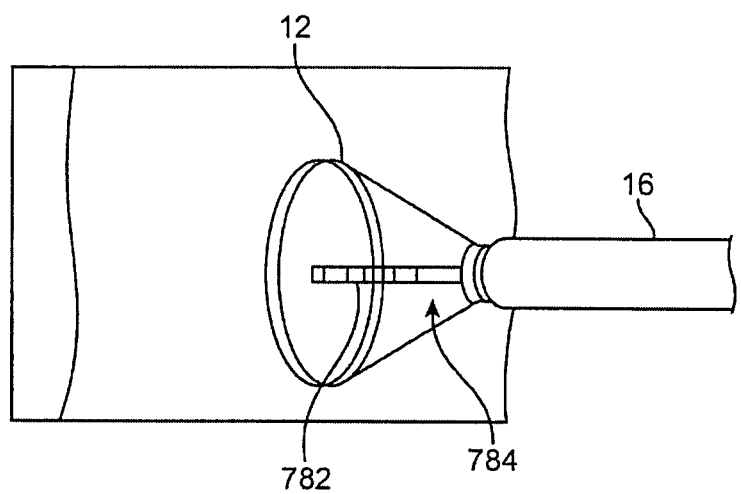

Yet another feature which may be utilized with any of the embodiments described above, particularly for transseptal puncture, is shown in FIGS. 82A and 82B, which show perspective views of the tissue visualization catheter with a needle body 782 positioned therethrough having multi-colored gradations or markings 784 along its shaft extending from the needle tip 780 used in conjunction with the tissue visualization catheter. The needle 782 can be of varying sizes and diameters with segments along the body 782 marked with different colors 784. The needle 782 may also have markings or gradations engraved or otherwise marked along the body of the needle to visually indicate a length of the needle in millimeters or inches.

FIG. 82B shows the perspective view of the colored needle 782 at least partially inserted into the tissue, whereby the operator may gauge the depth of needle penetration into the tissue by correlating the exposed colored gradations or markings 784. When the needle penetrates the tissue, the exposed markings 784 just above the tissue surface can be read under direct visualization provided by the tissue visualization catheter. Direct visualization is achieved by the CCD/CMOS camera built-in the catheter and by flushing opaque bodily fluid such as blood, out of the interior of the hood using clear saline, as described above.

Another method for determining depth of tissue penetration with the colored needle body 782 may utilize estimating the depth of penetration from the colored segment that is advanced into the tissue and no longer visible by the imaging element. For example, the colors may be coded to indicate a range of safe tissue penetration by the needle body 782. An example of this is to delineate a proximal portion of the needle body 782 as a safety limit of how far the needle may be penetrated into the tissue. As the needle 782 is advanced into the tissue, the operator may continue the advancement until, e.g., a red segment of the needle has been reached. Other portions of the needle body 782 may be color-coded in a likewise manner, e.g., having a green segment along the needle body 782 distal to the red safety limit to indicate a safe range in which to advance the needle. Such features may be utilized as a safety feature especially when the tissue visualization catheter is used for tissue puncture related procedures such as transseptal access within the heart.

FIGS. 83A to 83E illustrates a variation for transseptal access where a Veres-type needle 790 having an atraumatic blunt end 792 within a piercing needle may be advanced intravascularly for penetrating through the septal wall AS and for passing a guidewire 17 through the needle. The Veres-type needle 790 may be advanced through the catheter and imaging hood 12 (not shown for clarity) similar to the manner shown above in FIGS. 60A to 60F in which case the shaft of needle 790 is suitably flexible for intravascular advancement. Use of such a needle 790 may enhance safety of the procedure in preventing or inhibiting the accidental puncture of tissue with a deployed needle within the heart.

Figure 83A:
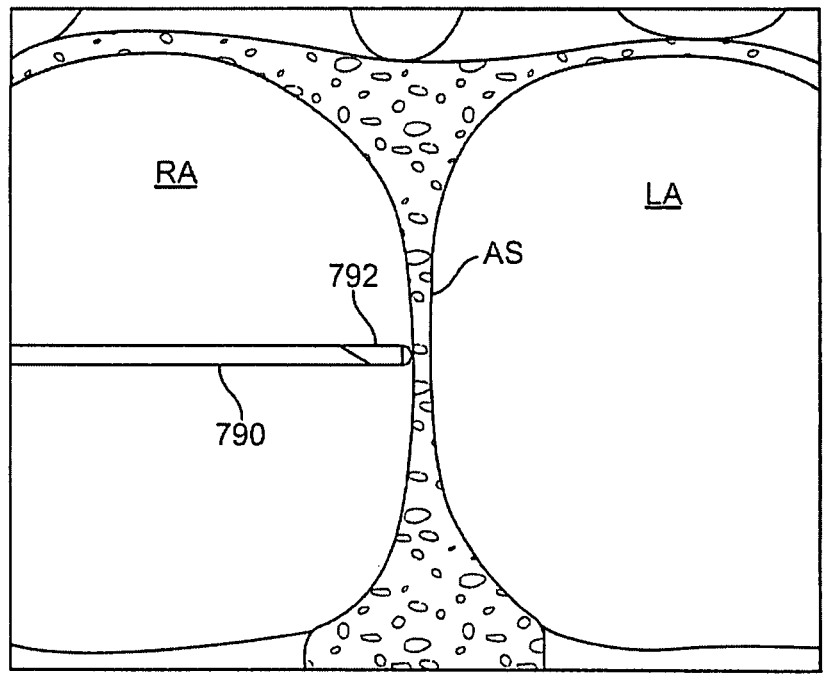
FIGS. 83A to 83E illustrates a variation for transseptal access where a Veres-type needle having an atraumatic blunt end within a piercing needle may be advanced intravascularly for penetrating through the septal wall and for passing a guidewire through the needle.
Figure 83B:
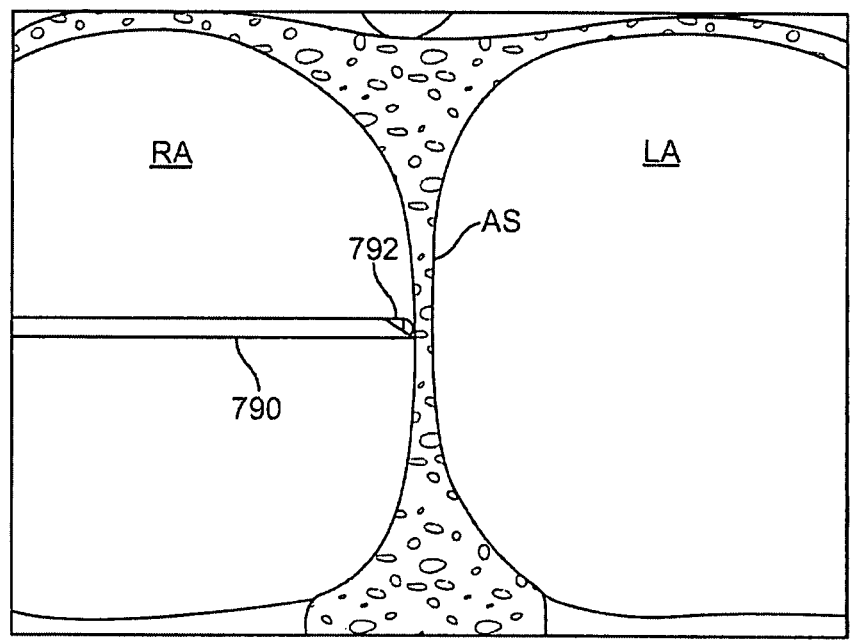
Figure 83C:
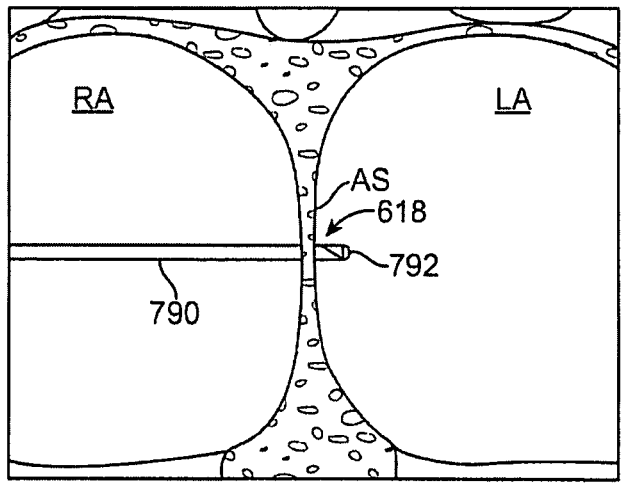
Figure 83D:
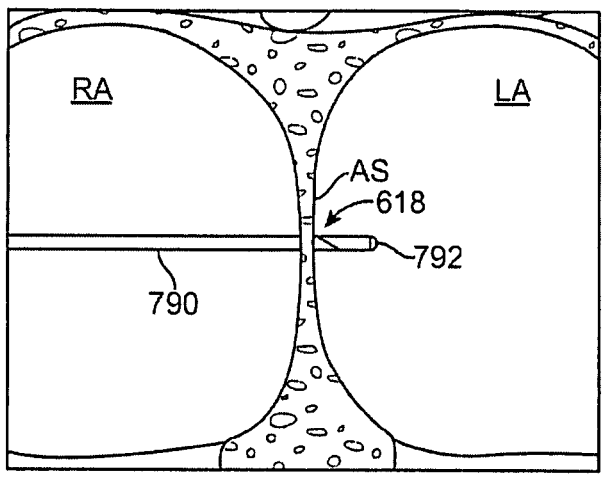
Figure 83E:
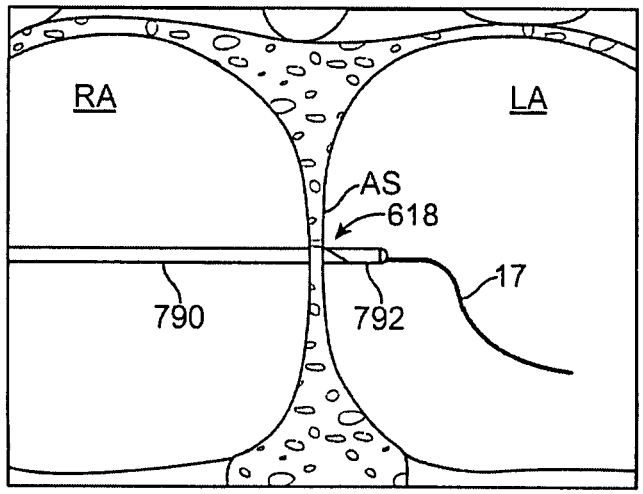

As shown in FIG. 83A, Veres-type needle 790 may be positioned adjacent to the atrial septum AS. The blunt end 792 of needle 790 may be advanced until it is proximate to or directly contacts the septal wall. Blunt end 792 may then be retracted proximally into the body of needle 790, as shown in FIG. 83B, whereupon the sharpened needle tip of needle 790 may be penetrated through the septum AS while blunt end 792 remains retracted proximally of the piercing tip, as shown in FIG. 83C. After passing through the septal wall AS, blunt end 792 may spring back to its original position, as shown in FIG. 83D. As shown in FIG. 83E, guidewire 17 can then be passed through a lumen defined through needle 790 and blunt end 792 to cross from the right atrium RA to the left atrium LA. Once guidewire 17 has been sufficiently deployed, needle 790 may be withdrawn leaving guidewire 17 passing through puncture 618 and the imaging hood 12 and catheter may be removed as well.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A tissue imaging and treatment system, comprising:
   a deployment catheter defining at least one lumen therethrough;
   a hood projecting distally from the deployment catheter and defining an open area therein, wherein the open area is in fluid communication with the at least one lumen;
   a transparent double-layered distal membrane disposed upon a distal end of the hood and at least partially over the open area, the double-layered distal membrane defining a plurality of apertures through the double-layered distal membrane with an inflatable space between layers of the double-layered membrane, the apertures being structured such that inflation of the inflatable space reduces a diameter of the apertures; and
   a visualization element disposed within or adjacent to the hood for visualizing tissue adjacent to the open area.

2. The system of claim 1 further comprising a delivery catheter through which the deployment catheter is deliverable.

3. The system of claim 1 wherein the deployment catheter is steerable.

4. The system of claim 3 wherein the deployment catheter is steered via pulling at least one wire.

5. The system of claim 3 wherein the deployment catheter is steered via computer control.

6. The system of claim 1 wherein the hood is comprised of a compliant material.

7. The system of claim 1 wherein the hood defines a contact edge for placement against a tissue surface.

8. The system of claim 1 wherein the hood is adapted to self-expand into an expanded deployed configuration.

9. The system of claim 1 wherein the hood comprises one or more support struts along the hood.

10. The system of claim 1 wherein the hood is conically shaped.

11. The system of claim 1 wherein the visualization element comprises at least one optical fiber, CCD imager, or CMOS imager.

12. The system of claim 1 wherein the visualization element is disposed within a distal end of the deployment catheter.

13. The system of claim 1 wherein the visualization element is articulatable off-axis relative to a longitudinal axis of the deployment catheter.

14. The system of claim 1 further comprising a fluid reservoir fluidly coupled to the hood.

15. The system of claim 14 wherein the fluid reservoir comprises a syringe or pressurized fluid bag.

16. The system of claim 14 wherein the fluid comprises saline, plasma, water, or perfluorinated liquid.

17. The system of claim 1 further comprising a piercing instrument translatable through the hood and beyond the open area.

18. The system of claim 17 wherein the piercing instrument comprises a flexible shaft and a tapered distal end.

19. The system of claim 17 wherein the piercing instrument defines a lumen therethrough.

20. The system of claim 19 further comprising a guidewire which is advanceable through the piercing instrument lumen.

21. The system of claim 17 wherein the piercing instrument further comprises a tissue engager proximal to or at a distal end of the piercing instrument.

22. The system of claim 21 wherein the tissue engager comprises helical threading.

23. The system of claim 17 wherein the piercing instrument comprises a Veres-type piercing needle having a retractable blunt tip positioned through a lumen of the needle.

24. The system of claim 17 further comprising a tissue engager translatable through the membrane and beyond the open area adjacent to the piercing instrument.

25. The system of claim 24 wherein the tissue engager comprises a helical engager disposed upon a flexible shaft.

26. The system of claim 24 wherein the tissue engager defines a lumen therethrough.

27. The system of claim 24 wherein the tissue engager comprises a grasper.

28. The system of claim 1 further comprising an inflatable balloon which is expandable within or distal to the open area of the hood.

29. The system of claim 28 wherein the inflatable balloon comprises a transparent membrane through which the visualization element can image the adjacent tissue.

30. The system of claim 1 further comprising an introducer sheath through which the deployment catheter is advanceable.

31. The system of claim 30 wherein a distal portion of the introducer sheath is curved or pre-bent such that the distal portion is angled relative a longitudinal axis of the sheath.

32. The system of claim 1 wherein a central aperture is positioned coaxially with the deployment catheter.

33. The system of claim 32 wherein the central aperture has a diameter of at least 1 mm and less than a diameter of an outer lip of the hood.

34. The system of claim 1 wherein the plurality of apertures are adapted to adjust from a first diameter to a second diameter which is smaller than the first diameter upon increased pressure within the inflatable space.

35. The system of claim 1 wherein the hood defines a guidewire lumen along its surface.

36. The system of claim 1 wherein the deployment catheter defines a guidewire lumen along its surface proximal to the hood.

37. The system of claim 17 wherein the piercing instrument defines at least one visual indicator along its outer surface to provide a direct indication of instrument position relative to tissue adjacent to the open area when pierced therein.

38. The system of claim 37 wherein the at least one visual indicator comprises a plurality of colors signifying relative instrument position.

39. The system of claim 1 further comprising at least one electrode in communication with the open area.

40. The system of claim 1 further comprising an ablation probe positionable within the open area.

41. The system of claim 1 further comprising one or more electrodes positionable into contact with tissue adjacent to the open area.

* * * * *